US010266894B2

(12) United States Patent
Sandberg et al.

(10) Patent No.: US 10,266,894 B2
(45) Date of Patent: Apr. 23, 2019

(54) METHODS AND COMPOSITIONS FOR CDNA SYNTHESIS AND SINGLE-CELL TRANSCRIPTOME PROFILING USING TEMPLATE SWITCHING REACTION

(71) Applicant: LUDWIG INSTITUTE FOR CANCER RESEARCH, New York, NY (US)

(72) Inventors: Rickard Sandberg, Stockholm (SE); Simone Picelli, Stockholm (SE); Omid R. Faridani, Stockholm (SE)

(73) Assignee: LUDWIG INSTITUTE FOR CANCER RESEARCH LTD, Zurich (CH)

( * ) Notice: Subject to any disclaimer, the term of this patent is extended or adjusted under 35 U.S.C. 154(b) by 438 days.

(21) Appl. No.: 14/912,556

(22) PCT Filed: Aug. 22, 2014

(86) PCT No.: PCT/US2014/052233
§ 371 (c)(1),
(2) Date: Feb. 17, 2016

(87) PCT Pub. No.: WO2015/027135
PCT Pub. Date: Feb. 26, 2015

(65) Prior Publication Data
US 2016/0258016 A1  Sep. 8, 2016

Related U.S. Application Data
(60) Provisional application No. 61/869,220, filed on Aug. 23, 2013.

(51) Int. Cl.
| C12Q 1/6809 | (2018.01) |
| C12Q 1/6883 | (2018.01) |
| C12Q 1/6853 | (2018.01) |
| C12P 19/34  | (2006.01) |

(52) U.S. Cl.
CPC ............ *C12Q 1/6883* (2013.01); *C12P 19/34* (2013.01); *C12Q 1/6809* (2013.01); *C12Q 1/6853* (2013.01); *C12Q 2600/158* (2013.01)

(58) Field of Classification Search
None
See application file for complete search history.

(56) References Cited

U.S. PATENT DOCUMENTS

2012/0010091 A1  1/2012  Linnarson

FOREIGN PATENT DOCUMENTS

| EP | 0871780 A2 | 10/1998 |
| EP | 1161561 B1 | 12/2001 |
| JP | 2000-502905 A | 3/2000 |
| WO | 97/24455 A2 | 7/1997 |
| WO | WO-2010/117620 A2 | 10/2010 |
| WO | 2012/103545 A1 | 8/2012 |
| WO | 2012/106546 A2 | 8/2012 |
| WO | WO-2012/129363 A2 | 9/2012 |

OTHER PUBLICATIONS

Karrer et al (PNAS 92:3814-8) (Year: 1995).*
Pentalidis, L. et al., "Global amplification of mRNA by template-switching PCR: linearity and application to microarray analysis.", Nucleic Acids Research, 2003, vol. 31, No. 22, e142 (pp. 1-7).
Hong, J. et al., "Enhanced detection of enteroviruses in clinical samples by reverse transcription-PCR using complementary locked primer technology.", Journal of Clinical Microbiology, 2010, vol. 48, No. 2, pp. 615-616.
Burbano, C.S. et al., "LNA-substituted degenerate primers improve detection of nitrogenase gene transcription in environmental samples.", Environmental Microbiology Reports, 2010, vol. 2, pp. 251-257.
Harbers, M. et al., "Comparison of RNA- or LNA-hybrid oligonucleotides in template-wwitching reactions for high-speed sequencing library pre paration.", BMC Genomics, Sep. 30, 2013, vol. 14, 665 (pp. 1-6).
Kejun Feng et al., "High-sensitive electrochemical detection of point mutation based on polymerization-induced enzymatic amplification", Biosensors and Bioelectronics, Elsevier BV, NL, vol. 26, No. 7, Dec. 13, 2010, pp. 3187-3191.
Spiess et al.: "A Highly Efficient Method for Long-Chain cDNA Synthesis Using Trehaloseand Betaine", Feb. 15, 2002, vol. 301, No. 2, pp. 168-174.
Kapteyn, et al.: "Incorporation of Non-Natural Nucleotides into Template-Switching Oligonucleotides Reduces Background and Improves of cDNA Synthesis from Very Small RNA Samples", BMC Genomics, Jul. 2, 2010, vol. 11, No. 413, pp. 1-9.

* cited by examiner

*Primary Examiner* — Christopher M Gross
(74) *Attorney, Agent, or Firm* — Fox Rothschild LLP

(57) ABSTRACT

This application discloses methods for cDN'A synthesis with improved reverse transcription, template switching and pre-amplification to increase both yield and average length of cDNA libraries generated from individual cells. The new methods include exchanging a single nucleoside residue for a locked nucleic acid (INA) at the TSO 3' end, using a methyl group donor, and/or a MgCb concentration higher than conventionally used. Single-cell transcriptome analyses incorporating these differences have full-length coverage, improved sensitivity and accuracy, have less bias and are more amendable to cost-effective automation. The invention also provides cDNA molecules comprising a locked nucleic acid at the 3'-end, compositions and cDNA libraries comprising these cDNA molecules, and methods for single-cell transcriptome profiling.

24 Claims, 14 Drawing Sheets

Specification includes a Sequence Listing.

A

B

SEQUENCE LISTING

```
<160> NUMBER OF SEQ ID NOS: 2

<210> SEQ ID NO 1
<211> LENGTH: 57
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (57)..(57)
<223> OTHER INFORMATION: n is a, c, g, or t

<400> SEQUENCE: 1
aagcagtggt atcaacgcag agtactttt ttttttttt tttttttttt tttttvn      57

<210> SEQ ID NO 2
<211> LENGTH: 23
<212> TYPE: DNA
<213> ORGANISM: Artificial
<220> FEATURE:
<223> OTHER INFORMATION: Synthetic primer

<400> SEQUENCE: 2
aagcagtggt atcaacgcag agt                                         23
```

METHODS AND COMPOSITIONS FOR CDNA SYNTHESIS AND SINGLE-CELL TRANSCRIPTOME PROFILING USING TEMPLATE SWITCHING REACTION

CROSS-REFERENCE TO RELATED APPLICATIONS

The present application is a U.S. national phase application of International Application No. PCT/US2014/052233, filed Aug. 22, 2014, which in turn claims priority to U.S. Provisional Patent Application Ser. No. 61/869,220, filed Aug. 23, 2014, the contents of both of which are hereby incorporated by reference in their entireties.

FIELD OF THE INVENTION

The present invention relates to methods for synthesis of double stranded cDNA with improved yield and average length, and cDNA molecules synthesized and cDNA libraries generated from individual cells.

BACKGROUND OF THE INVENTION

Single-cell gene expression analyses hold promise to characterize cellular heterogeneity, but current methods sacrifice either the coverage, sensitivity or throughput. Several methods exist for full-length cDNA construction from large amounts of RNA, including cap enrichment procedures (Maruyama, K. & Sugano, S., *Gene* 138, 171-174 (1994); Carninci, P. & Hayashizaki, Y., *Meth. Enzymol.* 303, 19-44 (1999); Das, M., et al., *Physiol. Genomics* 6, 57-80 (2001)), but it is still challenging to obtain full-length coverage from single-cell amounts of RNA. Existing methods use either 3' end polyA-tailing of cDNA (e.g., Tang, F. et al., *Nat. Methods* 6, 377-382 (2009); Sasagawa, Y. et al., *Genome Biol.* 14, R31 (2013)) or template switching (Zhu, Y. Y., et al., *BioTechniques* 30, 892-897 (2001); Ramsköld, D. et al., *Nat. Biotechnol.* 30, 777-782 (2012)), whereas other methods sacrifice full-length coverage altogether for early multiplexing (Islam, S. et al., *Genome Res.* (2011). doi:10.1101/gr.110882.110; Hashimshony, T., et al., *Cell Rep.* 2, 666-673 (2012)). It has recently been shown that Smart-Seq, which relies on template switching, has more even read coverage across transcripts than polyA-tailing methods (Ramsköld, D. et al., *Nat Biotechnol.* 30, 777-782 (2012)), consistent with the common use of template switching in applications designed to directly capture RNA 5' ends, including nanoCAGE (Plessy, C. et al., *Nat. Methods* 7, 528-534 (2010)) and STRT (Islam, S. et al., *Genome Res.* (2011). doi:10.1101/gr.110882.110). Single-cell applications utilizing template switching are dependent upon the efficiency of the reverse transcription, the template switching reaction, and a uniform polymerase chain reaction (PCR) preamplification to obtain representative cDNA in sufficient amounts for sequencing. Despite the widespread use of these reactions, no systematic efforts to improve cDNA library yield and average length from single-cell amounts have been reported.

SUMMARY OF THE INVENTION

The present invention provides improved methods for synthesis of cDNA, in particular, in the reverse transcription, template switching and preamplification of single cell applications utilizing template switching reactions, to increase both yield and average length of cDNA libraries generated from individual cells. Single-cell transcriptome analyses incorporating these differences have improved sensitivity and accuracy, and are less biased and more amenable to cost-effective automation.

Specifically, to improve full-length transcriptome profiling from single cells, this application discloses evaluation of a large number of variations to reverse transcription, template switching oligonucleotides (TSO) and PCR preamplification, and comparison of the results to commercial Smart-Seq (hereafter called SMARTer®) in terms of cDNA library yield and length. The modifications disclosed herein surprisingly and significantly increased both the yield and length of the cDNA obtained from as little as 1 ng of starting total RNA.

In one embodiment, the present invention provides a method for preparing DNA that is complementary to an RNA molecule, the method comprising conducting a reverse transcription reaction in the presence of a template switching oligonucleotide (TSO) comprising a locked nucleic acid residue.

In another embodiment, the present invention provides a method of increasing the yield of cDNA, comprising use of an additive, such as a methyl group donor, in the cDNA synthesis. In one embodiment, the methyl group donor is betaine.

In another embodiment, the present invention provides a method of increasing the yield of cDNA, comprising use of an increased concentration of metal salt, for example, $MgCl_2$, in the synthesis of cDNA.

In a preferred embodiment, the method comprises use of a methyl group donor in combination with an increased concentration of $MgCl_2$ in the cDNA synthesis. In a particularly preferred embodiment, the method comprises use of methyl group donor betaine in combination with an increased concentration of $MgCl_2$, which has shown a significant positive effect on the yields of cDNA.

In another embodiment, the present invention provides a method of increasing the average length of a preamplified cDNA, comprising administering dNTPs prior to the RNA denaturation rather than in the reverse transcriptase (RT) master mix.

In another embodiment, the present invention provides a cDNA library produced by a method according to any of the embodiments disclosed herein.

In another embodiment, the present invention provides use of a cDNA library produced according to any of the embodiments disclosed herein for single-cell transcriptome profiling.

In another embodiment, the present invention provides a method for analyzing gene expression in a plurality of single cells, comprising the steps of preparing a cDNA library according to a method according to any embodiment disclosed herein; and sequencing the cDNA library.

It has been demonstrated in accordance with the present invention that these methods performed on purified RNA are applicable to individual metazoan cells, including for example mammalian cells.

In another embodiment, the present invention provides a template switching oligonucleotide (TSO) comprising an LNA at its 3'-end.

In another embodiment, the present invention provides use of a TSO according to any of the embodiments disclosed herein for synthesis of double stranded cDNA.

These and other aspects of the present invention will be better appreciated by reference to the following drawings and detailed description.

DETAILED DESCRIPTION OF THE INVENTION

Figure 1:
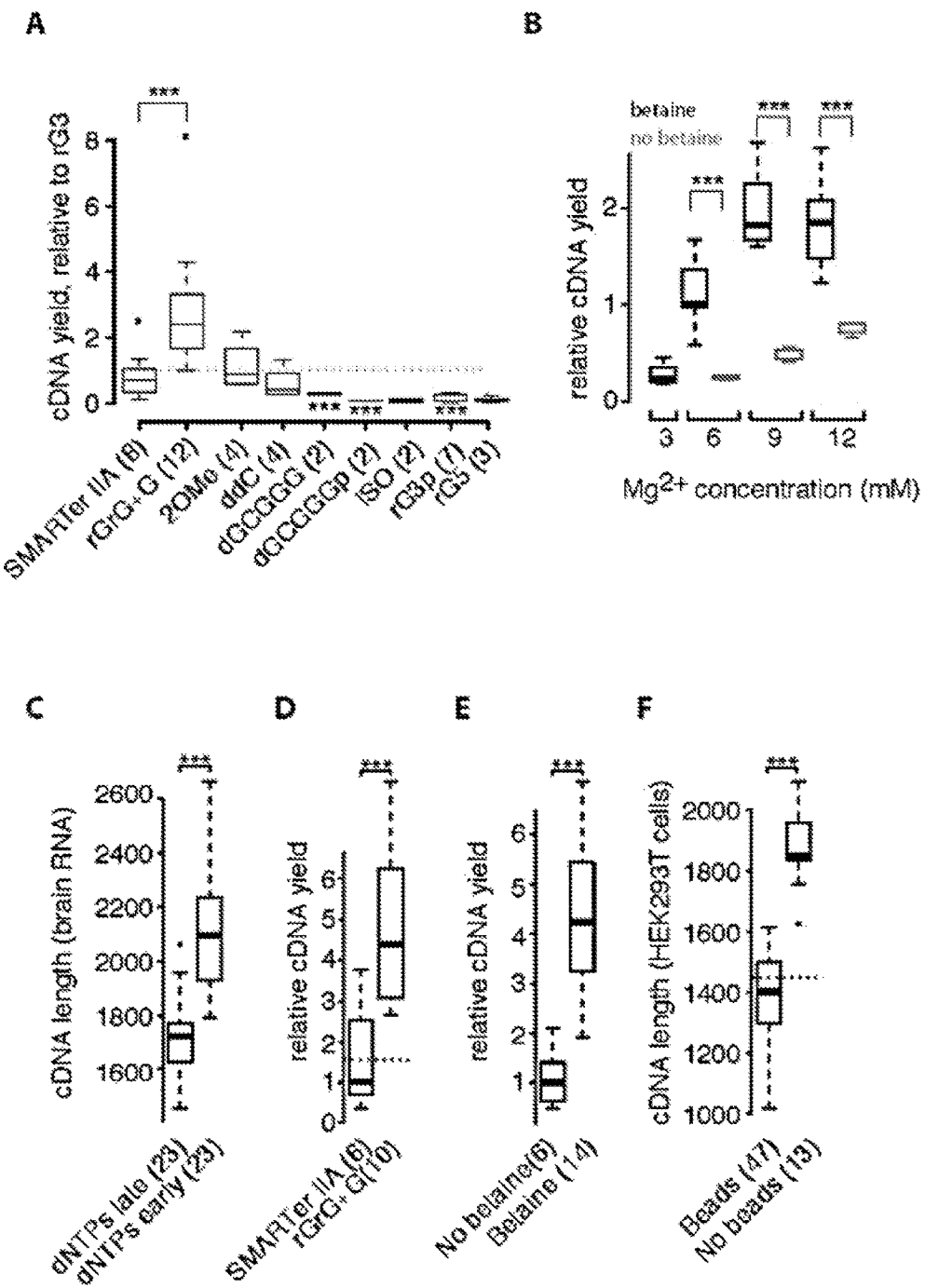
FIG. 1 illustrates improvements in cDNA library yield and length. (A) Median yield of preamplified cDNA from 1 ng total RNA using different template switching oligonucleotides, relative to those obtained using the rG3 oligo. All oligo sequences are found in Table 1. (B) Median yield of preamplified cDNA from 1 ng total RNA in reactions with betaine (black) or without (gray) and as a function of increasing $Mg^{2+}$ concentration, relative to cDNA yields obtained using SMARTer®-like conditions (betaine and 6 mM $Mg^{2+}$). (C) Length of preamplified cDNA generated from 1 ng total mouse brain RNA in reactions that deployed dNTPs prior to RNA denaturation (early) or in RT master mix (late). (D) Median yield of preamplified cDNA from HEK293T cells using the LNA-G and SMARTer® IIA template switching oligos with the optimized protocol. Dashed lines indicate median yield from commercial SMARTer® reactions. (E) Median yield of preamplified cDNA from DG-75 cells in reactions with or without betaine. (F) Lengths of cDNA libraries generated from single HEK293T cells in reactions with or without bead extraction. Note that brain mRNAs are naturally longer than cell line mRNAs. (A-F) The replicate measurements are represented as boxplots with the numbers of replicates per condition indicated in parenthesis. Significant differences in mean yield or length were determined using the Student's t-test.

This application discloses methods for cDNA synthesis with improved reverse transcription, template switching and preamplification to increase both yield and average length of cDNA libraries generated from individual cells.

In one embodiment, the present invention provides a method for preparing DNA that is complementary to an RNA molecule, comprising the steps of:

annealing a cDNA synthesis primer to the RNA molecule and synthesizing a first cDNA strand to form an RNA-cDNA intermediate; and conducting a reverse transcriptase reaction by contacting the RNA-cDNA intermediate with a template switching oligonucleotide (TSO), wherein the TSO comprises a locked nucleic acid (LNA) at its 3'-end, under conditions suitable for extension of the first DNA strand that is complementary to the RNA molecule, rendering it additionally complementary to the TSO.

In another embodiment of the present invention, the reverse transcription reaction is conducted in the presence of a methyl group donor and a metal salt.

In another embodiment of the present invention, the methyl group donor is betaine.

In another embodiment of the present invention, the metal salt is a magnesium salt.

In another embodiment of the present invention, the magnesium salt has a concentration of at least 7 mM, at least 8 mM, or at least 9 mM.

In another embodiment of the present invention, the template switching oligonucleotide optionally comprises one or two ribonucleotide residues.

In another embodiment of the present invention, the template switching oligonucleotide comprises at least one or two ribonucleotide residues and an LNA residue.

In another embodiment of the present invention, the at least one or two ribonucleotide residues are riboguanine.

In another embodiment of the present invention, the locked nucleic acid residue is selected from the group consisting of locked guanine, locked adenine, locked uracil, locked thymine, locked cytosine, and locked 5-methylcytosine.

In another embodiment of the present invention, the locked nucleic acid residue is locked guanine.

In another embodiment of the present invention, the locked nucleic acid residue is at the 3'-most position.

In another embodiment of the present invention, the template switching oligonucleotide comprises at the 3'-end two ribonucleotide residues and one locked nucleotide residue characterized by formula rGrG+N, wherein +N represents a locked nucleotide residue.

In another embodiment of the present invention, the template switching oligonucleotide comprises rGrG+G.

In another embodiment of the present invention, the methyl group donor is betaine, and the metal salt is $MgCl_2$ at a concentration of at least 9 mM.

In another embodiment of the present invention, the method further comprises amplifying the DNA strand that is complementary to the RNA molecule and the template switching oligonucleotide using an oligonucleotide primer.

In another embodiment of the present invention, the template switching oligonucleotide is selected from the oligonucleotides in Table S2.

In another embodiment of the present invention, the cDNA synthesis primer is an oligo-dT primer.

In another embodiment of the present invention, the cDNA is synthesized on beads comprising an anchored oligo-dT primer.

In another embodiment of the present invention, the oligo-dT primer comprises a sequence of 5'-AAGCAGTGGTATCAACGCAGAGTACT$_{30}$VN-3', wherein "N" is any nucleoside base, and "V" is selected from the group consisting of "A", "C" and "G".

In another embodiment of the present invention, the method further comprises PCR preamplification, tagmentation, and final PCR amplification.

In another embodiment of the present invention, the PCR preamplification is conducted without purifying the cDNA obtained from reverse transcription reaction.

In another embodiment of the present invention, the RNA is total RNA in a cell.

In another embodiment, the present invention provides a cDNA library produced by the method according to any embodiment disclosed herein.

In another embodiment, the present invention provides use of a cDNA library produced by the method according to any embodiment disclosed herein for single-cell transcriptome profiling.

In another embodiment, the present invention provides a method for analyzing gene expression in a plurality of single cells, the method comprising the steps of: preparing a cDNA library produced by the method according to any embodiment disclosed herein; and sequencing the cDNA library.

In another embodiment, the present invention provides a template switching oligonucleotide (TSO) comprising a locked nucleotide residue at the 3'-end. The TSOs of the present invention can be used in the synthesis of cDNA to improve yield and length.

In another embodiment, the TSO comprises three nucleotide residues at the 3'-end, wherein said three nucleotide residues are selected from the group consisting of +N+N+N, N+N+N, NN+N, rN+N+N, and rNrN+N, wherein N at each occurrence is independently a deoxyribonucleotide residue, rN at each occurrence is independently a ribonucleotide residue, and +N at each occurrence is independently a locked nucleotide residue.

In one embodiment, the portion of the TSO that is on the 5' side of the three nucleotide residues at the 3'-end, also referred to herein as the 5'-portion, comprises an arbitrary nucleotide sequence comprised of ribonucleotides, deoxyribonucleotides, or mixtures thereof. In one preferred embodiment, the 5'-portion of the TSO comprises all ribonucleotides. In another preferred embodiment, the 5'-portion of the TSO comprises all deoxyribonucleotides.

In another embodiment, the locked nucleotide residue in the TSOs is selected from the group consisting of locked guanine, locked adenine, locked uracil, locked thymine, locked cytosine, and locked 5-methylcytosine In another embodiment, the three nucleotide residues at the 3'-end of the TSOs are NN+G or rNrN+G, wherein N at each occurrence is independently a deoxyribonucleotide residue, and rN at each occurrence is independently a ribonucleotide residue.

In another embodiment, the three nucleotide residues at the 3'-end of the TSOs are rGrG+N, wherein +N is locked nucleotide residue.

In another embodiment, the three nucleotide residues at the 3'-end of the TSOs are rGrG+G.

The TSOs preferably have a length of from about 10 to about 50 nucleotides, or from about 15 to about 45 nucleotides, or from about 20 to about 40 nucleotides, or from about 24 to about 35 nucleotides, or about 30 nucleotides.

In another embodiment, the present invention provides use of a TSO according to any one of the embodiments disclosed herein in the synthesis of a cDNA.

Examples of metal cations useful for the present invention include, but are not limited to, $Mg^{2+}$ and $Mn^{2+}$, with $Mg^{2+}$ preferred; and their concentrations can be in the range of 0-30 µM, inclusive, with a preferred range of 3-20 µM, and a more preferred range of 9-12 µM.

In addition to methyl donor betaine, other additives that may be added in the cDNA synthesis of the present invention include, but are not limited to, trehalose, sucrose, glucose, maltose, DMSO (dimethyl sulfoxide), formamide, non-ionic detergents, TMAC (tetramethylammonium chloride), 7-deaza-2'-deoxyguanosine ($dC^7GTP$), bovine serum albumin (BSA), and T4 gene 32 protein.

The present invention is applicable to reactions using all reverse transcriptases that are MMLV-related and have template switching activity. MMLV-related reverse transcriptases include wild-type Moloney murine leukemia virus and its variants, including for example derivatives lacking RNase H activity such as SUPER-SCRIPT II (Invitrogen), POWER SCRIPT (BD Biosciences) and SMART SCRIBE (Clontech). TSOs useful for the present invention may comprise barcodes, including but not limited to molecular barcodes or sample barcodes.

The cDNA synthesized according to the present invention may have applications as cDNA synthesized according to any literature methods, including but not limited to construction of small quantity cDNA library, single-cell cDNA analyses, single-cell gene expression analyses, few-cell cDNA analyses, few-cell gene expression analyses, single-cell qPCR analyses (that use this preamplification step), and cap capturing based amplification.

The following non-limiting examples illustrate certain aspects of the present invention.

EXAMPLES

Example 1

Methods
Experiments Using Total RNA

RNA experiments were performed using the Control Total RNA supplied with the SMARTer® Ultra Low RNA Kit for Illumina Sequencing (Clontech), extracted from mouse brain. One microliter of a 1 ng/µl solution was used in each experiment and mixed with 1 µl of anchored oligo-dT primer (10 mM, 5'-AAGCAGTGGTATCAACGCAGAGT $ACT_{30}$ VN-3', where "N" is any base and "V" is either "A", "C" or "G") and 1 µl of dNTP mix (10 mM, Fermentas), denaturated at 72° C. for 3 min and immediately placed on ice afterwards. Seven µl of the first strand reaction mix containing 0.50 µl SuperScript II RT (200 U ml-1, Invitrogen), 0.25 µl RNAse inhibitor (20 U ml-1, Clontech), 2 µl Superscript II First-Strand Buffer (5×, Invitrogen), 0.25 µl DTT (100 mM, Invitrogen), 2 µl betaine (5 M, Sigma), 0.9 µl $MgCl_2$ (100 mM, Sigma), 1 µl TSO (10 µM, the complete list of the oligos can be found in Table S1) and 0.1 µl Nuclease-free water (Gibco) were added to each sample. Reverse transcription reaction was carried out by incubating at 42° C. for 90 min, followed by 10 cycles of (50° C. for 2 min, 42° C. for 2 min). Finally, the RT was inactivated by incubation at 70° C. for 15 min.

PCR Pre-Amplification

In the original Smart-Seq protocol purification with Ampure XP beads is performed after first strand cDNA synthesis. PCR is then carried out directly on the cDNA immobilized on the beads, after adding 2 µl Advantage 2 Polymerase Mix (50×, Clontech), 5 µl Advantage 2 PCR Buffer (10×, Clontech), 2 µl dNTP mix (10 mM, Clontech), 2 µl IS PCR primer (12 µM, Clontech) and 39 µl nuclease-free water to a final reaction volume of 50 µl. In the present examples the cDNA was not purified after RT but just added the same PCR master mix, taking into account that the volume after first strand cDNA synthesis is 10 µl and adjusting the amount of water accordingly. Reaction was incubated at 95° C. 1 min, then cycled 15 times between (95° C. 15 sec, 65° C. 30 sec, 68° C. 6 min), with a final extension at 72° C. for 10 min.

A second modification that significantly improved cDNA yield was the replacement of Advantage 2 Polymerase mix with KAPA HiFi HotStart ReadyMix (KAPA Biosystems). Purification after first strand cDNA synthesis was omitted also in this case. The PCR master mix had the following composition: 25 µl KAPA HiFi HotStart ReadyMix (2×, KAPA Biosystems), 1 µl IS PCR primers (10 mM, 5'-AAGCAGTGGTATCAACGCAGAGT-3') and 14 µl nuclease-free water (Gibco). The program used was as follows: 98° C. 3 min, then 15 cycles of (98° C. 15 sec, 67° C. 20 sec, 72° C. 6 min), with a final extension at 72° C. for 5 min.

Regardless of the PCR protocol used, PCR was purified using a 1:1 ratio of AMPure XP beads (Beckman Coulter), performing the final elution in 15 µl of EB solution (Qiagen). Library size distribution was checked on a High-Sensitivity DNA chip (Agilent Bioanalyzer) after a 1:5 dilution. The expected average size should be around 1.5-2.0 kb and the fraction of fragments below 300 bp should be negligible. To evaluate the performance of the different modifications introduced in the protocol, the amount of cDNA comprised in the interval 300-9000 bp in the Agilent Bioanalyzer plot was assessed.

Tagmentation Reaction and Final PCR Amplification

Five nanograms of cDNA were then used for the tagmentation reaction carried out with Nextera® DNA Sample Preparation kit (Illumina), adding 25 µl of 2× Tagment DNA Buffer and 5 µl of Tagment DNA Enzyme, in a final volume of 50 µl. Tagmentation reaction was incubated at 55° C. for 5 min, followed by purification with DNA Clean & Concentrator™-5 kit (Zymo Research) with a final elution in 20 µl Resuspension Buffer (RSB) from the Nextera® kit. The whole volume was then used for limited-cycle enrichment PCR, along with 15 µl of Nextera® PCR Primer Mix (NPM), 5 µl of Index 1 primers (N7xx), 5 µl of Index 2 primers (N5xx) and 5 µl of PCR Primer Cocktail (PPC). A second amplification round was performed as follows: 72° C. 3 min, 98° C. 30 sec, then 5 cycles of (98° C. 10 sec, 63° C. 30 sec, 72° C. 3 min). Purification was done with a 1:1 ratio of AMPure XP beads and samples were loaded on a High-Sensitivity DNA chip to check the quality of the library, while quantification was done with Qubit High-Sensitivity DNA kit (Invitrogen). Libraries were diluted to a final concentration of 2 nM, pooled and sequenced on Illumina HiSeq 2000.

Single-Cell cDNA Isolation

Single HEK293T (human), DG-75 (human), C2C12 (mouse) and MEF (mouse) cells were manually picked under the microscope after resuspension in PBS. Volume of liquid was kept as low as possible, usually below 0.5 µl and preferably below 0.3 µl. Cells were then transferred to a 0.2 ml thin-wall PCR tube containing 2 µl of a mild hypotonic lysis buffer composed of 0.2% Triton X-100 (Sigma) and 2 U/µl of RNAse inhibitor (Clontech). Cells already picked were kept on ice throughout the process or stored at −80° C. if not used immediately. All the downstream steps were the same as when using total RNA (see above), with the only exception of the quality control with the High Sensitivity DNA chip, where samples were loaded pure (without dilution), due to the limited amount of cDNA obtained from RT in single cells.

When working with total RNA it was observed that cDNA yield could be increased using a double amount of TSO or different combinations of TSOs and PCR enzymes (data not shown). To validate this finding, some experiments on HEK293T cells were repeated using different amounts of TSO (1 or 2 µl of a 10 µM solution), TSO types (rGrGrG, rGrG+G or rGrG+N) or PCR enzymes (KAPA HiFi or Advantage 2). Sequencing results for the most significant comparisons are reported in Figures S2-S7. The final protocol (i.e. "optimized") refers to the one using only 1 µl of the 10 µM rGrG+G TSO and KAPA HiFi HotStart ReadyMix as enzyme in the first PCR (without AMPure XP bead purification).

Smart-Seq Experiments

To evaluate and compare the performance of the present method, cDNA libraries were generated with the same total RNA and single cells using the Smart-Seq protocol, following manufacturer's instructions (see Clontech manual). After PCR pre-amplification, 5 ng of cDNA were used for the tagmentation reaction and processed exactly in the same way as described above.

Statistical Analyses of cDNA Yield and Length

Performances of the different protocols were evaluated with regard to cDNA yield and average cDNA length according to the Bioanalyzer in the range of 300-9,000 bp. For mouse brain total RNA samples, each experimental variable was evaluated in a pairwise manner selecting a set of experiments where all other variables are identical. Within that set of experiments, the significance for a change in yield or length, between the two variables, was evaluated using Student's t-test and Wilcoxon rank sum test (Table 1, sheet B).

In the HEK293T cell experiments each optimized experimental setting was compared to each other, as well as to the SMARTer® protocol, using Student's t-test and Wilcoxon rank sum test (Table 3, sheet B). All analyses and figures were produced with using R.

Read Alignments and Gene Expression Estimation

Single-cell libraries were sequenced with Nextera dual indexes (i7+i5) on an Illumina HiSeq 2000, giving 43 bp insert reads after demultiplexing and removing cellular barcodes. The reads were aligned to human (hg19) or mouse (mm10) genomes using STAR v2.2.0 (Dobin et al. Bioinformatics 2013 29(1): 15-21) with default settings and filtered for uniquely mapping reads. Gene expression values were calculated as RPKM values for each transcript in Ensembl release 69 and RefSeq (February 2013) using rpkmforgenes (Ramsköld et al. PLoS Comp Biol., 5, e1000598, 2009).

Single-Cell RNA-Seq Sensitivity and Variability

Analyses of gene detection in single HEK293T cells (FIG. 2A, FIGS. 5A, and 7A) were calculated over all possible pairs of technical replicates from each experimental setting. Genes were binned by expression level in the two samples, and were considered detected if the RPKM was above 0.1 in both samples. The mean for all possible pairs of technical replicates within a group was used together with standard deviation using the adjusted Wald method. Analyses of variation (FIG. 2B and FIGS. 5B & 7B) were also calculated on pairs of samples, binning genes by the mean of log expression, excluding genes below 0.1 RPKM in either sample. As gene expression levels across single cells are often log normally distributed (Bengtsson Genome Res 2005 15(10): 1388-1392), absolute difference in $\log_{10}$ expression values and s.d. were calculated by multiplying mean difference in a bin with 0.886.

Analyses of Read Coverage and GC Tolerance

Figure 2:
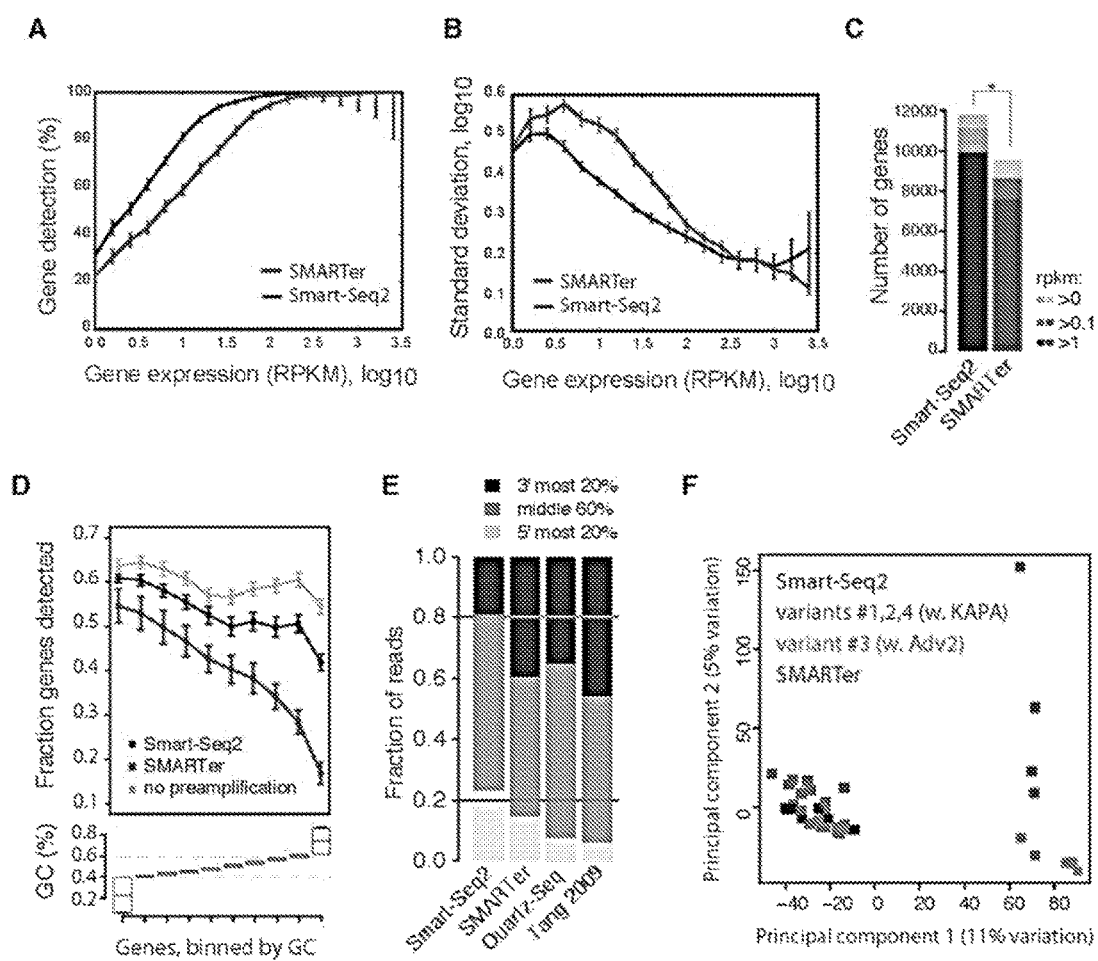
FIG. 2 illustrates sensitive full-length transcriptome profiling in single cells. (A) Percentage of genes reproducibly detected in replicate cells, binned according to expression level. All pair-wise comparisons were performed within replicates for the optimized protocol and SMARTer® and reported as the mean and 90% confidence interval. (B) Standard deviation in gene expression estimates within replicates in bins of genes sorted according to expression levels. Error bars, s.e.m. (n≥4). (C) The mean numbers of genes detected in HEK293T cells using SMARTer® and optimized protocol, at different RPKM cut-offs. Significant increase in gene detection in the optimized protocol was obtained at all RPKM thresholds (all with p<0.5; Student's t-test). (D) The mean fraction of genes detected as expressed (RPKM>1) in bins of genes sorted according to their GC content. The mRNA-Seq data from a human tissue was included as a no-preamplification control. Error bars denote SEM (n≥4), and the lower panel shows the GC range for genes in each bin. (E) The mean fraction of reads aligning to the 3' most 20% of the genes, 5' most 20% and the middle 60% for single-cell data generated using different protocols. (F) Principal component analyses of single-cell gene expression data showing the two most significant components. Cells are colored according to preamplification enzyme and protocol variant.
Figure 6:
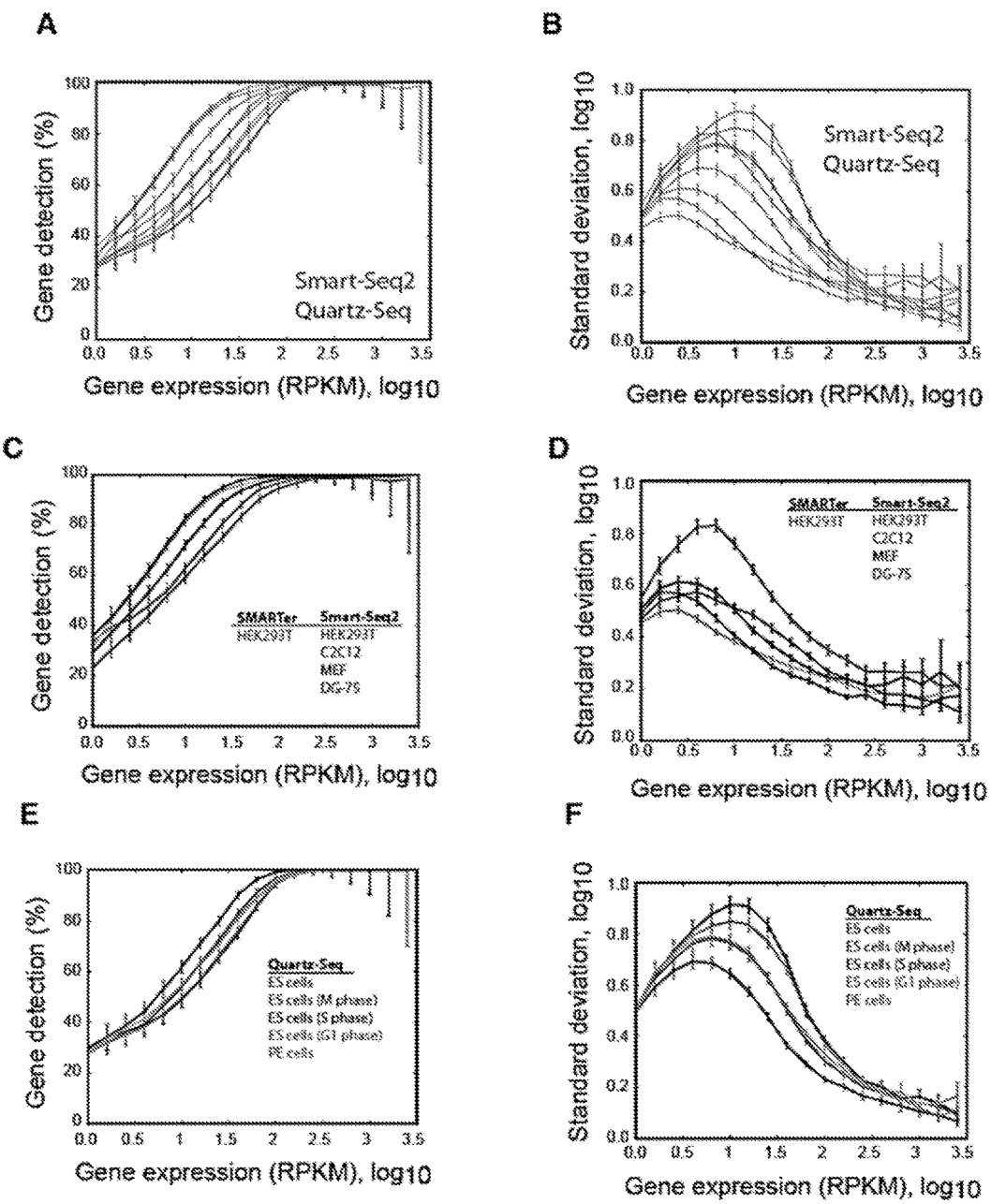
FIG. 6 illustrates comparison of single-cell transcriptomic data generated with Smart-Seq2, Quartz-Seq and SMARTer. (A) Percentage of genes reproducibly detected in replicate cells. All pair-wise comparisons were performed with Smart-Seq2 and Quartz-seq, and reported as the mean and 90% confidence interval. (B) Standard deviation in gene expression estimates in (A). (C) Percentage of genes reproducibly detected in replicate cells. All pair-wise comparisons were performed with Smart-Seq2 and SMARTer®, and reported as the mean and 90% confidence interval. (D) Standard deviation in gene expression estimates in (C). (E) Percentage of genes reproducibly detected in replicate cells. All pair-wise comparisons were performed with Quartz-seq, and reported as the mean and 90% confidence interval. (F) Standard deviation in gene expression estimates in (E).
Figure 8:
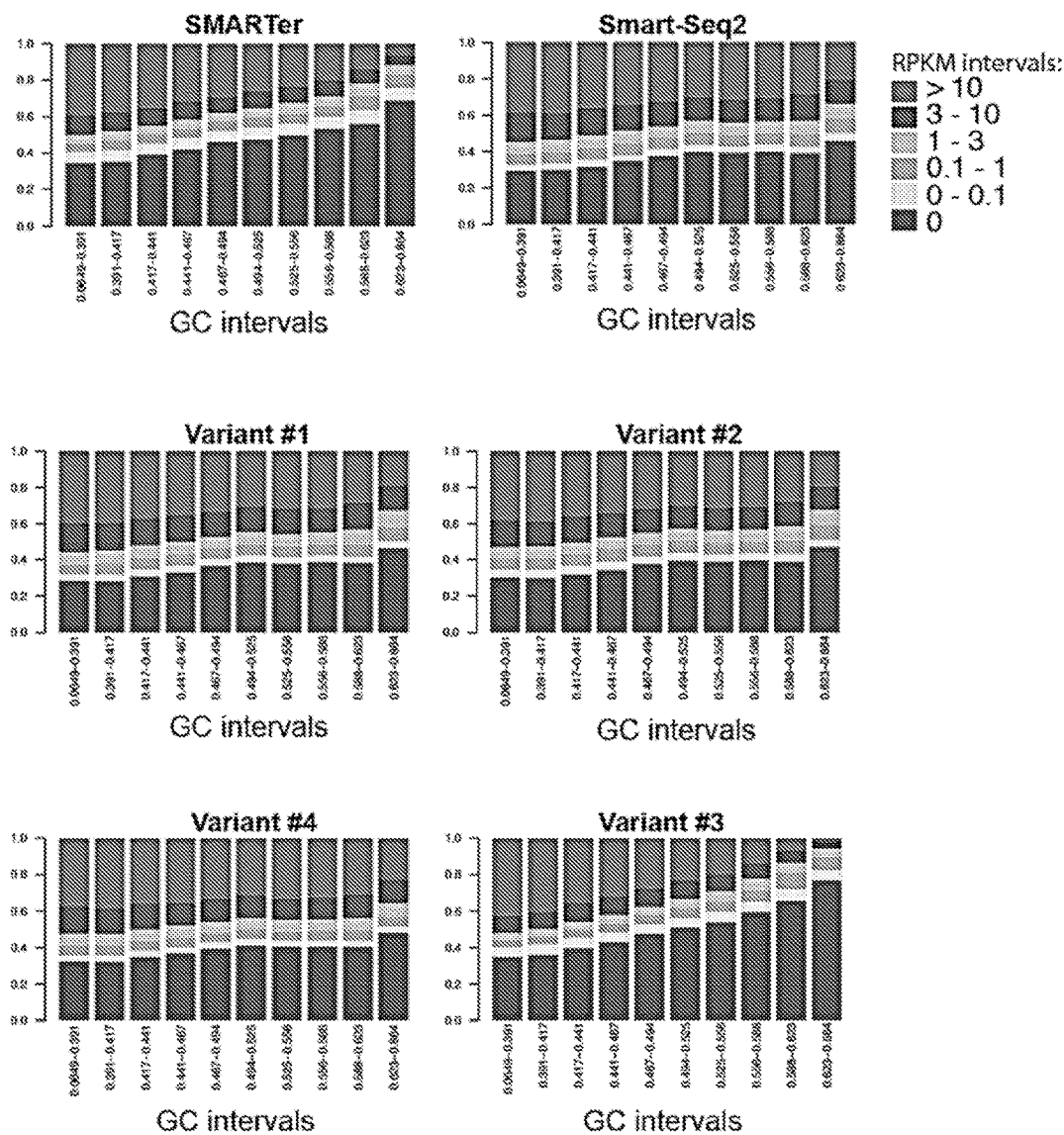
FIG. 8 illustrates gene expression and GC levels in single-cell RNA-Seq protocols.

Gene body coverage was calculated using the RSeQC-2.3.4 package (Wang, Wang and Li. Bioinformatics 2012; 28(16):2184-5) for the longest transcript of all protein coding genes (FIG. 2E and FIG. 8). Gene detection at different GC-content was calculated using longest transcript for all protein coding RefSeq genes that were binned by GC-content into 10 equal sized bins, and the numbers of genes with no detection, or detection at different RPKM cutoffs were calculated (FIG. 2D and FIG. 6).

Read Peak Analyses

Some genes displayed unexplained peaks with high density of reads within the gene body. To identify these regions, the gene bodies of each gene were divided into 101 equally sized bins and each gene with at least one bin with >5 standard deviation read density over the mean read distribution within that gene. In these analyses genes with low expressed genes (those with fewer reads than around 2,000-10,000 reads depending on the sequencing depth per cell) were discarded. The number of such genes in each cell is represented in FIG. 9A. And the genes with peaks in the highest number of HEK239T cells are displayed as heatmaps in FIG. 9B illustrating that the peaks are consistently found at the same position in all experiments.

Example 2

To improve full-length transcriptome profiling from single cells, a large number of variations to reverse transcription, template switching oligonucleotide (TSO) and PCR preamplification (in total 457 experiments) were evaluated, and the results were compared to commercial Smart-Seq (hereafter called SMARTer®) in terms of cDNA library yield and length (Table 1). Importantly, modifications were identified that significantly increased both cDNA yield and length obtained from 1 ng of starting total RNA (Table 1).

Figure 3:
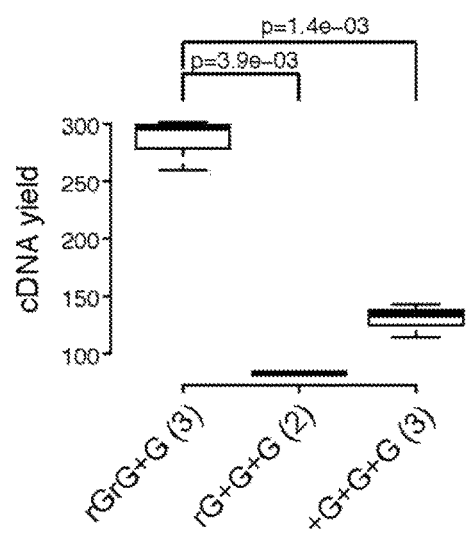
FIG. 3 shows cDNA yields using LNA bases in template switching oligonucleotides.

In particular, exchanging only a single guanylate for a locked nucleic acid (LNA) guanylate at the TSO 3' end (rGrG+G), led to a 2-fold increase in cDNA yield relative to the SMARTer® IIA oligo used in commercial Smart-Seq (p=0.003, Student's t-test; FIG. 1a, Table 2 and FIG. 3).

Additionally, it was discovered that the methyl group donor betaine in combination with higher $MgCl_2$ concentrations had a significant positive effect on yield (2-4 fold increase, p=0.0012, Student's t-test, for all comparisons) (FIG. 1b). The commercial Smart-Seq buffer has a final concentration of 6 mM $MgCl_2$, but it was found herein that higher yield is obtained when increasing the concentration to 9 mM or beyond. Finally, the average length of the preamplified cDNA increased with 370 nts when administering dNTPs prior to the RNA denaturation rather than in the RT master mix (p=7.8×10$^{-9}$, Student's t-test; FIG. 1c).

It was further demonstrated that these improvements obtained with purified RNA extended to cDNA reactions performed directly in lysates of individual human and mouse cells. To this end, single-cell cDNA libraries were generated from a total of 262 individual human or mouse cells (159 HEK293T, 34 DG-75, 30 C2C12 and 39 MEF cells) spanning different cell sizes and total RNA contents (Table 3). Analyses of the single-cell cDNA libraries demonstrated higher cDNA yields both with the use of the LNA-containing TSO (3-fold increase, p<0.001, Student's t-test; FIG. 1d) and with betaine together with high $Mg^{2+}$ concentrations (4-fold increase, p=3.7×10$^{-6}$, Student's t-test; FIG. 1e).

The sensitivity and accuracy of single-cell methods are limited by the efficiency of each sample-processing step. The SMARTer® protocol uses bead purification to remove unincorporated adaptors from the first strand cDNA reaction before the preamplification with Advantage 2 Polymerase (Adv2). However, performing bead purification in small volumes poses a significant recovery challenge for liquid handling automation. It was determined herein that KAPA HiFi Hot Start (KAPA) DNA Polymerase efficiently amplified first-strand cDNA directly after reverse transcription, with no need for prior bead purification. Libraries preamplified without bead purification had no reduction in yield, but the average cDNA length increased with 450 nts ($p=2.6 \times 10^{-12}$, Student's t-test; FIG. 1f) demonstrating that KAPA preamplification improves cDNA generation and offers a viable approach for Smart-Seq automation.

To demonstrate the significance of the improved cDNA generation on downstream applications, its impact on single-cell transcriptome profiling was assessed. To this end, single HEK293T cell libraries generated both according to the commercial SMARTer (n=4) and using variations of the present protocol were sequenced (Smart-Seq2, n=35) (Table 4).

Figure 4:
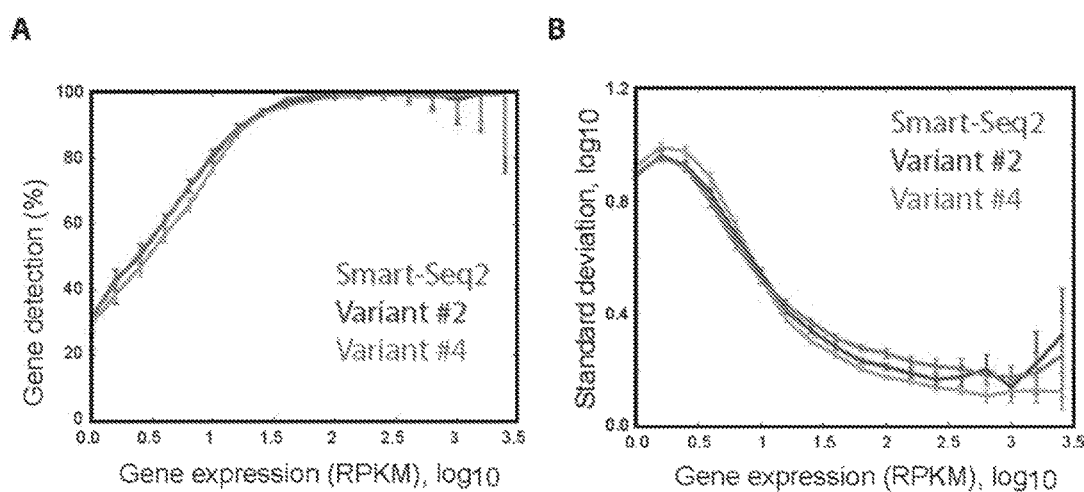
FIG. 4 illustrates single-cell RNA-Seq sensitivity and variability. (A) Percentage of genes reproducibly detected in replicate cells. (B) Standard deviation in gene expression estimates.
Figure 5:
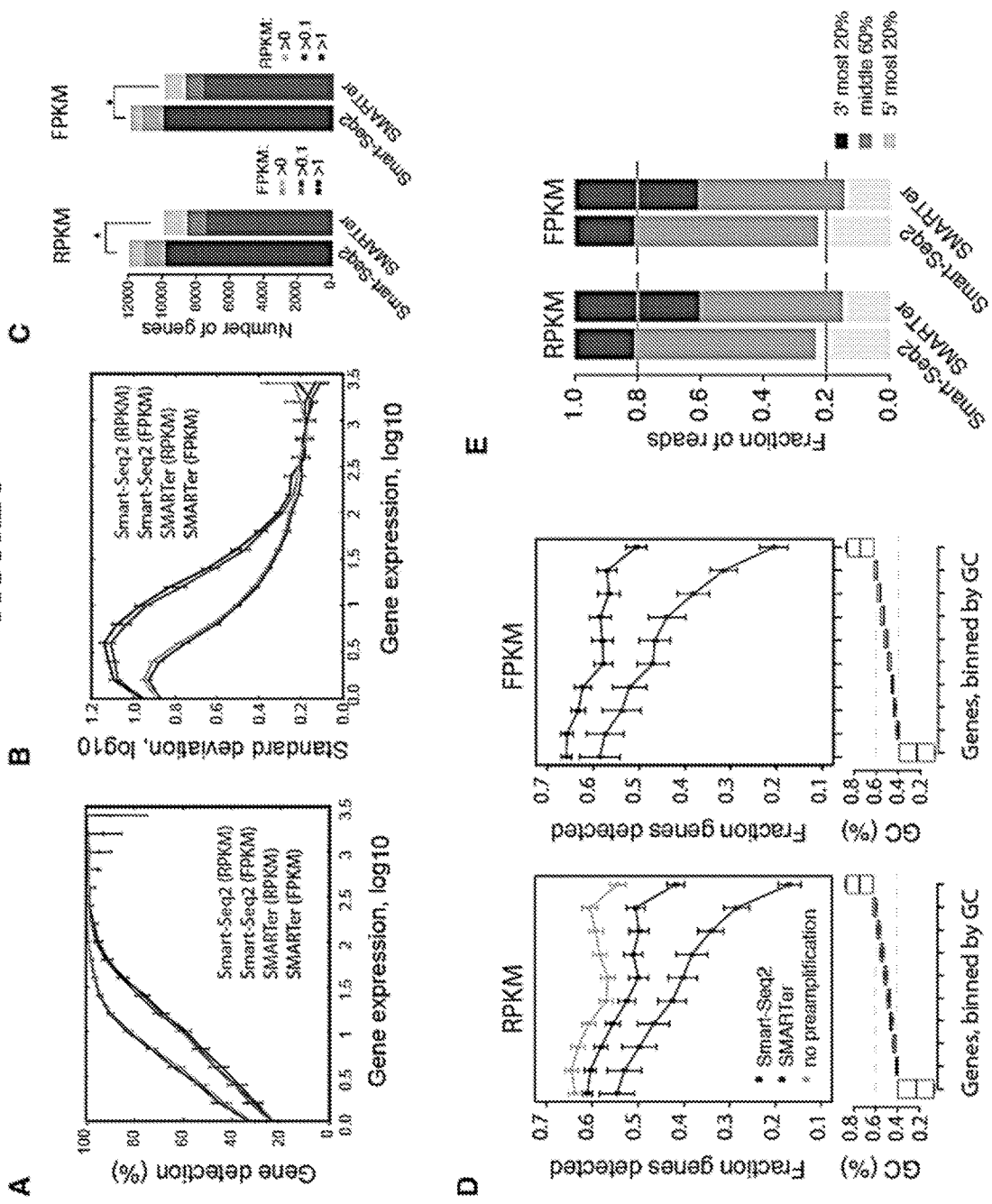
FIG. 5 illustrates validation of single-cell RNA-Seq results using another analysis pipeline. (A) Percentage of genes reproducibly detected in replicate cells. (B) Standard deviation in gene expression estimates. (C) The mean numbers of genes detected. (D) The mean fraction of genes detected as expressed. (E) The mean fraction of reads aligning to the 3' most 20% of the genes, 5' most 20% and the middle 60% for single-cell data generated using different protocols.
Figure 7:
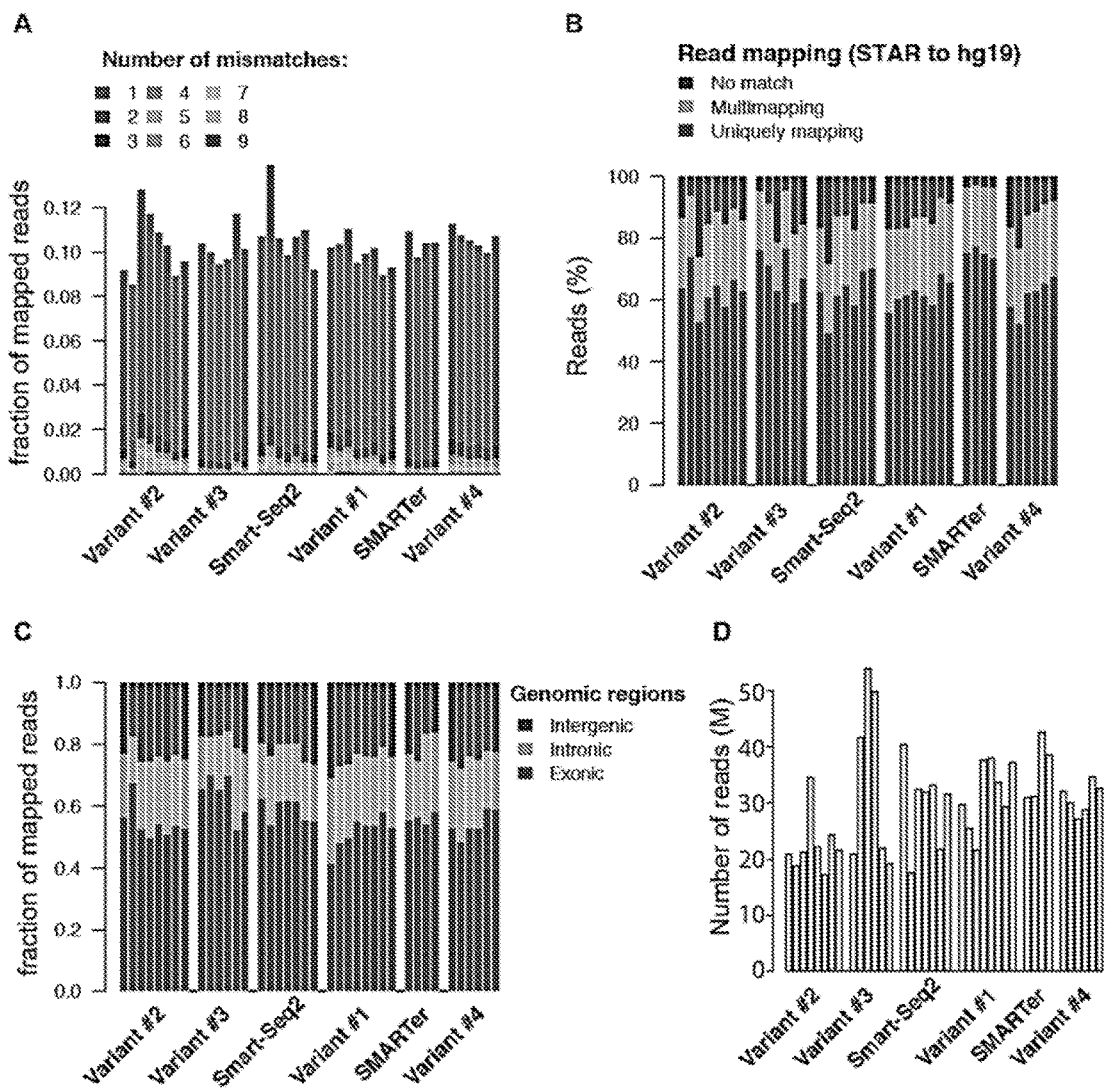
FIG. 7 illustrates mapping statistics for single-cell libraries generated using SMARTer, optimized Smart-Seq and variants of the optimized protocol. (A) Fraction of uniquely aligned reads with 1 to 9 mismatches for each single-cell RNA-Seq library. (B) Percentage of reads that aligned uniquely, aligned to multiple genomic coordinates, or did not align for all single-cell RNA-Seq libraries. (C) Fraction of uniquely aligned reads that mapped to exonic, intronic or intergenic regions. (D) Number of sequenced reads per cell and library preparation protocol.

The improved conversion of RNA to cDNA should improve gene expression profiling as more original RNA molecules are accessible for sequencing. Indeed, both a significant increase in the ability to detect gene expression (FIG. 2a) and lowered technical variation for low and medium abundance transcripts were observed (FIG. 2b and FIG. 4). The improved sensitivity of the optimized protocol led to the average detection of 2,372 more genes in each cell (p<0.05 Student's t-test; FIG. 2c). All these improvements were independently validated using an alternative RNA-Seq alignment and analyses strategy (FIG. 5). Moreover, both better sensitivity and lower variability in single-cell transcriptome data generated with Smart-Seq2 than for data available for Quartz-Seq were obtained (FIG. 6). Although the sequenced libraries had similar mappings characteristics as SMARTer libraries, a 7% increase in unmapped reads was noted (FIG. 7).

Figure 9:
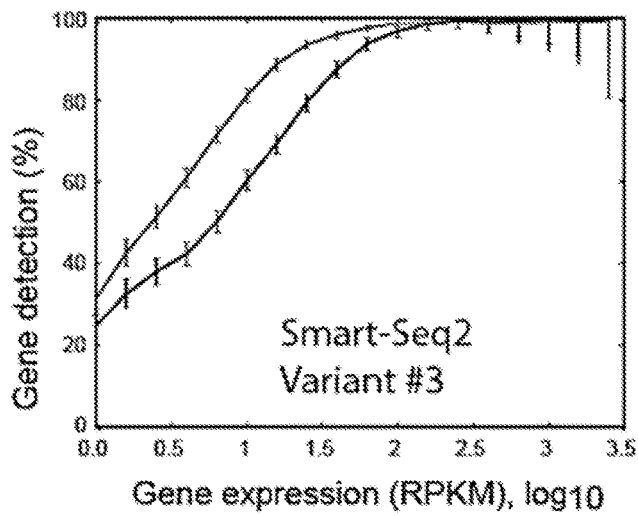
FIG. 9 illustrates single-cell RNA-Seq sensitivity and variability. (A) Percentage of genes reproducibly detected in replicate cells. (B) Standard deviation in gene expression estimates.
Figure 9:
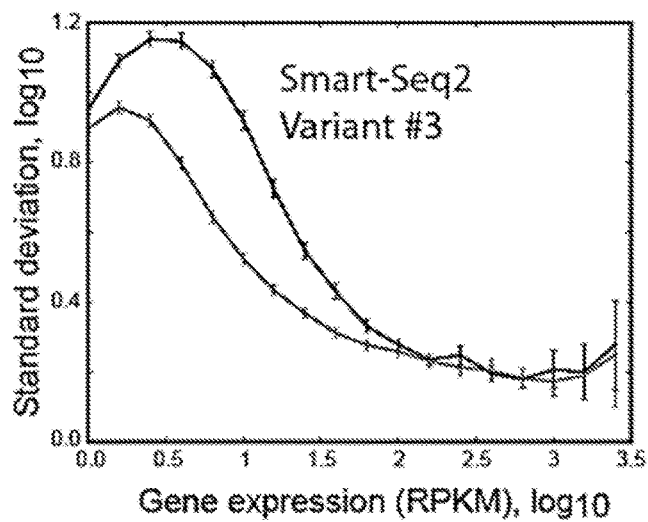
Figure 10:
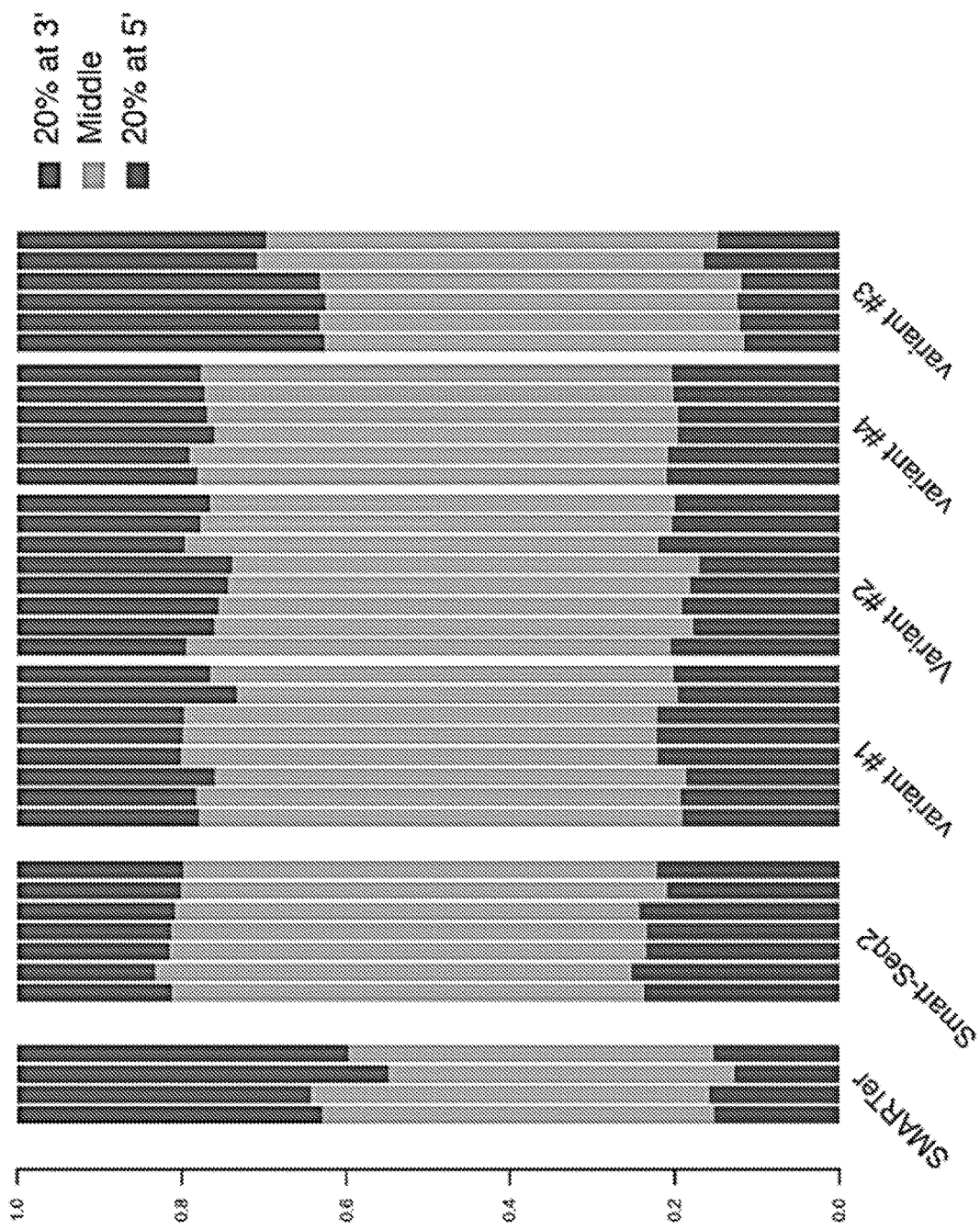
FIG. 10 illustrates read coverage across genes in single-cell RNA-Seq data.
Figure 11:
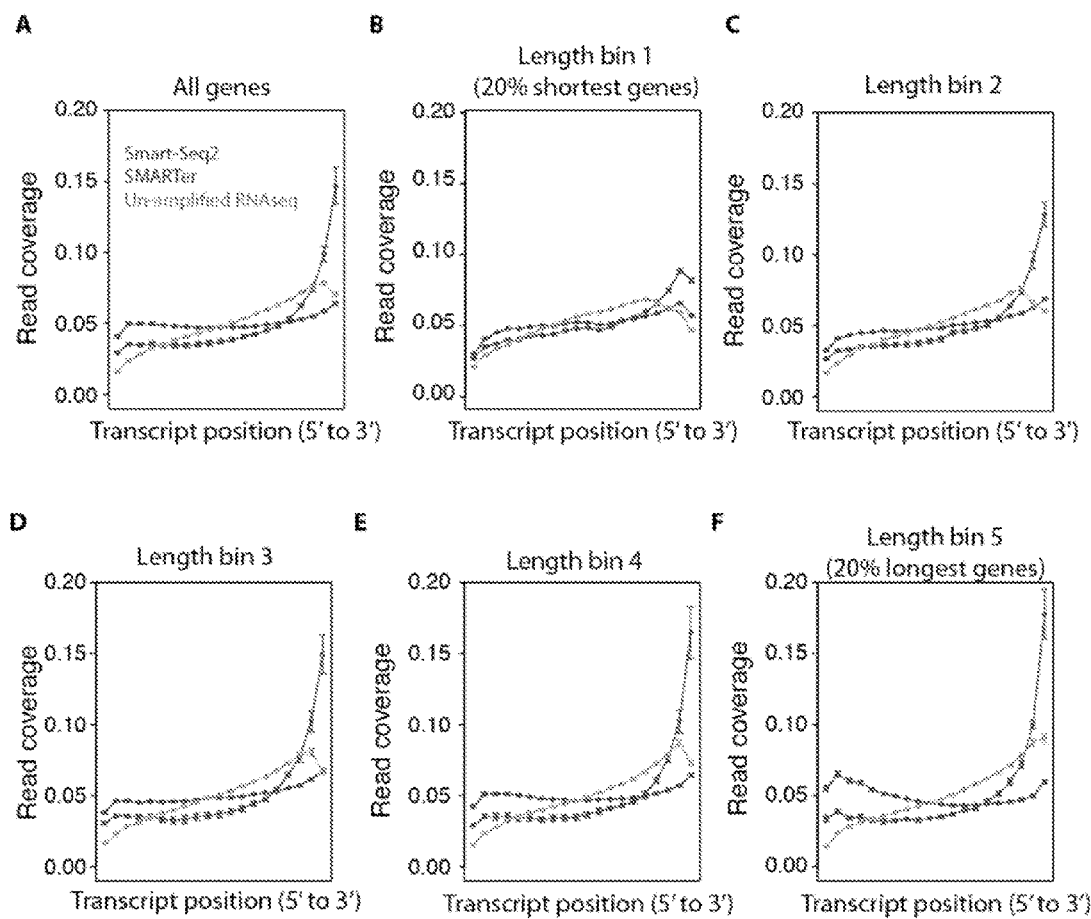
FIG. 11 illustrates read coverage across transcripts. (A) Mean fraction coverage read for all genes. (B)-(F) Transcripts grouped by length into 5 equal-sized bins.
Figure 12:
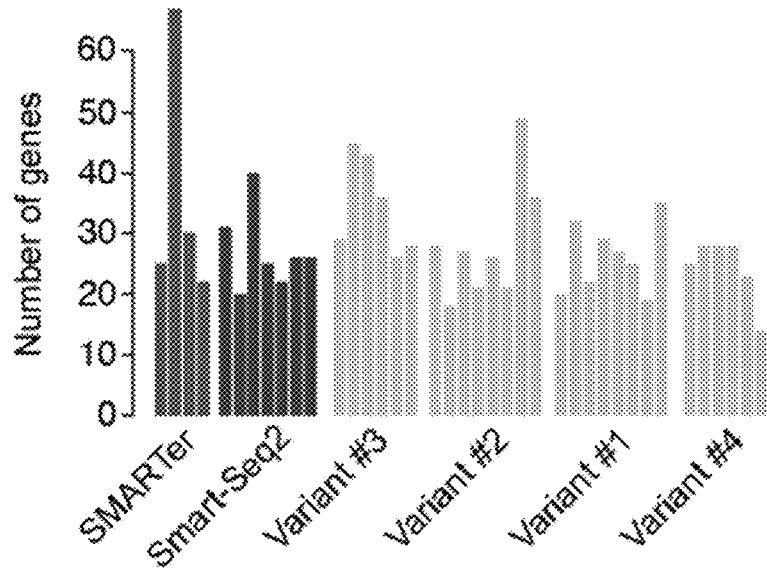
FIG. 12 illustrates read peaks in single-cell RNA-Seq data. (A) Number of genes with one or more high density peaks per single-cell RNA-Seq library. (B) Heatmaps of read densities across genes with peaks in the highest number of libraries.
Figure 12:
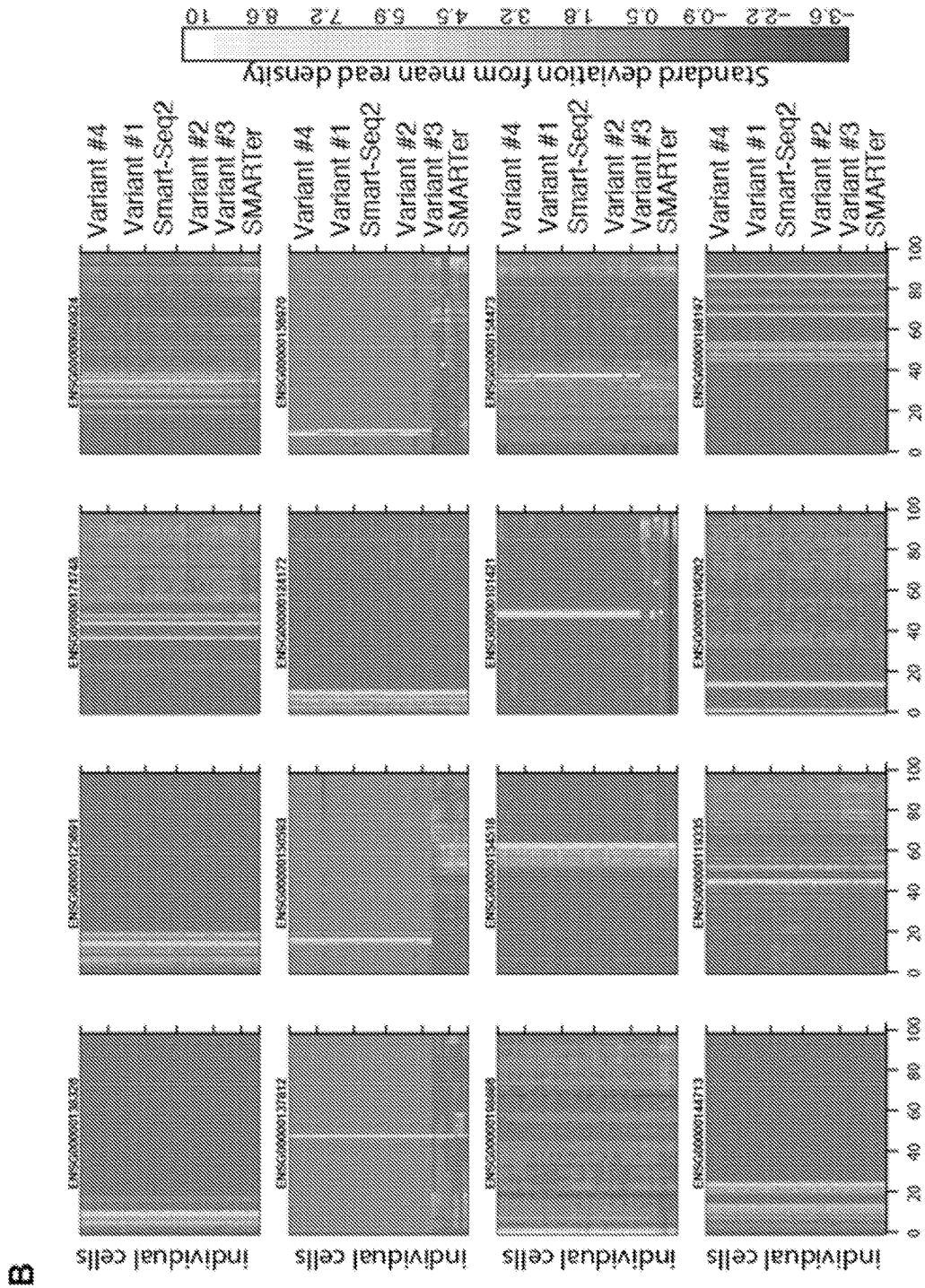

Several preamplification enzymes have lower GC bias than the Advantage2 (Adv2) that is used with SMARTer®, indicating that single-cell profiling could also improve with cDNA preamplifications using KAPA. Indeed, the single-cell libraries preamplified with KAPA detected more genes at higher GC levels (FIG. 2d and FIG. 8) and improved sensitivity and accuracy (FIG. 9). When compared with the low coverage of 5' regions in single-cell data generated through 3' end polyA-tailing of cDNA, single-cell RNA-Seq libraries that had been preamplified with KAPA had significantly better coverage across the full length of transcripts ($p<10^{-5}$, $1.6\times10^{-3}$ for 5' and 3' ends respectively, Student's t-test), as they approached the expected fraction of reads at the 5' and 3' ends (FIG. 2e and FIGS. 10-11). Importantly, global gene expression profiles from cells preamplified with KAPA and Adv2 separated on the first principal component (FIG. 2f), demonstrating that preamplification bias had significant impact on absolute expression levels. Regions with artificially large number of reads aligned (i.e. peak) appearing systematically in Smart-Seq irrespectively of preamplification enzyme that necessitated filtering were sequenced (FIG. 12). Together, the data show that preamplification using KAPA improved GC tolerance and read coverage across transcripts.

Figure 13:
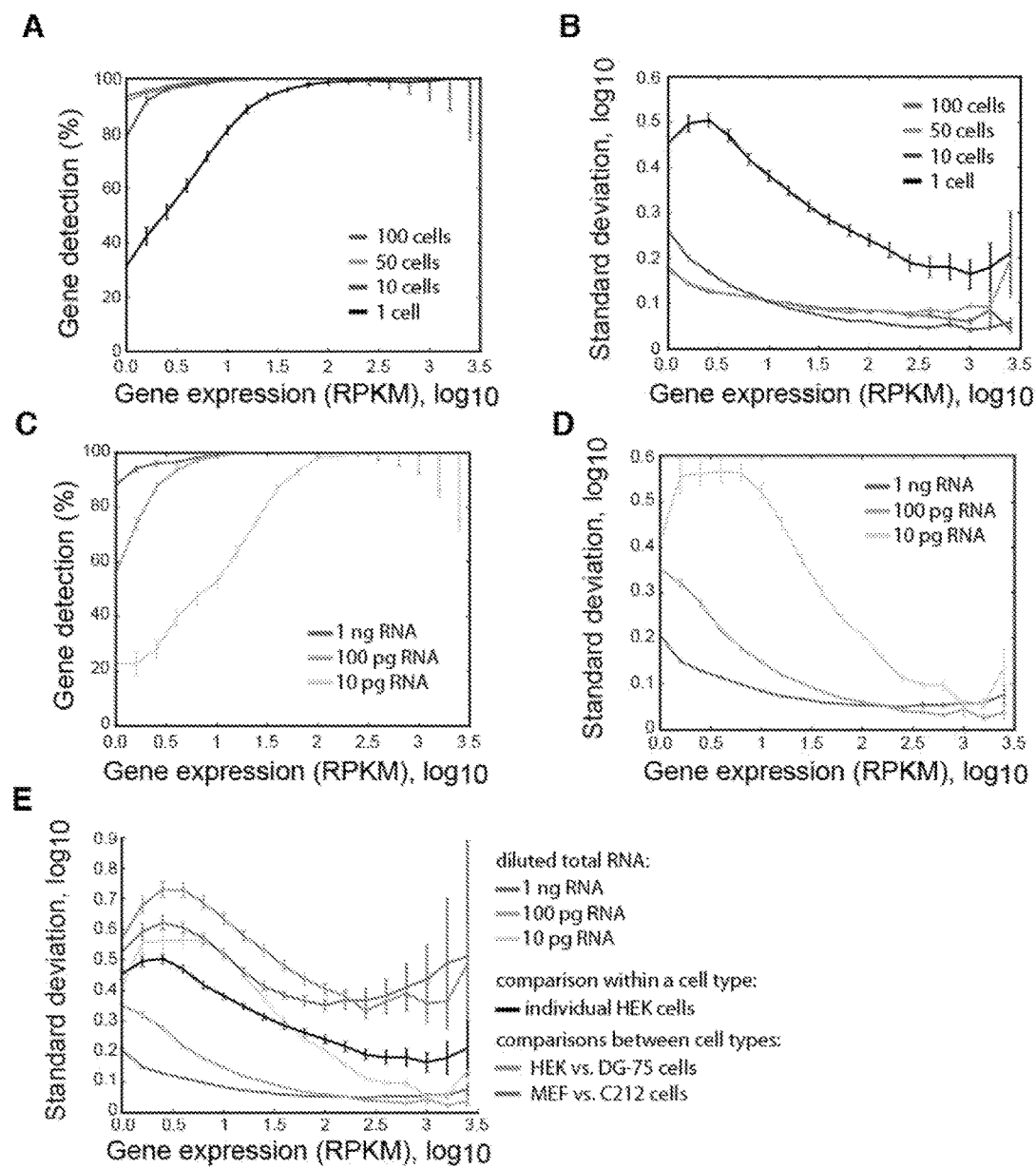
FIG. 13 illustrates assessment of the technical and biological variability in single-cell transcriptomics using Smart-Seq2. (A) Percentage of genes reproducibly detected in dilutions of HEK cells. (B) Standard deviation in gene expression estimates for (A). (C) Percentage of genes reproducibly detected in dilutions of HEK total RNA. (D) Standard deviation in gene expression estimates for (D). (E) Standard deviation in gene expression estimates for (D) with pair-wise comparisons of individual cells.

To determine the extent of technical variability in the single-cell transcriptome profiling with Smart-Seq2, sequencing libraries were generated from dilution series of HEK293T cells (100, 50 and 10 cells) and total RNA (1 ng, 100 pg, 10 pg). Technical losses and variations were small when analyzing 10 cells or more, but considerable variability exists at single-cell levels, as previously observed. It is informative to contrast the technical variability with the biological variability present in cells of the same or different cell type origin (FIG. 13A-D). To this end, additional single-cell transcriptomes were sequenced from DG-75 (n=7), C2C12 (n=6) and MEF (n=7) cells. Analyzing the biological variability between and within cell populations revealed that biological variability associated with cell type specific expression exceeded technical variability at around 50 RPKM, but the exact threshold will depend on the RNA content present in the cell types studied (FIG. 13E).

Figure 14:
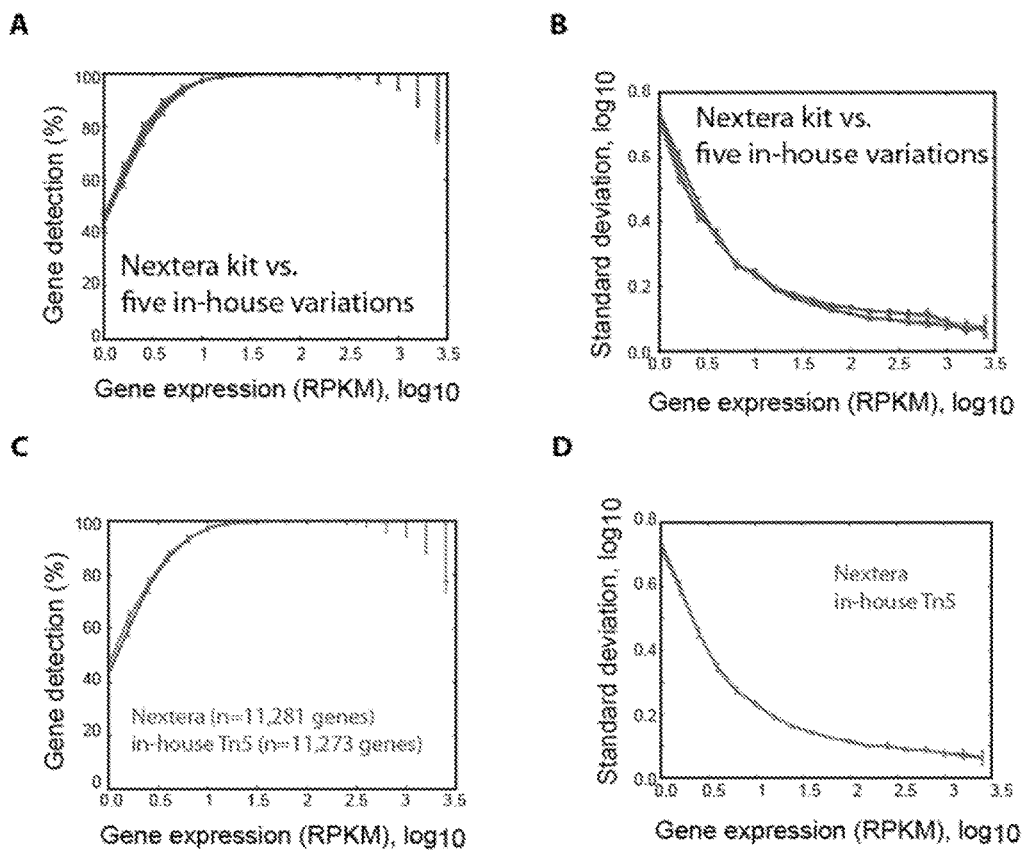
FIG. 14 illustrates comparison of libraries generated with commercial Tn5 (Nextera) to in-house produced Tn5. (A) Percentage of genes reproducibly detected using in-house conditions. (B) Standard deviation in gene expression estimates for (A). (C) Percentage of genes reproducibly detected using commercial buffers and conditions. (D) Standard deviation in gene expression estimates for (D). (E) Differences in reactions carried out in (A).

This invention provides a new protocol that improves sensitivity, accuracy and coverage across transcripts and is more amenable to automation. Moreover, the new protocol costs less than 12% of the current cost per reaction and only 3% when using in-house produced Tn5 (FIG. 14).

Although these results were reached in the context of Smart-Seq single-cell gene expression analyses, these modifications are applicable other single-cell methods that rely on template switching, including those carried out on microfluidic chips (e.g. Fluidigm C1) or inside emulsion droplets.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

All references cited herein are incorporated herein by reference in their entireties.

TABLE S1

Tables of cDNA library yield and length starting with purified total RNA

Worksheet A lists all 457 cDNA libraries generated from mouse brain total RNA. The general protocol followed for each sample is indicated in the "general protocol" column, with specific information on the template switching oligonucleotide, RT enzyme, PCR enzyme, MgCl2 concentration, betaine, bead purification and dNTPs administration timing detailed in separate columns. Worksheet B contains a list of direct comparisons of variables that effect cDNA library yield and average length using replicate groups that have identical reaction parameters except for the experimental variable evaluated.

| Entry | amount (ng) | PCR cycles | ul elution | dil. Bio-ana-lyzer | additional description | conc (pg/ul) | avg size (bp) | TSO | amount TSO (ul of 10 uM in 10 ul RT rxn) | RT enzyme | MgCl2 (mM) | RT protocol | betaine (M) | purification after RT | PCR enzyme | PCR rxn vol (ul) | dNTPs added in the beginning? | other additives |
|---|---|---|---|---|---|---|---|---|---|---|---|---|---|---|---|---|---|---|
| 1 | 1 | 15 | 10 | 1:5 | SMARTer kit | 318 | 1669 | SMARTer Oligo IIA | 1 | SMARTscribe | 6 | 90' @ 42° C. | — | yes | Advantage | 50 | — | — |
| 2 | 1 | 15 | 10 | 1:5 | SMARTer kit but replacing ISPCR primers | 263 | 1857 | SMARTer Oligo IIA | 1 | SMARTscribe | 6 | 90' @ 42° C. | — | yes | Advantage | 50 | — | — |
| 3 | 1 | 15 | 10 | 1:5 | SMARTer kit but replacing oligo dT | 172 | 1784 | SMARTer Oligo IIA | 1 | SMARTscribe | 6 | 90' @ 42° C. | — | yes | Advantage | 50 | — | — |
| 4 | 1 | 15 | 10 | 1:5 | SMARTer kit but replacing FSB | FAILED | | SMARTer Oligo IIA | 1 | SMARTscribe | 6 | 90' @ 42° C. | — | yes | Advantage | 50 | — | 3 mM MnCl2 |
| 5 | 1 | 15 | 10 | 1:5 | modified SMARTer kit | 393 | 1683 | SMARTer Oligo IIA | 1 | SSRTII | 6 | 90' @ 42° C. | — | yes | Advantage | 50 | — | — |
| 6 | 1 | 15 | NA | NA | modified SMARTer kit | 121 | 1780 | rG5 | 1 | SMARTscribe | 6 | 90' @ 42° C. | — | yes | Advantage | 50 | — | — |
| 7 | 1 | 15 | NA | NA | modified SMARTer kit | 1038 | 1346 | rGrGrG | 1 | SMARTscribe | 6 | 90' @ 42° C. | — | yes | Advantage | 50 | — | — |
| 8 | 1 | 15 | NA | NA | modified SMARTer kit | 90 | 1652 | rGrGrGp | 1 | SMARTscribe | 6 | 90' @ 42° C. | — | yes | Advantage | 50 | — | — |
| 9 | 1 | 15 | NA | NA | modified SMARTer kit | 84 | 1608 | ISO | 1 | SMARTscribe | 6 | 90' @ 42° C. | — | yes | Advantage | 50 | — | — |
| 10 | 1 | 15 | NA | NA | modified SMARTer kit | 3628 | 1838 | SMARTer Oligo IIA | 1 | SMARTscrib | 6 | 90' @ 42° C. | — | ye | Advantage | 50 | — | — |
| 11 | 1 | 15 | NA | NA | modified SMARTer kit | 650 | 2108 | rG5 | 1 | SMARTscribe | 6 | 90' @ 42° C. | — | yes | Advantage | 50 | — | — |
| 12 | 1 | 15 | NA | NA | modified SMARTer kit | 6423 | 1852 | rGrGrG | 1 | SMARTscribe | 6 | 90' @ 42° C. | — | yes | Advantage | 50 | — | — |
| 13 | 1 | 15 | NA | NA | modified SMARTer kit | 666 | 2187 | rGrGrGp | 1 | SMARTscribe | 6 | 90' @ 42° C. | — | yes | Advantage | 50 | — | — |
| 14 | 1 | 15 | NA | NA | modified SMARTer kit | 525 | 2181 | ISO | 1 | SMARTscribe | 6 | 90' @ 42° C. | — | yes | Advantage | 50 | — | — |

TABLE S1-continued

Tables of cDNA library yield and length starting with purified total RNA

| | | | | | | | | | | | | | | | | |
|---|---|---|---|---|---|---|---|---|---|---|---|---|---|---|---|---|
| 15 | 1 | 15 | NA | SMARTer kit but replacing ISPCR primers | 3366 | 1782 | SMARTer Oligo IIA | 1 | SMARTscribe | 6 | 90' @ 42° C. | — | yes | Advantage | 50 | — | — |
| 16 | 1 | 15 | NA | modified SMARTer kit | 435 | 1970 | ds oligos | 1 | SMARTscribe | 6 | 90' @ 42° C. | — | yes | Advantage | 50 | — | — |
| 17 | 1 | 15 | NA | SMARTer kit | 1143 | 1445 | SMARTer Oligo IIA | 1 | SMARTscribe | 6 | 90' @ 42° C. | — | yes | Advantage | 50 | — | — |
| 18 | 1 | 15 | NA | SMARTer kit but replacing ISPCR primers | 1504 | 1519 | SMARTer Oligo IIA | 1 | SMARTscribe | 6 | 90' @ 42° C. | — | yes | Advantage | 50 | — | — |
| 19 | 1 | 15 | NA | SMARTer kit but replacing ISPCR primers | 1984 | 1728 | SMARTer Oligo IIA | 1 | SMARTscribe | 6 | 90' @ 42° C. | — | yes | Advantage | 50 | — | — |
| 20 | 1 | 15 | NA | modified SMARTer kit | 1346 | 1543 | SMARTer Oligo IIA | 1 | SSRTIII | 6 | 90' @ 42° C. | — | yes | Advantage | 50 | — | — |
| 21 | 1 | 15 | NA | modified SMARTer kit | 1191 | 1683 | SMARTer Oligo IIA | 1 | SSRTIII | 6 | 90' @ 42° C. | — | yes | Advantage | 50 | — | — |
| 22 | 1 | 15 | NA | SMARTer kit but using Superscript II FSB (3 mM MgCl2) | 103 | 1420 | SMARTer Oligo IIA | 1 | SMARTscribe | 3 | 90' @ 42° C. | — | yes | Advantage | 50 | — | — |
| 23 | 1 | 15 | NA | SMARTer kit but using Superscript II FSB (3 mM MgCl2) | 192 | 1609 | SMARTer Oligo IIA | 1 | SMARTscribe | 3 | 90' @ 42° C. | — | yes | Advantage | 50 | — | — |
| 24 | 1 | 15 | NA | SMARTer kit but using STRT buffer | FAILED | | SMARTer Oligo IIA | 1 | SMARTscribe | — | 90' @ 42° C. | — | yes | Advantage | 50 | — | 6 mM MnCl2 |
| 25 | 1 | 15 | NA | SMARTer kit | 1573 | 2378 | SMARTer Oligo IIA | 1 | SMARTscribe | 6 | 90' @ 42° C. | — | yes | Advantage | 50 | — | — |
| 26 | 1 | 15 | NA | modified SMARTer kit | 246 | 2024 | rG5 | 1 | SMARTscribe | 3 | 90' @ 42° C. | — | yes | Advantage | 50 | — | — |
| 27 | 1 | 15 | NA | modified SMARTer kit | 1393 | 1945 | rGrGrG | 1 | SMARTscribe | 3 | 90' @ 42° C. | — | yes | Advantage | 50 | — | — |
| 28 | 1 | 15 | NA | modified SMARTer kit | 259 | 2180 | rGrGrGp | 1 | SMARTscribe | 3 | 90' @ 42° C. | — | yes | Advantage | 50 | — | — |
| 29 | 1 | 15 | NA | modified SMARTer kit | 776 | 1958 | SMARTer Oligo IIA | 1 | SMARTscribe | 6 | 90' @ 42° C. | 1 | yes | Advantage | 50 | — | — |
| 30 | 1 | 15 | NA | modified SMARTer kit | 731 | 1808 | SMARTer Oligo IIA | 1 | SMARTscribe | 6 | 90' @ 42° C. | 2 | yes | Advantage | 50 | — | — |
| 31 | 1 | 15 | NA | modified SMARTer kit | 1936 | 1965 | SMARTer Oligo IIA | 1 | SMARTscribe | 6 | 90' @ 42° C. | 1 | yes | Advantage | 50 | — | — |

TABLE S1-continued

Tables of cDNA library yield and length starting with purified total RNA

| # | | | | | | | | | | | | | | | |
|---|---|---|---|---|---|---|---|---|---|---|---|---|---|---|---|
| 32 | 1 | 15 | NA | modified SMARTer kit | FAILED | SMARTer Oligo IIA | 1 | SMARTscribe | 6 | 90' @ 42° C. | 1 | yes | Advantage | 50 | — | 3 mM MnCl2 |
| 33 | 1 | 15 | NA | modified SMARTer kit | FAILED | SMARTer Oligo IIA | 1 | SMARTscribe | 6 | 90' @ 42° C. | — | yes | Advantage | 50 | — | 3 mM MnCl2, 5% DMSO |
| 34 | 1 | 15 | NA | SMARTer kit | 580 | SMARTer Oligo IIA | 1 | SMARTscribe | 6 | 90' @ 42° C. | 1 | yes | Advantage | 50 | — | |
| 35 | 1 | 15 | NA | modified SMARTer kit | 166 | SMARTer Oligo IIA | 1 | SMARTscribe | 3 | 90' @ 42° C. | 1 | yes | Advantage | 50 | — | |
| 36 | 1 | 15 | NA | modified SMARTer kit | 204 | SMARTer Oligo IIA | 1 | SMARTscribe | 3 | 90' @ 42° C. | 1 | yes | Advantage | 50 | — | |
| 37 | 1 | 15 | NA | modified SMARTer kit | 547 | SMARTer Oligo IIA | 1 | SMARTscribe | 6 | 90' @ 42° C. | 1 | yes | Advantage | 50 | — | |
| 38 | 1 | 15 | NA | modified SMARTer kit | 640 | SMARTer Oligo IIA | 1 | SMARTscribe | 6 | 90' @ 42° C. | 1 | yes | Advantage | 50 | — | |
| 39 | 1 | 15 | NA | modified SMARTer kit | 145 | rGrGrG | 1 | SMARTscribe | 3 | 90' @ 42° C. | 1 | yes | Advantage | 50 | — | |
| 40 | 1 | 15 | NA | modified SMARTer kit | 224 | rGrGrG | 1 | SMARTscribe | 3 | 90' @ 42° C. | 1 | yes | Advantage | 50 | — | |
| 41 | 1 | 15 | NA | modified SMARTer kit | 496 | rGrGrG | 1 | SMARTscribe | 6 | 90' @ 42° C. | 1 | yes | Advantage | 50 | — | |
| 42 | 1 | 15 | NA | modified SMARTer kit | 493 | rGrGrG | 1 | SMARTscribe | 6 | 90' @ 42° C. | 1 | yes | Advantage | 50 | — | |
| 43 | 1 | 15 | 20 | in house prot | 8431 | rGrGrG | 1 | SSRTII | 6 | 90' @ 42° C. | 1 | yes | Advantage | 50 | — | |
| 44 | 1 | 15 | 20 | in house prot | 8248 | rGrGrG | 1 | SSRTII | 6 | 90' @ 42° C. | 1 | yes | Advantage | 50 | — | |
| 45 | 1 | 15 | 20 | in house prot | 7672 | rGrGrG | 1 | SSRTII | 6 | 90' @ 42° C. | 1.5 | yes | Advantage | 50 | — | |
| 46 | 1 | 15 | 20 | in house prot | 6562 | rGrGrG | 1 | SSRTII | 6 | 90' @ 42° C. | 1.5 | yes | Advantage | 50 | — | |
| 47 | 1 | 15 | 20 | SMARTer kit | 8156 | SMARTer Oligo IIA | 1 | SMARTscribe | 6 | 90' @ 42° C. | — | yes | Advantage | 50 | — | |
| 48 | 1 | 15 | 20 | in house prot | 1744 | rGrGrGp | 1 | SSRTII | 6 | 90' @ 42° C. | 1 | yes | Advantage | 50 | — | |
| 49 | 1 | 15 | 20 | in house prot | 1820 | rGrGrGp | 1 | SSRTII | 6 | 90' @ 42° C. | 1 | yes | Advantage | 50 | — | |
| 50 | 1 | 15 | 20 | in house prot | 1591 | rGrGrGp | 1 | SSRTII | 6 | 90' @ 42° C. | 1.5 | yes | Advantage | 50 | — | |
| 51 | 1 | 15 | 20 | in house prot | 1398 | rGrGrGp | 1 | SSRTII | 6 | 90' @ 42° C. | 1.5 | yes | Advantage | 50 | — | |
| 52 | 1 | 15 | 20 | in house prot | 2265 | dGCGGG | 1 | SSRTII | 6 | 90' @ 42° C. | 1 | yes | Advantage | 50 | — | |
| 53 | 1 | 15 | 20 | in house prot | 2568 | dGCGGG | 1 | SSRTII | 6 | 90' @ 42° C. | 1 | yes | Advantage | 50 | — | |
| 54 | 1 | 15 | 20 | in house prot | 2263 | dGCGGG | 1 | SSRTII | 6 | 90' @ 42° C. | 1 | yes | Advantage | 50 | — | |
| 55 | 1 | 15 | 20 | in house prot | 691 | dGCGGGp | 1 | SSRTII | 6 | 90' @ 42° C. | 1 | yes | Advantage | 50 | — | |

TABLE S1-continued

Tables of cDNA library yield and length starting with purified total RNA

| | | | | | | | | | | | | | | | | | |
|---|---|---|---|---|---|---|---|---|---|---|---|---|---|---|---|---|---|
| 56 | 1 | 15 | 20 | in house prot | — | 757 | 2344 | dGCGGGp | 1 | SSRTIII | 6 | 90' @ 42° C. | 1 | yes | Advantage | 50 | — |
| 57 | 1 | 15 | 20 | in house prot | — | 690 | 2294 | dGCGGGp | 1 | SSRTIII | 6 | 90' @ 42° C. | 1 | yes | Advantage | 50 | — |
| 58 | 1 | 15 | 20 | SMARTer kit | — | 6525 | 2295 | SMARTer Oligo IIA | 1 | SMARTscribe | 6 | 90' @ 42° C. | — | yes | Advantage | 50 | — |
| 59 | 1 | 15 | 20 | SMARTer kit | — | 6806 | 2270 | SMARTer Oligo IIA | 1 | SMARTscribe | 6 | 90' @ 42° C. | — | yes | Advantage | 50 | — |
| 60 | 1 | 15 | 20 | in house prot, processed immediately after adding lysis buffer (LB) | — | 5922 | 1861 | rGrGrG | 1 | SSRTIII | 6 | 90' @ 42° C. | 1 | yes | Advantage | 50 | — |
| 61 | 1 | 15 | 20 | in house prot, processed immediately after adding lysis buffer (LB) | — | 5419 | 1892 | rGrGrG | 1 | SSRTIII | 6 | 90' @ 42° C. | 1 | yes | Advantage | 50 | — |
| 62 | 1 | 15 | 20 | in house prot, processed immediately after adding lysis buffer (LB), 60' after adding lysis buffer (LB), stored at RT | — | 5664 | 1806 | rGrGrG | 1 | SSRTIII | 6 | 90' @ 42° C. | 1 | yes | Advantage | 50 | — |
| 63 | 1 | 15 | 20 | in house prot, processed immediately after adding lysis buffer (LB), 45' after adding lysis buffer (LB), stored at RT | — | 5554 | 1800 | rGrGrG | 1 | SSRTIII | 6 | 90' @ 42° C. | 1 | yes | Advantage | 50 | — |
| 64 | 1 | 15 | 20 | in house prot, processed immediately after adding lysis buffer (LB), 30' after adding lysis buffer (LB), stored at RT | — | 5552 | 1772 | rGrGrG | 1 | SSRTIII | 6 | 90' @ 42° C. | 1 | yes | Advantage | 50 | — |

TABLE S1-continued

Tables of cDNA library yield and length starting with purified total RNA

| | | | | | | | | | | | | | |
|---|---|---|---|---|---|---|---|---|---|---|---|---|---|
| 65 | 1 | 15 | 20 | in house prot, processed immediately after adding lysis buffer (LB), 10' after adding lysis buffer (LB), stored at RT | — | 6335 | 1824 rGrGrG | 1 | SSRTII | 6 | 90' @ 42° C. | 1 | yes | Advantage | 50 | — |
| 66 | 1 | 15 | 20 | in house prot, processed immediately after adding lysis buffer (LB), 60' after adding lysis buffer (LB), stored in the fridge | — | 4904 | 1700 rGrGrG | 1 | SSRTII | 6 | 90' @ 42° C. | 1 | yes | Advantage | 50 | — |
| 67 | 1 | 15 | 20 | in house prot, processed immediately after adding lysis buffer (LB), 45' after adding lysis buffer (LB), stored in the fridge | — | 3938 | 1544 rGrGrG | 1 | SSRTII | 6 | 90' @ 42° C. | 1 | yes | Advantage | 50 | — |
| 68 | 1 | 15 | 20 | in house prot, processed immediately after adding lysis buffer (LB), 30' after adding lysis buffer (LB), stored in the fridge | — | 3793 | 1585 rGrGrG | 1 | SSRTII | 6 | 90' @ 42° C. | 1 | yes | Advantage | 50 | — |
| 69 | 1 | 15 | 20 | in house prot, processed immediately after adding lysis buffer (LB), 10' after adding lysis buffer (LB), stored in the fridge | — | 5312 | 1824 rGrGrG | 1 | SSRTII | 6 | 90' @ 42° C. | 1 | yes | Advantage | 50 | — |

TABLE S1-continued

Tables of cDNA library yield and length starting with purified total RNA

| # | | | | | | | | | | | | | | | | | |
|---|---|---|---|---|---|---|---|---|---|---|---|---|---|---|---|---|---|
| 70 | 1 | 15 | 30 | — | in house prot, RT for 1 h @42° C., then added 3 mM MnCl2 and incubated for 15' | 1024 | 1547 rGrGrG | 1 | SSRTIII | 6 | 90' @ 42° C. | 1 | yes | Advantage | 50 | — | 3 mM MnCl2 |
| 71 | 1 | 15 | 30 | — | in house prot, RT for 1 h @42° C., then added 3 mM MnCl2 and incubated for 15' | 849 | 1412 rGrGrG | 1 | SSRTIII | 6 | 90' @ 42° C. | 1 | yes | Advantage | 50 | — | 3 mM MnCl2 |
| 72 | 1 | 15 | 30 | — | in house prot, RT for 1 h @42° C., then added 6 mM MnCl2 and incubated for 15' | 558 | 1227 rGrGrG | 1 | SSRTIII | 6 | 90' @ 42° C. | 1 | yes | Advantage | 50 | — | 6 mM MnCl2 |
| 73 | 1 | 15 | 30 | — | in house prot, RT for 1 h @42° C., then added 6 mM MnCl2 and incubated for 15' | 572 | 1199 rGrGrG | 1 | SSRTIII | 6 | 90' @ 42° C. | 1 | yes | Advantage | 50 | — | 6 mM MnCl2 |
| 74 | 1 | 15 | 30 | — | in house prot | 2105 | 2051 rGrGrG | 1 | SSRTIII | 6 | 90' @ 42° C. | 1 | yes | Advantage | 50 | — | — |
| 75 | 1 | 15 | 30 | — | in house prot | 1664 | 1809 rGrGrG | 1 | SSRTIII | 6 | 90' @ 42° C. | 1 | yes | Advantage | 50 | — | — |
| 76 | 100 | 10 | 15 | 1:5 | in house prot | 3196 | 1946 2OMe | 1 | SSRTIII | 6 | 90' @ 42° C. | 1 | yes | Advantage | 50 | — | — |
| 77 | 100 | 10 | 15 | 1:5 | in house prot | 8894 | 1767 rGrG + G | 1 | SSRTIII | 6 | 90' @ 42° C. | 1 | yes | Advantage | 50 | — | — |
| 78 | 100 | 10 | 15 | 1:5 | in house prot | 1939 | 2054 ddC | 1 | SSRTIII | 6 | 90' @ 42° C. | 1 | yes | Advantage | 50 | — | — |
| 79 | 100 | 10 | 15 | 1:5 | in house prot | 1942 | 1286 rGrGrG | 1 | SSRTIII | 6 | 90' @ 42° C. | 1 | yes | Advantage | 50 | — | — |
| 80 | 10 | 12 | 15 | 1:5 | in house prot | 1635 | 1891 2OMe | 1 | SSRTIII | 6 | 90' @ 42° C. | 1 | yes | Advantage | 50 | — | — |
| 81 | 10 | 12 | 15 | 1:5 | in house prot | 1230 | 1705 2OMe | 1 | SSRTIII | 6 | 90' @ 42° C. | 1 | yes | Advantage | 50 | — | — |
| 82 | 10 | 12 | 15 | 1:5 | in house prot | 4700 | 1602 rGrG + G | 1 | SSRTIII | 6 | 90' @ 42° C. | 1 | yes | Advantage | 50 | — | — |
| 83 | 10 | 12 | 15 | 1:5 | in house prot | 4051 | 1717 rGrG + G | 1 | SSRTIII | 6 | 90' @ 42° C. | 1 | yes | Advantage | 50 | — | — |
| 84 | 10 | 12 | 15 | 1:5 | in house prot | 733 | 1904 ddC | 1 | SSRTIII | 6 | 90' @ 42° C. | 1 | yes | Advantage | 50 | — | — |

TABLE S1-continued

Tables of cDNA library yield and length starting with purified total RNA

| | | | | | | | | | | | |
|---|---|---|---|---|---|---|---|---|---|---|---|
| 85 | 10 | 12 | 15 | 1:5 | in house prot | 637 | 1897 ddC | 1 | SSRIII | 6 | 90' @ 42° C. | 1 | yes | Advantage | 50 | — |
| 86 | 10 | 12 | 15 | 1:5 | in house prot | 1104 | 1556 rGrGrG | 1 | SSRIII | 6 | 90' @ 42° C. | 1 | yes | Advantage | 50 | — |
| 87 | 1 | 15 | 15 | 1:5 | in house prot | 923 | 1734 2OMe | 1 | SSRIII | 6 | 90' @ 42° C. | 1 | yes | Advantage | 50 | — |
| 88 | 1 | 15 | 15 | 1:5 | in house prot | 842 | 1620 2OMe | 1 | SSRIII | 6 | 90' @ 42° C. | 1 | yes | Advantage | 50 | — |
| 89 | 1 | 15 | 15 | 1:5 | in house prot | 3387 | 1426 rGrG + G | 1 | SSRIII | 6 | 90' @ 42° C. | 1 | yes | Advantage | 50 | — |
| 90 | 1 | 15 | 15 | 1:5 | in house prot | 3609 | 1473 rGrG + G | 1 | SSRIII | 6 | 90' @ 42° C. | 1 | yes | Advantage | 50 | — |
| 91 | 1 | 15 | 15 | 1:5 | in house prot | 401 | 1463 ddC | 1 | SSRIII | 6 | 90' @ 42° C. | 1 | yes | Advantage | 50 | — |
| 92 | 1 | 15 | 15 | 1:5 | in house prot | 470 | 1661 ddC | 1 | SSRIII | 6 | 90' @ 42° C. | 1 | yes | Advantage | 50 | — |
| 93 | 1 | 15 | 15 | 1:5 | in house prot | 1550 | 1341 rGrGrG | 1 | SSRIII | 6 | 90' @ 42° C. | 1 | yes | Advantage | 50 | — |
| 94 | 1 | 15 | 15 | 1:5 | in house prot | 1267 | 1483 rGrGrG | 1 | SSRIII | 6 | 90' @ 42° C. | 1 | yes | Advantage | 50 | — |
| 95 | 1 | 15 | 15 | 1:5 | in house prot | 2176 | 1438 rGrG + G | 1 | SSRIII | 6 | 90' @ 42° C. | 1 | yes | Advantage | 50 | — |
| 96 | 1 | 15 | 15 | 1:5 | in house prot | 1469 | 1705 rGrGrG | 1 | SSRIII | 9 | 90' @ 42° C. | 1 | yes | Advantage | 50 | — |
| 97 | 1 | 15 | 15 | 1:5 | in house prot | 2383 | 1596 rGrG + G | 1 | SSRIII | 9 | 90' @ 42° C. | 1 | yes | Advantage | 50 | — |
| 98 | 1 | 15 | 15 | 1:5 | in house prot | 1431 | 1807 rGrGrG | 1 | SSRIII | 12 | 90' @ 42° C. | 1 | yes | Advantage | 50 | — |
| 99 | 1 | 15 | 15 | 1:5 | in house prot | 3630 | 1623 rGrG + G | 1 | SSRIII | 12 | 90' @ 42° C. | 1 | yes | Advantage | 50 | — |
| 100 | 1 | 15 | 15 | 1:5 | in house prot | 1277 | 1610 rGrGrG | 1 | SSRIII | 15 | 90' @ 42° C. | 1 | yes | Advantage | 50 | — |
| 101 | 1 | 15 | 15 | 1:5 | in house prot | 1884 | 1462 rGrG + G | 1 | SSRIII | 15 | 90' @ 42° C. | 1 | yes | Advantage | 50 | — |
| 102 | 1 | 15 | 15 | 1:5 | in house prot | 1123 | 1652 SMARTer Oligo IIA | 1 | SSRIII | 6 | 90' @ 42° C. | 1 | yes | Advantage | 50 | — |
| 103 | 1 | 15 | 15 | 1:5 | in house prot | 935 | 1593 SMARTer Oligo IIA | 1 | SSRIII | 15 | 90' @ 42° C. | 1 | yes | Advantage | 50 | — |
| 104 | 1 | 15 | 15 | 1:5 | in house prot, KAPA HiFi after washing beads 1 | 2156 | 1767 rGrG + G | 1 | SSRIII | 12 | 90' @ 42° C. | 1 | yes | KAPA HiFi HS | 50 | — |
| 105 | 1 | 15 | 15 | 1:5 | in house prot, KAPA HiFi after washing beads 1 | 352 | 2151 rGrGrG | 1 | SSRIII | 12 | 90' @ 42° C. | 1 | yes | KAPA HiFi HS | 50 | — |
| 106 | 1 | 15 | 15 | 1:5 | in house prot, KAPA HiFi after washing beads 2 | 1729 | 1611 rGrG + G | 1 | SSRIII | 12 | 90' @ 42° C. | 1 | yes | KAPA HiFi HS | 50 | — |

TABLE S1-continued

Tables of cDNA library yield and length starting with purified total RNA

| | | | | | | | | | | | | | |
|---|---|---|---|---|---|---|---|---|---|---|---|---|---|
| 107 | 1 | 15 | 15 | 1:5 | in house prot, KAPA HiFi after washing beads 2 | 203 | 2073 | rGrGrG | 1 | SSRTIII | 12 | 90' @ 42° C. | 1 | yes | KAPA HiFi HS | 50 | — |
| 108 | 1 | 15 | 15 | 1:5 | in house prot, KAPA HiFi after washing beads 1 + elution | 1108 | 1480 | rGrG + G | 1 | SSRTIII | 12 | 90' @ 42° C. | 1 | yes | KAPA HiFi HS | 50 | — |
| 109 | 1 | 15 | 15 | 1:5 | in house prot, KAPA HiFi after washing beads 1 + elution | 301 | 1903 | rGrGrG | 1 | SSRTIII | 12 | 90' @ 42° C. | 1 | yes | KAPA HiFi HS | 50 | — |
| 110 | 1 | 15 | 15 | 1:5 | in house prot, KAPA HiFi after washing beads 2 + elution | 1337 | 1522 | rGrG + G | 1 | SSRTIII | 12 | 90' @ 42° C. | 1 | yes | KAPA HiFi HS | 50 | — |
| 112 | 1 | 15 | 15 | 1:5 | in house prot, KAPA HiFi after washing beads 2 + elution | 383 | 1935 | rGrGrG | 1 | SSRTIII | 12 | 90' @ 42° C. | 1 | yes | KAPA HiFi HS | 50 | — |
| 113 | 1 | 15 | 15 | 1:5 | in house prot | 2897 | 1737 | rGrG + G | 1 | SSRTIII | 12 | 90' @ 42° C. | 1 | yes | Advantage | 50 | — |
| 114 | 1 | 15 | 15 | 1:5 | in house prot | 1853 | 1706 | rGrGrG | 1 | SSRTIII | 12 | 90' @ 42° C. | 1 | yes | Advantage | 50 | — |
| 115 | 1 | 15 | 15 | 1:5 | in house prot | 1492 | 1563 | rGrG + G | 1 | Revertaid H- | 4 | 90' @ 42° C. | 1 | yes | Advantage | 50 | — |
| 116 | 1 | 15 | 15 | 1:5 | in house prot | 1236 | 1472 | rGrG + G | 1 | Revertaid H- | 4 | 90' @ 42° C. | 1 | yes | Advantage | 50 | — |
| 117 | 1 | 15 | 15 | 1:5 | in house prot | 1843 | 1450 | rGrG + G | 1 | Revertaid H- | 6 | 90' @ 42° C. | 1 | yes | Advantage | 50 | — |
| 118 | 1 | 15 | 15 | 1:5 | in house prot | 1465 | 1346 | rGrG + G | 1 | Revertaid H- | 6 | 90' @ 42° C. | 1 | yes | Advantage | 50 | — |
| 119 | 1 | 15 | 15 | 1:5 | in house prot | 2996 | 1597 | rGrG + G | 1 | Revertaid H- | 9 | 90' @ 42° C. | 1 | yes | Advantage | 50 | — |
| 120 | 1 | 15 | 15 | 1:5 | in house prot | 2654 | 1530 | rGrG + G | 1 | Revertaid H- | 9 | 90' @ 42° C. | 1 | yes | Advantage | 50 | — |
| 121 | 1 | 15 | 15 | 1:5 | in house prot | 2159 | 1487 | rGrG + G | 1 | Revertaid H- | 12 | 90' @ 42° C. | 1 | yes | Advantage | 50 | — |
| 122 | 1 | 15 | 15 | 1:5 | in house prot | 1890 | 1412 | rGrG + G | 1 | Revertaid H- | 12 | 90' @ 42° C. | 1 | yes | Advantage | 50 | — |
| 123 | 1 | 15 | 15 | 1:5 | in house prot | 1504 | 1246 | rGrG + G | 1 | Revertaid H- | 15 | 90' @ 42° C. | 1 | yes | Advantage | 50 | — |
| 124 | 1 | 15 | 15 | 1:5 | in house prot | 1986 | 1474 | rGrG + G | 1 | Revertaid H- | 15 | 90' @ 42° C. | 1 | yes | Advantage | 50 | — |

TABLE S1-continued

Tables of cDNA library yield and length starting with purified total RNA

| | | | | | | | | | | | | | | |
|---|---|---|---|---|---|---|---|---|---|---|---|---|---|---|
| 125 | 1 | 15 | 15 | 1:5 | in house prot | 1109 | 1691 rGrG + G | 1 | SSRTIII | — | 60' @42° C., then 90' @60° C. | — | yes | — | Advantage | 50 | — | 0.3M trehalose |
| 126 | 1 | 15 | 15 | 1:5 | in house prot | 1090 | 1752 rGrG + G | 1 | SSRTIII | — | 60' @42° C., then 90' @60° C. | — | yes | — | Advantage | 50 | — | 0.3M trehalose |
| 127 | 1 | 15 | 15 | 1:5 | in house prot | 863 | 1565 rGrG + G | 1 | SSRTIII | — | 60' @42° C., then 90' @60° C. | — | yes | — | Advantage | 50 | — | 0.6M trehalose |
| 128 | 1 | 15 | 15 | 1:5 | in house prot | 896 | 1652 rGrG + G | 1 | SSRTIII | — | 60' @42° C., then 90' @60° C. | — | yes | — | Advantage | 50 | — | 0.6M trehalose |
| 129 | 1 | 15 | 15 | 1:5 | in house prot | 1078 | 1655 rGrG + G | 1 | SSRTIII | — | 60' @42° C., then 90' @60° C. | 1 | yes | — | Advantage | 50 | — | 0.3M trehalose |
| 130 | 1 | 15 | 15 | 1:5 | in house prot | 562 | 1517 rGrG + G | 1 | SSRTIII | — | 60' @42° C., then 90' @60° C. | 1 | yes | — | Advantage | 50 | — | 0.3M trehalose |
| 131 | 1 | 15 | 15 | 1:5 | in house prot | 998 | 1594 rGrG + G | 1 | SSRTIII | — | 60' @42° C., then 90' @60° C. | 0.6 | yes | — | Advantage | 50 | — | 0.3M trehalose |
| 132 | 1 | 15 | 15 | 1:5 | in house prot | 925 | 1545 rGrG + G | 1 | SSRTIII | — | 60' @42° C., then 90' @60° C. | 0.6 | yes | — | Advantage | 50 | — | 0.3M trehalose |
| 133 | 1 | 15 | 15 | 1:5 | in house prot | 1155 | 1618 rGrG + G | 1 | SSRTIII | — | 60' @42° C., then 90' @60° C. | 1 | yes | — | Advantage | 50 | — | 0.3M trehalose |
| 134 | 1 | 15 | 15 | 1:5 | in house prot | 603 | 1433 rGrG + G | 1 | SSRTIII | 3 | 60' @42° C., then 90' @60° C. | 1 | yes | — | Advantage | 50 | — | 0.3M trehalose |
| 135 | 1 | 15 | 15 | 1:5 | in house prot | 1561 | 1716 rGrG + G | 1 | SSRTIII | 3 | 60' @42° C., then 90' @60° C. | 0.6 | yes | — | Advantage | 50 | — | 0.3M trehalose |
| 136 | 1 | 15 | 15 | 1:5 | in house prot | 445 | 1575 rGrG + G | 1 | SSRTIII | 3 | 60' @50° C., then 90' @42° C. | — | yes | — | Advantage | 50 | — | 0.3M trehalose |

TABLE S1-continued

Tables of cDNA library yield and length starting with purified total RNA

| | | | | | | | | | | | | | | |
|---|---|---|---|---|---|---|---|---|---|---|---|---|---|---|
| 137 | 1 | 15 | 15 | 1:5 | in house prot | 1466 | 1698 rGrG + G | 1 | SSRTIII | 90' @42° C., 30' @60° C., then 30' @42° C. | — | yes | Advantage | 50 | — | 0.3M trehalose |
| 138 | 1 | 15 | 15 | 1:5 | in house prot | 703 | 1580 rGrG + G | 1 | SSRTIII | 60' @50° C., then 90' @42° C. | — | yes | Advantage | 50 | — | 0.6M trehalose |
| 139 | 1 | 15 | 15 | 1:5 | in house prot | 1397 | 1740 rGrG + G | 1 | SSRTIII | 90' @42° C., 30' @60° C., then 30' @42° C. | — | yes | Advantage | 50 | — | 0.6M trehalose |
| 140 | 1 | 15 | 15 | 1:5 | in house prot | 355 | 1425 rGrG + G | 1 | SSRTIII | 60' @50° C., then 90' @42° C. | 0.6 | yes | Advantage | 50 | — | 0.6M trehalose |
| 141 | 1 | 15 | 15 | 1:5 | in house prot | 1654 | 1598 rGrG + G | 1 | SSRTIII | 90' @42° C., 30' @60° C., then 30' @42° C. | 0.6 | yes | Advantage | 50 | — | 0.6M trehalose |
| 142 | 1 | 15 | 15 | 1:5 | in house prot | 1470 | 1480 rGrG + G | 1 | SSRTIII | 60' @50° C., then 90' @42° C. | 0.6 | yes | Advantage | 50 | — | 0.6M trehalose |
| 143 | 1 | 15 | 15 | 1:5 | in house prot | 1389 | 1480 rGrG + G | 1 | SSRTIII | 90' @42° C., 30' @60° C., then 30' @42° C. | 0.6 | yes | Advantage | 50 | — | 0.6M trehalose |
| 144 | 1 | 15 | 15 | 1:5 | in house prot | 3959 | 1641 rGrG + G | 1 | SSRTIII | 90' @42° C., then 10X (2' @50° C.-2' @42° C.) | 1 | yes | Advantage | 50 | — | — |
| 145 | 1 | 15 | 15 | 1:5 | in house prot | 3816 | 1732 rGrG + G | 1 | SSRTIII | 90' @42° C., then 10X (2' @60° C.-2' @42° C.) | 1 | yes | Advantage | 50 | — | — |
| 146 | 1 | 15 | 15 | 1:5 | in house prot | 3179 | 1769 rGrG + G | 1 | SSRTIII | 90' @42° C., then 10X (2' @50° C.-2' @42° C.) | 0.5 | yes | Advantage | 50 | — | 0.3M trehalose |

TABLE S1-continued

Tables of cDNA library yield and length starting with purified total RNA

| | | | | | | | | | | | | | 0.3M trehalose |
|---|---|---|---|---|---|---|---|---|---|---|---|---|---|
| 147 | 1 | 15 | 15 | 1:5 | in house prot | 3271 | 1828 rGrG + G | 1 | SSRTIII | 12 | 90' @42° C., then 10X (2' @60° C.-2' @42° C.) | 0.5 | — |
| 148 | 1 | 15 | 15 | 1:5 | in house prot | 4081 | 1706 rGrG + G | 1 | SSRTIII | 12 | 90' @42° C., then 5x (2' @50° C.-2' @42° C.) | 1 | yes | Advantage | 50 | — | — |
| 149 | 1 | 15 | 15 | 1:5 | in house prot | 3858 | 1771 rGrG + G | 1 | SSRTIII | 12 | 90' @42° C., then 5x (2' @50° C.-2' @42° C.) | 1 | yes | Advantage | 50 | — | — |
| 150 | 1 | 15 | 15 | 1:5 | in house prot | 3711 | 1781 rGrG + G | 1 | SSRTIII | 12 | 90' @42° C., then 5x (2' @50° C.-2' @42° C.) | 1 | yes | Advantage | 50 | — | — |
| 151 | 1 | 15 | 15 | 1:5 | in house prot | 4015 | 1773 rGrG + G | 1 | SSRTIII | 12 | 90' @42° C., then 10x (2' @50° C.-2' @42° C.) | 1 | yes | Advantage | 50 | — | — |
| 152 | 1 | 15 | 15 | 1:5 | in house prot | 3671 | 1753 rGrG + G | 1 | SSRTIII | 12 | 90' @42° C., then 10x (2' @50° C.-2' @42° C.) | 1 | yes | Advantage | 50 | — | — |
| 153 | 1 | 15 | 15 | 1:5 | in house prot | 3498 | 1708 rGrG + G | 1 | SSRTIII | 12 | 90' @42° C., then 10x (2' @50° C.-2' @42° C.) | 1 | yes | Advantage | 50 | — | — |
| 154 | 1 | 15 | 15 | 1:5 | in house prot | 3804 | 1610 rGrG + G | 1 | SSRTIII | 12 | 90' @42° C., then 15x (2' @50° C.-2' @42° C.) | 1 | yes | Advantage | 50 | — | — |
| 155 | 1 | 15 | 15 | 1:5 | in house prot | 3613 | 1679 rGrG + G | 1 | SSRTIII | 12 | 90' @42° C., then 15x (2' @50° C.-2' @42° C.) | 1 | yes | Advantage | 50 | — | — |
| 156 | 1 | 15 | 15 | 1:5 | in house prot | 4595 | 1630 rGrG + G | 1 | SSRTIII | 12 | 90' @42° C., then 15x (2' @50° C.-2' @42° C.) | 1 | yes | Advantage | 50 | — | — |
| 157 | 1 | 15 | 15 | 1:5 | in house prot | 3457 | 1525 rGrG + G | 1 | SSRTIII | 12 | 90' @42° C., then 20x (2' @50° C.-2' @42° C.) | 1 | yes | Advantage | 50 | — | — |
| 158 | 1 | 15 | 15 | 1:5 | in house prot | 2869 | 1409 rGrG + G | 1 | SSRTIII | 12 | 90' @42° C., then 20x (2' @50° C.-2' @42° C.) | 1 | yes | Advantage | 50 | — | — |

TABLE S1-continued

Tables of cDNA library yield and length starting with purified total RNA

| | | | | | | | | | | | | | | | | | |
|---|---|---|---|---|---|---|---|---|---|---|---|---|---|---|---|---|---|
| 159 | 1 | 15 | 15 | 1:5 in house prot | 1529 | 1629 3tGrG + G | 1 | SSRTIII | 12 | 90' @42° C., then 10x (2' @50° C.-2' @42° C.) | 1 | yes | Advantage | 50 | — | — | — |
| 160 | 1 | 15 | 15 | 1:5 in house prot | 1901 | 1728 3tGrG + G | 1 | SSRTIII | 12 | 90' @42° C., then 10x (2' @50° C.-2' @42° C.) | 1 | yes | Advantage | 50 | — | — | — |
| 161 | 1 | 15 | 15 | 1:5 in house prot | 1785 | 1717 3tGrG + G | 1 | SSRTIII | 12 | 90' @42° C., then 10x (2' @50° C.-2' @42° C.) | 1 | yes | Advantage | 50 | — | — | — |
| 162 | 1 | 15 | 15 | 1:5 in house prot | 1086 | 1928 2rGrG + G | 1 | SSRTIII | 12 | 90' @42° C., then 10x (2' @50° C.-2' @42° C.) | 1 | yes | Advantage | 50 | — | — | — |
| 163 | 1 | 15 | 15 | 1:5 in house prot | 1128 | 1846 2rGrG + G | 1 | SSRTIII | 12 | 90' @42° C., then 10x (2' @50° C.-2' @42° C.) | 1 | yes | Advantage | 50 | — | — | — |
| 164 | 1 | 15 | 15 | 1:5 in house prot | 596 | 1892 phosphate | 1 | SSRTIII | 12 | 90' @42° C., then 10x (2' @50° C.-2' @42° C.) | 1 | yes | Advantage | 50 | — | — | — |
| 165 | 1 | 15 | 15 | 1:5 in house prot | 579 | 1922 phosphate | 1 | SSRTIII | 12 | 90' @42° C., then 10x (2' @50° C.-2' @42° C.) | 1 | yes | Advantage | 50 | — | — | — |
| 166 | 1 | 15 | 15 | 1:5 in house prot | 546 | 1830 C6 amino | 1 | SSRTIII | 12 | 90' @42° C., then 10x (2' @50° C.-2' @42° C.) | 1 | yes | Advantage | 50 | — | — | — |
| 167 | 1 | 15 | 15 | 1:5 in house prot | 419 | 1664 C6 amino | 1 | SSRTIII | 12 | 90' @42° C., then 10x (2' @50° C.-2' @42° C.) | 1 | yes | Advantage | 50 | — | — | — |
| 168 | 1 | 15 | 15 | 1:5 in house prot | 3076 | 1567 rGrG + G | 1 | SSRTIII | 12 | 90' @42° C., then 10x (2' @50° C.-2' @42° C.) | 1 | yes | Advantage | 50 | — | — | — |
| 169 | 1 | 15 | 15 | 1:5 in house prot | 2889 | 1465 rGrG + G | 1 | SSRTIII | 12 | 90' @42° C., then 10x (2' @50° C.-2' @42° C.) | 1 | yes | Advantage | 50 | — | — | — |
| 170 | 1 | 15 | 15 | 1:5 in house prot | 3653 | 1735 rGrG + G | 1 | SSRTIII | 12 | 90' @42° C., then 10x (2' @50° C.-2' @42° C.) | 1 | yes | Advantage | 50 | — | — | — |

TABLE S1-continued

Tables of cDNA library yield and length starting with purified total RNA

| | | | | | | | | | | | | | | | | |
|---|---|---|---|---|---|---|---|---|---|---|---|---|---|---|---|---|
| 171 | 1 | 15 | 15 | 1:5 | in house prot | 2152 | 1455 rGrG + G | 1 | SSRIII | 12 | 90' @42° C., then 10x (2' @50° C.-2' @42° C.) | 1 | yes | Advantage | 50 | — |
| 172 | 1 | 15 | 15 | 1:5 | in house prot | 1454 | 1084 rGrG + G | 1 | SSRIII | 12 | 90' @42° C., then 10x (2' @50° C.-2' @42° C.) | 1 | yes | Advantage | 50 | 0.816M 1,2 propandiol |
| 173 | 1 | 15 | 15 | 1:5 | in house prot | 1331 | 1106 rGrG + G | 1 | SSRIII | 12 | 90' @42° C., then 10x (2' @50° C.-2' @42° C.) | 1 | yes | Advantage | 50 | 0.816M 1,2 propandiol |
| 174 | 1 | 15 | 15 | 1:5 | in house prot | 1373 | 1089 rGrG + G | 1 | SSRIII | 12 | 90' @42° C., then 10x (2' @50° C.-2' @42° C.) | 1 | yes | Advantage | 50 | 0.816M 1,2 propandiol |
| 175 | 1 | 15 | 15 | 1:5 | in house prot | 1904 | 1453 rGrG + G | 1 | SSRIII | 12 | 90' @42° C., then 10x (2' @50° C.-2' @42° C.) | 1 | yes | Advantage | 50 | 1.075M ethylene glycol |
| 176 | 1 | 15 | 15 | 1:5 | in house prot | 2855 | 1390 rGrG + G | 1 | SSRIII | 12 | 90' @42° C., then 10x (2' @50° C.-2' @42° C.) | 1 | yes | Advantage | 50 | 1.075M ethylene glycol |
| 177 | 1 | 15 | 15 | 1:5 | in house prot | 2571 | 1670 rGrG + G | 1 | Maxima H- | 4 | 90' @50° C. | 1 | yes | Advantage | 50 | — |
| 178 | 1 | 15 | 15 | 1:5 | in house prot | 2549 | 1722 rGrG + G | 1 | Maxima H- | 4 | 90' @50° C. | 1 | yes | Advantage | 50 | — |
| 179 | 1 | 15 | 15 | 1:5 | in house prot | 288 | 1599 rGrG + G | 1 | Revertaid Premium | 4 | 90' @50° C. | 1 | yes | Advantage | 50 | — |
| 180 | 1 | 15 | 15 | 1:5 | in house prot | 129 | 1608 rGrG + G | 1 | Revertaid Premium | 4 | 90' @50° C. | 1 | yes | Advantage | 50 | — |
| 181 | 1 | | | | in house prot | FAILED | rGrG + G | 1 | Maxima H- | 12 | 90' @50° C. | 1 | yes | Advantage | 50 | — |
| 182 | 1 | | | | in house prot | FAILED | rGrG + G | 1 | Maxima H- | 12 | 90' @50° C. | 1 | yes | Advantage | 50 | — |
| 183 | 1 | 15 | 15 | 1:5 | in house prot | 2633 | 1341 rGrG + G | 1 | Revertaid Premium | 12 | 90' @50° C. | 1 | yes | Advantage | 50 | — |
| 184 | 1 | 15 | 15 | 1:5 | in house prot | 2662 | 1325 rGrG + G | 1 | Revertaid Premium | 12 | 90' @50° C. | 1 | yes | Advantage | 50 | — |
| 185 | 1 | 15 | 15 | 1:5 | in house prot | 2814 | 1674 rGrG + G | 1 | SSRIII | 12 | 90' @42° C., then 10x (2' @50° C.-2' @42° C.) | 1 | yes | Advantage | 50 | — |
| 186 | 1 | | | | in house prot | FAILED | rGrG + G | 1 | SSRIII | 12 | 90' @42° C., then 10x (2' @50° C.-2' @42° C.) | 1 | yes | Long PCR Enzyme mix | 50 | — |

TABLE S1-continued

Tables of cDNA library yield and length starting with purified total RNA

| | | | | | | | | | | | | | | |
|---|---|---|---|---|---|---|---|---|---|---|---|---|---|---|
| 187 | 1 | 15 | 15 | in house prot, PCR w/o purif in 100 ul | 3155 | 1764 rGrG + G | 1 | SSRTIII | 12 | 90' @42° C., then 10x (2' @50° C.- 2' @42° C.) | 1 | Phusion HS | 100 | — |
| 188 | 1 | 15 | 15 | in house prot, PCR w/o purif in 100 ul | 2740 | 1793 rGrG + G | 1 | SSRTIII | 12 | 90' @42° C., then 10x (2' @50° C.- 2' @42° C.) | 1 | Phusion HS | 100 | — |
| 189 | 1 | 15 | 15 | in house prot, PCR w/o purif in 100 ul | 1857 | 1739 rGrG + G | 1 | SSRTIII | 12 | 90' @42° C., then 10x (2' @50° C.- 2' @42° C.) | 1 | Q5 NEB | 100 | — |
| 190 | 1 | 15 | 15 | in house prot, PCR w/o purif in 100 ul | 1697 | 1697 rGrG + G | 1 | SSRTIII | 12 | 90' @42° C., then 10x (2' @50° C.- 2' @42° C.) | 1 | Q5 NEB | 100 | — |
| 191 | 1 | 15 | 15 | in house prot, PCR w/o purif in 100 ul | 3278 | 1639 rGrG + G | 1 | SSRTIII | 12 | 90' @42° C., then 10x (2' @50° C.- 2' @42° C.) | 1 | KAPA HiFi HS | 100 | — |
| 192 | 1 | 15 | 15 | in house prot, PCR w/o purif in 100 ul | 3719 | 1590 rGrG + G | 1 | SSRTIII | 12 | 90' @42° C., then 10x (2' @50° C.- 2' @42° C.) | 1 | KAPA HiFi HS | 100 | — |
| 193 | 1 | 15 | 15 | in house prot, PCR w/o purif in 50 ul | 3816 | 1630 rGrG + G | 1 | SSRTIII | 12 | 90' @42° C., then 10x (2' @50° C.- 2' @42° C.) | 1 | Advantage | 50 | — |
| 194 | 1 | 15 | 15 | in house prot, PCR w/o purif in 50 ul | 2462 | 1653 rGrG + G | 1 | SSRTIII | 12 | 90' @42° C., then 10x (2' @50° C.- 2' @42° C.) | 1 | Advantage | 50 | — |
| 195 | 1 | 15 | 15 | in house prot, PCR w/o purif in 50 ul | 2848 | 1588 rGrG + G | 1 | SSRTIII | 12 | 90' @42° C., then 10x (2' @50° C.- 2' @42° C.) | 1 | Advantage | 50 | — |
| 196 | 1 | 15 | 15 | in house prot, PCR w/o purif in 50 ul | 2012 | 1669 rGrG + G | 1 | SSRTIII | 12 | 90' @42° C., then 10x (2' @50° C.- 2' @42° C.) | 1 | Phusion HS | 50 | — |
| 197 | 1 | 15 | 15 | in house prot, PCR w/o purif in 50 ul | 1836 | 1665 rGrG + G | 1 | SSRTIII | 12 | 90' @42° C., then 10x (2' @50° C.- 2' @42° C.) | 1 | Phusion HS | 50 | — |
| 198 | 1 | 15 | 15 | in house prot, PCR w/o purif in 50 ul | 2542 | 1771 rGrG + G | 1 | SSRTIII | 12 | 90' @42° C., then 10x (2' @50° C.- 2' @42° C.) | 1 | KAPA HiFi HS | 50 | — |

TABLE S1-continued

Tables of cDNA library yield and length starting with purified total RNA

| | | | | | | | | | | | | | | |
|---|---|---|---|---|---|---|---|---|---|---|---|---|---|---|
| 199 | 1 | 15 | 15 | 1:5 | in house prot, PCR w/o purif in 50 ul | 2393 | 1808 rGrG + G | 1 | SSRTIII | 12 | 90' @42° C., then 10x (2' @50° C.-2' @42° C.) | 1 | — | KAPA HiFi HS | 50 | — |
| 200 | 1 | 15 | 15 | 1:5 | in house prot, PCR w/o purif in 50 ul | 2200 | 1933 rGrG + G | 1 | SSRTIII | 12 | 90' @42° C., then 10x (2' @50° C.-2' @42° C.) | 1 | — | Advantage | 50 | — |
| 201 | 1 | 15 | 15 | 1:5 | in house prot, PCR w/o purif in 50 ul | 2371 | 1920 rGrG + G | 1 | SSRTIII | 12 | 90' @42° C., then 10x (2' @50° C.-2' @42° C.) | 1 | — | Advantage | 50 | — |
| 202 | 1 | 15 | 15 | 1:5 | in house prot, PCR w/o purif in 50 ul | 1717 | 1780 rGrG + G | 1 | SSRTIII | 12 | 90' @42° C., then 10x (2' @50° C.-2' @42° C.) | 1 | — | Q5 NEB | 50 | — |
| 203 | 1 | 15 | 15 | 1:5 | in house prot, PCR w/o purif in 50 ul | 1868 | 1759 rGrG + G | 1 | SSRTIII | 12 | 90' @42° C., then 10x (2' @50° C.-2' @42° C.) | 1 | — | Q5 NEB | 50 | — |
| 204 | 1 | 15 | 15 | 1:5 | in house prot | 40 | 1772 rGrG + G | 1 | SSRTIII | 12 | 90' @42° C., then 10x (2' @50° C.-2' @42° C.) | 1 | yes | Advantage | 50 | — |
| 205 | 1 | 15 | 15 | 1:5 | in house prot | 16 | 1017 rGrG + G | 1 | SSRTIII | 12 | 90' @42° C., then 10x (2' @50° C.-2' @42° C.) | 1 | yes | Advantage | 50 | — |
| 206 | 1 | 15 | 15 | 1:5 | in house prot | 88 | 1753 rGrG + G | 1 | SSRTIII | 12 | 90' @42° C., then 10x (2' @50° C.-2' @42° C.) | 1 | yes | Advantage | 50 | — |
| 207 | 1 | 15 | 15 | 1:5 | in house prot | 61 | 1557 rGrG + G | 1 | SSRTIII | 12 | 90' @42° C., then 10x (2' @50° C.-2' @42° C.) | 1 | yes | Advantage | 50 | — |
| 208 | 1 | 15 | 15 | 1:5 | in house prot | 182 | 1766 rGrG + G | 1 | SSRTIII | 12 | 90' @42° C., then 10x (2' @50° C.-2' @42° C.) | 1 | yes | Advantage | 50 | — |
| 209 | 1 | 15 | 15 | 1:5 | in house prot | 136 | 1742 rGrG + G | 1 | SSRTIII | 12 | 90' @42° C., then 10x (2' @50° C.-2' @42° C.) | 1 | yes | Advantage | 50 | — |
| 210 | 1 | 15 | 15 | 1:5 | in house prot | 279 | 1701 rGrG + G | 1 | SSRTIII | 12 | 90' @42° C., then 10x (2' @50° C.-2' @42° C.) | 1 | yes | Advantage | 50 | — |

TABLE S1-continued

Tables of cDNA library yield and length starting with purified total RNA

| | | | | | | | | | | | | | |
|---|---|---|---|---|---|---|---|---|---|---|---|---|---|
| 211 | 1 | 15 | 15 | 1:5 | in house prot | 233 | 1643 rGrG + G | 1 | SSRTIII | 12 | 90' @42° C., then 10x (2' @50° C.-2' @42° C.) | 1 | yes | Advantage | 50 | — | — |
| 212 | 1 | 15 | 15 | 1:5 | in house prot | 447 | 1602 rGrG + G | 1 | SSRTIII | 12 | 90' @42° C., then 10x (2' @50° C.-2' @42° C.) | 1 | yes | Advantage | 50 | — | — |
| 213 | 1 | 15 | 15 | 1:5 | in house prot | 363 | 1541 rGrG + G | 1 | SSRTIII | 12 | 90' @42° C., then 10x (2' @50° C.-2' @42° C.) | 1 | yes | Advantage | 50 | — | — |
| 214 | 1 | 15 | 15 | 1:5 | in house prot | 1279 | 1919 rGrG + G | 1 | SSRTIII | 12 | 90' @42° C., then 10x (2' @50° C.-2' @42° C.) | 1 | yes | Advantage | 50 | — | — |
| 215 | 1 | 15 | 15 | 1:5 | in house prot | 1739 | 1959 rGrG + G | 1 | SSRTIII | 12 | 90' @42° C., then 10x (2' @50° C.-2' @42° C.) | 1 | yes | Advantage | 50 | — | — |
| 216 | 1 | 15 | 15 | 1:5 | in house prot | 1861 | 2063 rGrG + G | 1 | SSRTIII | 12 | 90' @42° C., then 10x (2' @50° C.-2' @42° C.) | 1 | yes | Advantage | 50 | — | — |
| 217 | 1 | 15 | 15 | 1:5 | in house prot (40 u SSRTII) | 2329 | 2260 rGrG + G | 1 | SSRTIII | 12 | 90' @42° C., then 10x (2' @50° C.-2' @42° C.) | 1 | yes | Advantage | 50 | yes | — |
| 218 | 1 | 15 | 15 | 1:5 | in house prot (40 u SSRTII) | 2273 | 2218 rGrG + G | 1 | SSRTIII | 12 | 90' @42° C., then 10x (2' @50° C.-2' @42° C.) | 1 | yes | Advantage | 50 | yes | — |
| 219 | 1 | 15 | 15 | 1:5 | in house prot (40 u SSRTII, with dNTPs + betaine added in the beginning) | 2013 | 2268 rGrG + G | 1 | SSRTIII | 12 | 90' @42° C., then 10x (2' @50° C.-2' @42° C.) | 1 | yes | Advantage | 50 | yes | — |
| 220 | 1 | 15 | 15 | 1:5 | in house prot (40 u SSRTII, with dNTPs + betaine added in the beginning) | 1932 | 2122 rGrG + G | 1 | SSRTIII | 12 | 90' @42° C., then 10x (2' @50° C.-2' @42° C.) | 1 | yes | Advantage | 50 | yes | — |

TABLE S1-continued

Tables of cDNA library yield and length starting with purified total RNA

| | | | | | | | | | | | | |
|---|---|---|---|---|---|---|---|---|---|---|---|---|
| 221 | 1 | 15 | 15 | 1:5 | in house prot (40 u SSRTII, with dNTPs + betaine + MgCl2 added in the beginning) | 1877 | 2009 rGrG + G | 1 | SSRTIII | 12 | 90' @42° C., then 10x (2' @50° C.-2' @42° C.) | 1 | yes | Advantage | 50 | yes | — |
| 222 | 1 | 15 | 15 | 1:5 | in house prot (40 u SSRTII, with dNTPs + betaine + MgCl2 added in the beginning) | 989 | 1963 rGrG + G | 1 | SSRTIII | 12 | 90' @42° C., then 10x (2' @50° C.-2' @42° C.) | 1 | yes | Advantage | 50 | yes | — |
| 223 | 1 | 15 | 15 | 1:5 | in house prot (40 u SSRTII, with all reagents except SSRTII added in the beginning) | 2269 | 1316 rGrG + G | 1 | SSRTIII | 12 | 90' @42° C., then 10x (2' @50° C.-2' @42° C.) | 1 | yes | Advantage | 50 | yes | — |
| 224 | 1 | 15 | 15 | 1:5 | in house prot (40 u SSRTII, with all reagents except SSRTII added in the beginning) | 1926 | 1292 rGrG + G | 1 | SSRTIII | 12 | 90' @42° C., then 10x (2' @50° C.-2' @42° C.) | 1 | yes | Advantage | 50 | yes | — |
| 225 | 1 | 15 | 15 | 1:5 | in house prot (40 u SSRTII, with all reagents except SSRTII added in the beginning) | 1536 | 1297 rGrG + G | 1 | SSRTIII | 12 | 90' @42° C., then 10x (2' @50° C.-2' @42° C.) | 1 | yes | Advantage | 50 | yes | — |
| 226 | 1 | 15 | 15 | 1:5 | in house prot | 1604 | 1925 rGrG + G | 1 | SSRTIII | 12 | 90' @42° C., then 10x (2' @50° C.-2' @42° C.) | 1 | yes | Advantage | 50 | yes | — |
| 227 | 1 | 15 | 15 | 1:5 | in house prot | 1493 | 1910 rGrG + G | 1 | SSRTIII | 12 | 90' @42° C., then 10x (2' @50° C.-2' @42° C.) | 1 | yes | Advantage | 50 | yes | — |

TABLE S1-continued

Tables of cDNA library yield and length starting with purified total RNA

| | | | | | | | | | | | | | | |
|---|---|---|---|---|---|---|---|---|---|---|---|---|---|---|
| 228 | 1 | 15 | 15 | 1:5 | in house prot | 1540 | 1924 rGrG + G | 1 | SSRTIII | 12 | 90' @42° C., then 10x (2' @50° C.-2' @42° C.) | 1 | yes | Advantage | 50 | yes | — |
| 229 | 1 | 15 | 15 | 1:5 | in house prot | 1946 | 2143 rGrG + G | 1 | SSRTIII | 12 | 90' @42° C., then 10x (2' @50° C.-2' @42° C.) | 1 | yes | Advantage | 50 | yes | — |
| 230 | 1 | 15 | 15 | 1:5 | in house prot | 1620 | 2100 rGrG + G | 1 | SSRTIII | 12 | 90' @42° C., then 10x (2' @50° C.-2' @42° C.) | 1 | yes | Advantage | 50 | yes | — |
| 231 | 1 | 15 | 15 | 1:5 | in house prot | 1724 | 2059 rGrG + G | 1 | SSRTIII | 12 | 90' @42° C., then 10x (2' @50° C.-2' @42° C.) | 1 | yes | Advantage | 50 | yes | — |
| 232 | 1 | 15 | 15 | 1:5 | in house prot (no denaturation step @72° C. for oligo-dT (incubated 5' @RT)) | 1355 | 1813 rGrG + G | 1 | SSRTIII | 12 | 90' @42° C., then 10x (2' @50° C.-2' @42° C.) | 1 | yes | Advantage | 50 | — | — |
| 233 | 1 | 15 | 15 | 1:5 | in house prot (no denaturation step @72° C. for oligo-dT (incubated 5' @RT)) | 1330 | 1810 rGrG + G | 1 | SSRTIII | 12 | 90' @42° C., then 10x (2' @50° C.-2' @42° C.) | 1 | yes | Advantage | 50 | — | — |
| 234 | 1 | 15 | 15 | 1:5 | in house prot (no denaturation step @72° C. for oligo-dT (incubated 5' @RT)) | 1319 | 1795 rGrG + G | 1 | SSRTIII | 12 | 90' @42° C., then 10x (2' @50° C.-2' @42° C.) | 1 | yes | Advantage | 50 | — | — |
| 235 | 1 | 15 | 15 | 1:5 | in house prot (no denaturation step @72° C. for oligo-dT (incubated 5' @RT)) | 1493 | 1842 rGrG + G | 1 | SSRTIII | 12 | 90' @42° C., then 10x (2' @50° C.-2' @42° C.) | 1 | yes | Advantage | 50 | yes | — |
| 236 | 1 | 15 | 15 | 1:5 | in house prot (no denaturation step @72° C. for oligo-dT (incubated 5' @RT)) | 1332 | 1792 rGrG + G | 1 | SSRTIII | 12 | 90' @42° C., then 10x (2' @50° C.-2' @42° C.) | 1 | yes | Advantage | 50 | yes | — |

TABLE S1-continued

Tables of cDNA library yield and length starting with purified total RNA

| | | | | | | | | | | | | | |
|---|---|---|---|---|---|---|---|---|---|---|---|---|---|
| 237 | 1 | 15 | 15 | 1:5 | in house prot | 1728 | 2214 rGrG + G | 1 | SSRTII | 12 | 90' @42° C., then 10x (2' @50° C.-2' @42° C.) | 1 | yes | Advantage | 50 | yes | — |
| 238 | 1 | 15 | 15 | 1:5 | in house prot | 1620 | 2283 rGrG + G | 1 | SSRTII | 12 | 90' @42° C., then 10x (2' @50° C.-2' @42° C.) | 1 | yes | Advantage | 50 | yes | — |
| 239 | 1 | 15 | 15 | 1:5 | in house prot | 1563 | 2260 rGrG + G | 1 | SSRTII | 12 | 90' @42° C., then 10x (2' @50° C.-2' @42° C.) | 1 | yes | Advantage | 50 | yes | — |
| 240 | 1 | 15 | 15 | 1:5 | in house prot | 1485 | 2171 rGrG + G | 1 | SSRTII | 12 | 90' @42° C., then 10x (2' @50° C.-2' @42° C.) | 1 | yes | Advantage | 50 | yes | — |
| 241 | 1 | 15 | 15 | 1:5 | in house prot | 1444 | 2281 rGrG + G | 1 | SSRTII | 12 | 90' @42° C., then 10x (2' @55° C.-2' @42° C.) | 1 | yes | Advantage | 50 | yes | — |
| 242 | 1 | 15 | 15 | 1:5 | in house prot | 1308 | 2231 rGrG + G | 1 | SSRTII | 12 | 90' @42° C., then 10x (2' @55° C.-2' @42° C.) | 1 | yes | Advantage | 50 | yes | — |
| 243 | 1 | 15 | 15 | 1:5 | in house prot | 1618 | 2176 rGrG + G | 1 | SSRTII | 12 | 90' @42° C., then 10x (2' @55° C.-2' @42° C.) | 1 | yes | Advantage | 50 | yes | — |
| 244 | 1 | 15 | 15 | 1:5 | in house prot | 1385 | 2168 rGrG + G | 1 | SSRTII | 12 | 90' @42° C., then 10x (2' @60° C.-2' @42° C.) | 1 | yes | Advantage | 50 | yes | — |
| 245 | 1 | 15 | 15 | 1:5 | in house prot | 1588 | 2173 rGrG + G | 1 | SSRTII | 12 | 90' @42° C., then 10x (2' @60° C.-2' @42° C.) | 1 | yes | Advantage | 50 | yes | — |
| 246 | 1 | 15 | 15 | 1:5 | in house prot | 1332 | 2096 rGrG + G | 1 | SSRTII | 12 | 90' @42° C. | 1 | yes | Advantage | 50 | yes | — |
| 247 | 1 | 15 | 15 | 1:5 | in house prot | 1376 | 2054 rGrG + G | 1 | SSRTII | 12 | 90' @42° C. | 1 | yes | Advantage | 50 | yes | — |
| 248 | 1 | 15 | 15 | 1:5 | in house prot | 15 | 2251 rGrG + G | 1 | Maxima H- | 4 | 90' @55° C. | — | yes | Advantage | 50 | yes | — |
| 249 | 1 | 15 | 15 | 1:5 | in house prot | 22 | 1988 rGrG + G | 1 | Maxima H- | 4 | 90' @55° C. | — | yes | Advantage | 50 | yes | — |
| 250 | 1 | 15 | 15 | 1:5 | in house prot | 62 | 2084 rGrG + G | 1 | Maxima H- | 4 | 90' @42° C. | 1 | yes | Advantage | 50 | yes | — |
| 251 | 1 | 15 | 15 | 1:5 | in house prot | 84 | 1867 rGrG + G | 1 | Maxima H- | 4 | 90' @55° C. | 1 | yes | Advantage | 50 | yes | — |
| 252 | 1 | 15 | 15 | 1:5 | in house prot | 633 | 2065 rGrG + G | 1 | Maxima H- | 4 | 90' @55° C. | — | yes | Advantage | 50 | yes | — |

TABLE S1-continued

Tables of cDNA library yield and length starting with purified total RNA

| # | | | | | | | | | | | | | | | | | |
|---|---|---|---|---|---|---|---|---|---|---|---|---|---|---|---|---|---|
| 253 | 1 | 15 | in house prot (+extra DTT) | 1:5 | FAILED | rGrG + G | 1 | Maxima H- | 4 | 90' @60° C. | — | yes | Advantage | 50 | yes | — |
| 254 | 1 | 15 | in house prot (+extra DTT) | 1:5 | FAILED | rGrG + G | 1 | Maxima H- | 4 | 90' @60° C. | 1 | yes | Advantage | 50 | yes | — |
| 255 | 1 | 15 | in house prot (+extra DTT) | 1:5 | FAILED | rGrG + G | 1 | Maxima H- | 12 | 90' @60° C. | 1 | yes | Advantage | 50 | yes | — |
| 256 | 1 | 15 | in house prot (+extra DTT) | 1:5 | 80 | 1933 | rGrG + G | 1 | Maxima H- | 12 | 90' @60° C. | — | yes | Advantage | 50 | yes | — |
| 257 | 1 | 15 | in house prot (+extra DTT) | 1:5 | 634 | 2177 | rGrG + G | 1 | Maxima H- | 4 | 90' @60° C. | 1 | yes | Advantage | 50 | yes | — |
| 258 | 1 | 15 | in house prot (+extra DTT) | 1:5 | 684 | 2195 | rGrG + G | 1 | Maxima H- | 4 | 90' @50° C. | 1 | yes | Advantage | 50 | yes | — |
| 259 | 1 | 15 | in house prot (+extra DTT) | 1:5 | 1013 | 2142 | rGrG + G | 1 | Maxima H- | 4 | 90' @50° C. | 1 | yes | Advantage | 50 | yes | — |
| 260 | 1 | 15 | in house prot (+extra DTT) | 1:5 | 1195 | 2100 | rGrG + G | 1 | Maxima H- | 4 | 90' @50° C. | 1 | yes | Advantage | 50 | yes | — |
| 261 | 1 | 15 | in house prot (+extra DTT) | 1:5 | 2192 | 1858 | rGrG + G | 1 | Maxima H- | 12 | 90' @50° C. | 1 | yes | Advantage | 50 | yes | — |
| 262 | 1 | 15 | in house prot (+extra DTT) | 1:5 | 2209 | 1837 | rGrG + G | 1 | Maxima H- | 12 | 90' @50° C. | 1 | yes | Advantage | 50 | yes | — |
| 263 | 1 | 15 | in house prot (NO extra DTT) | 1:5 | 647 | 2117 | rGrG + G | 1 | Maxima H- | 4 | 90' @50° C. | — | yes | Advantage | 50 | yes | — |
| 264 | 1 | 15 | in house prot (NO extra DTT) | 1:5 | 613 | 2147 | rGrG + G | 1 | Maxima H- | 4 | 90' @50° C. | 1 | yes | Advantage | 50 | yes | — |
| 265 | 1 | 15 | in house prot | 1:5 | 1442 | 1989 | rGrG + G | 1 | SSRTIII | 12 | 90' @42° C., then 10x (2' @50° C.-2' @42° C.) | 1 | yes | Advantage | 50 | yes | — |
| 266 | 1 | 15 | in house prot | 1:5 | 1496 | 2105 | rGrG + G | 1 | SSRTIII | 12 | 90' @42° C., then 10x (2' @50° C.-2' @42° C.) | 1 | yes | Advantage | 50 | yes | — |
| 267 | 1 | 15 | in house prot | 1:5 | 1228 | 2677 | rGrG + G | 1 | Maxima H- | 4 | 90' @50° C. | — | — | KAPA HiFi HS | 50 | yes | — |
| 268 | 1 | 15 | in house prot | 1:5 | 882 | 2283 | rGrG + G | 1 | Maxima H- | 4 | 90' @50° C. | — | — | KAPA HiFi HS Advantage | 50 | yes | — |
| 269 | 1 | 15 | in house prot | 1:5 | 2475 | 2558 | rGrG + G | 1 | Maxima H- | 4 | 90' @50° C. | 1 | — | KAPA HiFi HS | 50 | yes | — |
| 270 | 1 | 15 | in house prot | 1:5 | 1557 | 2201 | rGrG + G | 1 | Maxima H- | 4 | 90' @50° C. | 1 | — | KAPA HiFi HS Advantage | 50 | yes | — |
| 271 | 1 | 15 | in house prot | 1:5 | 4074 | 2185 | rGrG + G | 1 | Maxima H- | 12 | 90' @50° C. | 1 | — | KAPA HiFi HS | 50 | yes | — |
| 272 | 1 | 15 | in house prot | 1:5 | 2927 | 2330 | rGrG + G | 1 | Maxima H- | 12 | 90' @50° C. | 1 | — | KAPA HiFi HS Advantage | 50 | yes | — |
| 273 | 1 | 15 | in house prot | 1:5 | 3213 | 2524 | rGrG + G | 1 | SSRTIII | 12 | 90' @42° C., then 10x (2' @50° C.-2' @42° C.) | 1 | — | KAPA HiFi HS | 50 | yes | — |

TABLE S1-continued

Tables of cDNA library yield and length starting with purified total RNA

| | | | | | | | | | | | | | | | | | |
|---|---|---|---|---|---|---|---|---|---|---|---|---|---|---|---|---|---|
| 274 | 1 | 15 | 15 | 1:5 | in house prot | 3359 | 2662 rGrG + G | 1 | SSRTIII | 12 | 90' @42° C., then 10x (2' @50° C.- 2' @42° C.) | 1 | — | Advantage | 50 | yes | — |
| 275 | 1 | 15 | 15 | 1:5 | in house prot | 819 | 2069 rGrG + G | 1 | Maxima H- | 4 | 90' @ 50° C. | — | yes | — | — | — | — |
| 276 | 1 | 15 | 15 | 1:5 | in house prot | 737 | 2202 rGrG + G | 1 | Maxima H- | 4 | 90' @ 50° C. | — | yes | — | — | — | — |
| 277 | 1 | 15 | 15 | 1:5 | in house prot | 1375 | 1937 rGrG + G | 1 | Maxima H- | 4 | 90' @ 50° C. | 1 | yes | — | — | — | — |
| 278 | 1 | 15 | 15 | 1:5 | in house prot | 1426 | 2008 rGrG + G | 1 | Maxima H- | 4 | 90' @ 50° C. | 1 | yes | — | — | — | — |
| 279 | 1 | 15 | 15 | 1:5 | in house prot | 2773 | 1848 rGrG + G | 1 | Maxima H- | 12 | 90' @42° C. | 1 | yes | — | — | — | — |
| 280 | 1 | 15 | 15 | 1:5 | in house prot | 2987 | 1916 rGrG + G | 1 | Maxima H- | 12 | 90' @ 50° C. | 1 | yes | — | — | — | — |
| 281 | 1 | 15 | 15 | 1:5 | in house prot | 2155 | 2266 rGrG + G | 1 | SSRTIII | 12 | 90' @42° C., then 10x (2' @50° C.- 2' @42° C.) | 1 | yes | — | — | — | — |
| 282 | 1 | 15 | 15 | 1:5 | in house prot | 2240 | 2271 rGrG + G | 1 | SSRTIII | 12 | 90' @42° C., then 10x (2' @50° C.- 2' @42° C.) | 1 | yes | Advantage | 50 | yes | — |
| 283 | 1 | 15 | 15 | 1:5 | in house prot | 694 | 2244 rGrG + G | 1 | SSRTIII | 6 | 90' @42° C. | — | yes | Advantage | 50 | yes | 1M proline |
| 284 | 1 | 15 | 15 | 1:5 | in house prot | 682 | 2361 rGrG + G | 1 | SSRTIII | 6 | 90' @42° C. | — | yes | Advantage | 50 | yes | 1M proline |
| 285 | 1 | 15 | 15 | 1:5 | in house prot | 745 | 2264 rGrG + G | 1 | SSRTIII | 6 | 90' @42° C. | — | yes | Advantage | 50 | yes | 1M proline |
| 286 | 1 | 15 | 15 | 1:5 | in house prot | 766 | 2311 rGrG + G | 1 | SSRTIII | 12 | 90' @42° C. | — | yes | Advantage | 50 | yes | 1M proline |
| 287 | 1 | 15 | 15 | 1:5 | in house prot | 685 | 2304 rGrG + G | 1 | SSRTIII | 12 | 90' @42° C., then 10x (2' @50° C.- 2' @42° C.) | — | yes | Advantage | 50 | yes | 1M proline |
| 288 | 1 | 15 | 15 | 1:5 | in house prot | 642 | 2226 rGrG + G | 1 | SSRTIII | 12 | 90' @42° C., then 10x (2' @50° C.- 2' @42° C.) | — | yes | Advantage | 50 | yes | 1M proline |

TABLE S1-continued

Tables of cDNA library yield and length starting with purified total RNA

| | | | | | | | | | | | |
|---|---|---|---|---|---|---|---|---|---|---|---|
| 289 | 1 | 15 | 1 | 15 | 1:5 in house prot | 1133 | 1873 rGrG + G | 1 | SSRTII | 12 | 90' @42° C., then 10x (2' @50° C.- 2' @42° C.) | 1 | yes | Advantage | 50 | yes |
| 290 | 1 | 15 | 15 | 1:5 in house prot | 1443 | 2148 rGrG + G | 1 | SSRTII | 12 | 90' @42° C., then 10x (2' @50° C.- 2' @42° C.) | 1 | yes | Advantage | 50 | yes |
| 291 | 1 | 15 | 15 | 1:5 in house prot | 1147 | 2066 rGrG + G | 1 | SSRTII | 12 | 90' @42° C., then 10x (2' @50° C.- 2' @42° C.) | 1 | yes | Advantage | 50 | yes |
| 292 | 1 | 15 | 15 | 1:5 in house prot | 1322 | 2084 rGrG + G | 1 | SSRTII | 12 | 90' @42° C., then 10x (2' @50° C.- 2' @42° C.) | 1 | yes | Advantage | 50 | yes |
| 293 | 1 | 15 | 15 | 1:5 in house prot | 1013 | 2095 rGrG + G | 1 | SSRTII | 12 | 90' @42° C., then 10x (2' @50° C.- 2' @42° C.) | 1 | yes | Advantage | 50 | yes |
| 294 | 1 | 15 | 15 | 1:5 in house prot | 960 | 2125 rGrG + G | 1 | SSRTII | 12 | 90' @42° C., then 10x (2' @50° C.- 2' @42° C.) | 1 | yes | Advantage | 50 | yes |
| 295 | 1 | 15 | 15 | 1:5 in house prot with SMARTer dT30 (unanchored oligo) | 1296 | 2129 rGrG + G | 1 | SSRTII | 12 | 90' @42° C., then 10x (2' @50° C.- 2' @42° C.) | 1 | yes | Advantage | 50 | yes |
| 296 | 1 | 15 | 15 | 1:5 in house prot with SMARTer dT30 (unanchored oligo) | 1390 | 2194 rGrG + G | 1 | SSRTII | 12 | 90' @42° C., then 10x (2' @50° C.- 2' @42° C.) | 1 | yes | Advantage | 50 | yes |
| 297 | 1 | 15 | 15 | 1:5 in house prot with SMARTer dT30 (unanchored oligo) | 1419 | 2084 rGrG + G | 1 | SSRTII | 12 | 90' @42° C., then 10x (2' @50° C.- 2' @42° C.) | 1 | yes | Advantage | 50 | yes |
| 298 | 1 | 18 | 15 | 1:20 in house prot | 5456 | 2293 rGrG + G | 2 | SSRTII | 12 | 90' @42° C., then 10x (2' @50° C.- 2' @42° C.) | 1 | yes | Advantage | 50 | yes |
| 299 | 1 | 18 | 15 | 1:20 in house prot | 5753 | 2334 rGrG + G | 2 | SSRTII | 12 | 90' @42° C., then 10x (2' @50° C.- 2' @42° C.) | 1 | yes | Advantage | 50 | yes |

TABLE S1-continued

Tables of cDNA library yield and length starting with purified total RNA

| | | | | | | | | | | | | | |
|---|---|---|---|---|---|---|---|---|---|---|---|---|---|
| 300 | 1 | 18 | 15 | 1:20 in house prot | 5341 | 2365 rGrG + G | 2 | SSRTIII | 12 | 90' @42° C., then 10x (2' @50° C.-2' @42° C.) | 1 | yes | Advantage | 50 | yes |
| 301 | 1 | 18 | 15 | 1:20 in house prot | 2266 | 1750 rGrG + G | 2 | SSRTIII | 12 | 90' @42° C., then 10x (2' @50° C.-2' @42° C.) | 1 | yes | Advantage | 50 | yes |
| 302 | 1 | 18 | 15 | 1:20 in house prot | 1530 | 1850 rGrG + G | 2 | SSRTIII | 12 | 90' @42° C., then 10x (2' @50° C.-2' @42° C.) | 1 | yes | Advantage | 50 | yes |
| 303 | 1 | 18 | 15 | 1:20 in house prot | 1883 | 1703 rGrG + G | 2 | SSRTIII | 12 | 90' @42° C., then 10x (2' @50° C.-2' @42° C.) | 1 | yes | Advantage | 50 | yes |
| 304 | 1 | 18 | 15 | 1:20 in house prot | 2856 | 1731 rGrG + G | 2 | SSRTIII | 12 | 90' @42° C., then 10x (2' @50° C.-2' @42° C.) | 1 | yes | Advantage | 50 | yes |
| 305 | 1 | 18 | 15 | 1:20 in house prot | 3150 | 2371 rGrG + N | 1 | SSRTIII | 12 | 90' @42° C., then 10x (2' @50° C.-2' @42° C.) | 1 | yes | Advantage | 50 | yes |
| 306 | 1 | 18 | 15 | 1:20 in house prot | 2889 | 2393 rGrG + N | 1 | SSRTIII | 12 | 90' @42° C., then 10x (2' @50° C.-2' @42° C.) | 1 | yes | Advantage | 50 | yes |
| 307 | 1 | 18 | 15 | 1:20 in house prot | 3773 | 2302 rGrG + N | 2 | SSRTIII | 12 | 90' @42° C., then 10x (2' @50° C.-2' @42° C.) | 1 | yes | Advantage | 50 | yes |
| 308 | 1 | 18 | 15 | 1:20 in house prot | 3744 | 2318 rGrG + N | 2 | SSRTIII | 12 | 90' @42° C., then 10x (2' @50° C.-2' @42° C.) | 1 | yes | Advantage | 50 | yes |
| 309 | 1 | 18 | 15 | 1:20 in house prot | 4113 | 2390 rGrG + N | 2 | SSRTIII | 12 | 90' @42° C., then 10x (2' @50° C.-2' @42° C.) | 1 | yes | Advantage | 50 | yes |
| 310 | 1 | 18 | 15 | 1:20 in house prot | 3903 | 2309 rGrG + N | 2 | SSRTIII | 12 | 90' @42° C., then 10x (2' @50° C.-2' @42° C.) | 1 | yes | Advantage | 50 | yes |
| 311 | 1 | 18 | 15 | 1:20 in house prot | 2649 | 2436 rGrG + N | 2 | SSRTIII | 12 | 90' @42° C., then 10x (2' @50° C.-2' @42° C.) | 1 | yes | Advantage | 50 | yes |

TABLE S1-continued

Tables of cDNA library yield and length starting with purified total RNA

| | | | | | | | | | | | | | | |
|---|---|---|---|---|---|---|---|---|---|---|---|---|---|---|
| 312 | 1 | 18 | 15 | 1:20 in house prot | 2856 | 2422 rGrG + N | 2 | SSRIII | 12 | 90' @42° C., then 10x (2' @50° C.- 2' @42° C.) | 1 | yes | Advantage | 50 | yes |
| 313 | 1 | 18 | 15 | 1:20 in house prot | 2674 | 2412 rGrG + N | 2 | SSRIII | 12 | 90' @42° C., then 10x (2' @50° C.- 2' @42° C.) | 1 | yes | Advantage | 50 | yes |
| 314 | 1 | 18 | 15 | 1:20 in house prot | 2641 | 2427 rGrG + N | 2 | SSRIII | 12 | 90' @42° C., then 10x (2' @50° C.- 2' @42° C.) | 1 | yes | Advantage | 50 | yes |
| 315 | 1 | 18 | 15 | 1:20 in house prot | 5251 | 2272 rGrG + G | 2 | SSRIII | 12 | 90' @42° C., then 10x (2' @50° C.- 2' @42° C.) | 1 | yes | Advantage | 50 | yes |
| 316 | 1 | 15 | 15 | 1:5 in house prot | 1255 | 2057 rGrG + G | 1 | SSRIII | 12 | 90' @42° C., then 10x (2' @50° C.- 2' @42° C.) | 1 | — | KAPA HiFi HS | 50 | yes |
| 317 | 1 | 15 | 15 | 1:6 in house prot | 1135 | 2123 rGrG + G | 1 | SSRIII | 12 | 90' @42° C., then 10x (2' @50° C.- 2' @42° C.) | 1 | — | KAPA HiFi HS | 50 | yes |
| 318 | 1 | 15 | 15 | 1:7 in house prot | 925 | 2224 rGrG + G | 1 | SSRIII | 12 | 90' @42° C., then 10x (2' @50° C.- 2' @42° C.) | 1 | — | KAPA HiFi HS | 50 | yes |
| 319 | 1 | 15 | 15 | 1:8 in house prot | 790 | 2326 rGrG + G | 1 | SSRIII | 12 | 90' @42° C., then 10x (2' @50° C.- 2' @42° C.) | 1 | — | KAPA HiFi HS | 50 | yes |
| 320 | 1 | 15 | 15 | 1:9 in house prot | 9 | 2866 rGrG + G | 1 | SSRIII | 12 | 30' @42° C., 10' @50° C., 10' @55° C. | 1 | — | KAPA HiFi HS | 50 | yes | 1M sorbitol + 0.3M trehalose |
| 321 | 1 | 15 | 15 | 1:10 in house prot | 17 | 2648 rGrG + G | 1 | SSRIII | 12 | 30' @42° C., 10' @50° C., 10' @55° C. | 1 | — | KAPA HiFi HS | 50 | yes | 1M sorbitol + 0.3M trehalose |
| 322 | 1 | 15 | 15 | 1:11 in house prot | 18 | 2744 rGrG + G | 1 | SSRIII | 12 | 30' @42° C., 10' @50° C., 10' @55° C. | 1 | — | KAPA HiFi HS | 50 | yes | 1M sorbitol + 0.3M trehalose |

TABLE S1-continued

Tables of cDNA library yield and length starting with purified total RNA

| | | | | | | | | | | | | | | | | | | |
|---|---|---|---|---|---|---|---|---|---|---|---|---|---|---|---|---|---|---|
| 323 | 1 | 15 | 1 | 15 | 1:12 in house prot | 14 | 2844 | rGrG + G | 1 | SSRTII | 1 | 30' @42° C., 10' @50° C., 10' @55° C. | 12 | — | KAPA HiFi HS | 50 | yes | 1M sorbitol + 0.3M trehalose |
| 324 | 1 | 15 | 1 | 15 | 1:13 in house prot | 24 | 2546 | rGrG + G | 1 | SSRTII | 1 | 30' @42° C., 10' @50° C., 10' @55° C. | 12 | — | KAPA HiFi HS | 50 | yes | 0.75M sorbitol + 0.15M trehalose |
| 325 | 1 | 15 | 1 | 15 | 1:14 in house prot | 30 | 2478 | rGrG + G | 1 | SSRTII | 1 | 30' @42° C., 10' @50° C., 10' @55° C. | 12 | — | KAPA HiFi HS | 50 | yes | 0.75M sorbitol + 0.15M trehalose |
| 326 | 1 | 15 | 1 | 15 | 1:15 in house prot | 40 | 2609 | rGrG + G | 1 | SSRTII | 1 | 30' @42° C., 10' @50° C., 10' @55° C. | 12 | — | KAPA HiFi HS | 50 | yes | 0.75M sorbitol + 0.15M trehalose |
| 327 | 1 | 18 | 1 | 15 | 1:10 in house prot | 3197 | 2061 | rGrG + G | 1 | SSRTII | 1 | 90' @42° C., then 10x (2' @50° C.-2' @42° C.) | 15 | — | KAPA HiFi HS | 50 | yes | |
| 328 | 1 | 18 | 1 | 15 | 1:10 in house prot | 3085 | 2065 | rGrG + G | 1 | SSRTII | 1 | 90' @42° C., then 10x (2' @50° C.-2' @42° C.) | 15 | — | KAPA HiFi HS | 50 | yes | |
| 329 | 1 | 18 | 1 | 15 | 1:10 in house prot | 2627 | 2134 | rGrG + G | 1 | SSRTII | 1 | 90' @42° C., then 10x (2' @50° C.-2' @42° C.) | 15 | — | KAPA HiFi HS | 50 | yes | |
| 330 | 1 | 18 | 1 | 15 | 1:10 in house prot | 2750 | 2035 | rGrG + G | 1 | SSRTII | 1 | 90' @42° C., then 10x (2' @50° C.-2' @42° C.) | 15 | — | KAPA HiFi HS | 50 | yes | |
| 331 | 1 | 18 | 1 | 15 | 1:10 in house prot | 980 | 1920 | rGrG + G | 1 | SSRTII | 1 | 90' @42° C., then 10x (2' @50° C.-2' @42° C.) | 3 | — | KAPA HiFi HS | 50 | yes | |
| 332 | 1 | 18 | 1 | 15 | 1:10 in house prot | 997 | 1863 | rGrG + G | 1 | SSRTII | 1 | 90' @42° C., then 10x (2' @50° C.-2' @42° C.) | 3 | — | KAPA HiFi HS | 50 | yes | |

TABLE S1-continued

Tables of cDNA library yield and length starting with purified total RNA

| | | | | | | | | | | | | | |
|---|---|---|---|---|---|---|---|---|---|---|---|---|---|
| 333 | 1 | 18 | 15 | 1:10 in house prot | 1055 | 1925 rGrG + G | 1 | SSRTII | 3 | 90' @42° C., then 10x (2' @50° C.-2' @42° C.) | 1 | — | KAPA HiFi HS | 50 | yes |
| 334 | 1 | 18 | 15 | 1:10 in house prot | 938 | 1931 rGrG + G | 1 | SSRTII | 3 | 90' @42° C., then 10x (2' @50° C.-2' @42° C.) | 1 | — | KAPA HiFi HS | 50 | yes |
| 335 | 1 | 18 | 15 | 1:10 in house prot | 2192 | 2119 rGrG + G | 1 | SSRTII | 6 | 90' @42° C., then 10x (2' @50° C.-2' @42° C.) | 1 | — | KAPA HiFi HS | 50 | yes |
| 336 | 1 | 18 | 15 | 1:10 in house prot | 2122 | 2046 rGrG + G | 1 | SSRTII | 6 | 90' @42° C., then 10x (2' @50° C.-2' @42° C.) | 1 | — | KAPA HiFi HS | 50 | yes |
| 337 | 1 | 18 | 15 | 1:10 in house prot | 2408 | 2079 rGrG + G | 1 | SSRTII | 6 | 90' @42° C., then 10x (2' @50° C.-2' @42° C.) | 1 | — | KAPA HiFi HS | 50 | yes |
| 338 | 1 | 18 | 15 | 1:10 in house prot | 1836 | 2109 rGrG + G | 1 | SSRTII | 6 | 90' @42° C., then 10x (2' @50° C.-2' @42° C.) | 1 | — | KAPA HiFi HS | 50 | yes |
| 339 | 1 | 18 | 15 | 1:10 in house prot | 2861 | 2098 rGrG + G | 1 | SSRTII | 9 | 90' @42° C., then 10x (2' @50° C.-2' @42° C.) | 1 | — | KAPA HiFi HS | 50 | yes |
| 340 | 1 | 18 | 15 | 1:10 in house prot | 2518 | 2086 rGrG + G | 1 | SSRTII | 9 | 90' @42° C., then 10x (2' @50° C.-2' @42° C.) | 1 | — | KAPA HiFi HS | 50 | yes |
| 341 | 1 | 18 | 15 | 1:10 in house prot | 2289 | 2135 rGrG + G | 1 | SSRTII | 9 | 90' @42° C., then 10x (2' @50° C.-2' @42° C.) | 1 | — | KAPA HiFi HS | 50 | yes |
| 342 | 1 | 18 | 15 | 1:10 in house prot | 2553 | 2168 rGrG + G | 1 | SSRTII | 9 | 90' @42° C., then 10x (2' @50° C.-2' @42° C.) | 1 | — | KAPA HiFi HS | 50 | yes |
| 343 | 1 | 18 | 15 | 1:10 in house prot | 2571 | 2134 rGrG + G | 1 | SSRTII | 12 | 90' @42° C., then 10x (2' @50° C.-2' @42° C.) | 1 | — | KAPA HiFi HS | 50 | yes |
| 344 | 1 | 18 | 15 | 1:10 in house prot | 2691 | 2115 rGrG + G | 1 | SSRTII | 12 | 90' @42° C., then 10x (2' @50° C.-2' @42° C.) | 1 | — | KAPA HiFi HS | 50 | yes |

TABLE S1-continued

Tables of cDNA library yield and length starting with purified total RNA

| | | | | | | | | | | | | | | |
|---|---|---|---|---|---|---|---|---|---|---|---|---|---|---|
| 345 | 1 | 18 | 15 | 1:10 in house prot | 2348 | 2121 rGrG + G | 1 | SSRIII | 12 | 90' @42° C., then 10x (2' @50° C.-2' @42° C.) | 1 | — | KAPA HiFi HS | 50 | yes |
| 346 | 1 | 18 | 15 | 1:10 in house prot | 2046 | 2162 rGrG + G | 1 | SSRIII | 12 | 90' @42° C., then 10x (2' @50° C.-2' @42° C.) | 1 | — | KAPA HiFi HS | 50 | yes |
| 347 | 1 | 15 | 15 | 1:5 in house prot | 37 | 1918 rGrG + G | 1 | SSRIII | 3 | 90' @42° C., then 10x (2' @50° C.-2' @42° C.) | 1 | — | KAPA HiFi HS | 25 | yes |
| 348 | 1 | 15 | 15 | 1:5 in house prot | 65 | 1888 rGrG + G | 1 | SSRIII | 3 | 90' @42° C., then 10x (2' @50° C.-2' @42° C.) | 1 | — | KAPA HiFi HS | 25 | yes |
| 349 | 1 | 15 | 15 | 1:5 in house prot | 46 | 1976 rGrG + G | 1 | SSRIII | 3 | 90' @42° C., then 10x (2' @50° C.-2' @42° C.) | 1 | — | KAPA HiFi HS | 25 | yes |
| 350 | 1 | 15 | 15 | 1:5 in house prot | 39 | 1966 rGrG + G | 1 | SSRIII | 3 | 90' @42° C., then 10x (2' @50° C.-2' @42° C.) | 1 | — | KAPA HiFi HS | 25 | yes |
| 351 | 1 | 15 | 15 | 1:5 in house prot | 44 | 1784 rGrG + G | 1 | SSRIII | 3 | 90' @42° C., then 10x (2' @50° C.-2' @42° C.) | 1 | — | KAPA HiFi HS | 25 | yes |
| 352 | 1 | 15 | 15 | 1:5 in house prot | 95 | 1791 rGrG + G | 1 | SSRIII | 3 | 90' @42° C., then 10x (2' @50° C.-2' @42° C.) | 1 | — | KAPA HiFi HS | 25 | yes |
| 353 | 1 | 15 | 15 | 1:5 in house prot | 80 | 1897 rGrG + G | 1 | SSRIII | 3 | 90' @42° C., then 10x (2' @50° C.-2' @42° C.) | 1 | — | KAPA HiFi HS | 25 | yes |
| 354 | 1 | 15 | 15 | 1:5 in house prot | 281 | 1685 rGrG + G | 1 | SSRIII | 6 | 90' @42° C., then 10x (2' @50° C.-2' @42° C.) | 1 | — | KAPA HiFi HS | 25 | yes |
| 355 | 1 | 15 | 15 | 1:5 in house prot | 348 | 1753 rGrG + G | 1 | SSRIII | 6 | 90' @42° C., then 10x (2' @50° C.-2' @42° C.) | 1 | — | KAPA HiFi HS | 25 | yes |
| 356 | 1 | 15 | 15 | 1:5 in house prot | 204 | 1734 rGrG + G | 1 | SSRIII | 6 | 90' @42° C., then 10x (2' @50° C.-2' @42° C.) | 1 | — | KAPA HiFi HS | 25 | yes |

TABLE S1-continued

Tables of cDNA library yield and length starting with purified total RNA

| | | | | | | | | | | | | | | |
|---|---|---|---|---|---|---|---|---|---|---|---|---|---|---|
| 357 | 1 | 15 | 15 | 1:5 | in house prot | 210 | 1840 | rGrG + G | 1 | SSRTIII | 6 | 90' @42° C., then 10x (2' @50° C.-2' @42° C.) | 1 | — | KAPA HiFi HS | 25 | yes |
| 358 | 1 | 15 | 15 | 1:5 | in house prot | 207 | 1853 | rGrG + G | 1 | SSRTIII | 6 | 90' @42° C., then 10x (2' @50° C.-2' @42° C.) | 1 | — | KAPA HiFi HS | 25 | yes |
| 359 | 1 | 15 | 15 | 1:5 | in house prot | 285 | 1801 | rGrG + G | 1 | SSRTIII | 6 | 90' @42° C., then 10x (2' @50° C.-2' @42° C.) | 1 | — | KAPA HiFi HS | 25 | yes |
| 360 | 1 | 15 | 15 | 1:5 | in house prot | 120 | 1942 | rGrG + G | 1 | SSRTIII | 6 | 90' @42° C., then 10x (2' @50° C.-2' @42° C.) | 1 | — | KAPA HiFi HS | 25 | yes |
| 361 | 1 | 15 | 15 | 1:5 | in house prot | 201 | 1732 | rGrG + G | 1 | SSRTIII | 6 | 90' @42° C., then 10x (2' @50° C.-2' @42° C.) | 1 | — | KAPA HiFi HS | 25 | yes |
| 362 | 1 | 15 | 15 | 1:5 | in house prot | 395 | 1808 | rGrG + G | 1 | SSRTIII | 9 | 90' @42° C., then 10x (2' @50° C.-2' @42° C.) | 1 | — | KAPA HiFi HS | 25 | yes |
| 363 | 1 | 15 | 15 | 1:5 | in house prot | 558 | 1887 | rGrG + G | 1 | SSRTIII | 9 | 90' @42° C., then 10x (2' @50° C.-2' @42° C.) | 1 | — | KAPA HiFi HS | 25 | yes |
| 364 | 1 | 15 | 15 | 1:5 | in house prot | 429 | 1792 | rGrG + G | 1 | SSRTIII | 9 | 90' @42° C., then 10x (2' @50° C.-2' @42° C.) | 1 | — | KAPA HiFi HS | 25 | yes |
| 365 | 1 | 15 | 15 | 1:5 | in house prot | 340 | 1779 | rGrG + G | 1 | SSRTIII | 9 | 90' @42° C., then 10x (2' @50° C.-2' @42° C.) | 1 | — | KAPA HiFi HS | 25 | yes |
| 366 | 1 | 15 | 15 | 1:5 | in house prot | 511 | 1797 | rGrG + G | 1 | SSRTIII | 9 | 90' @42° C., then 10x (2' @50° C.-2' @42° C.) | 1 | — | KAPA HiFi HS | 25 | yes |
| 367 | 1 | 15 | 15 | 1:5 | in house prot | 353 | 1783 | rGrG + G | 1 | SSRTIII | 9 | 90' @42° C., then 10x (2' @50° C.-2' @42° C.) | 1 | — | KAPA HiFi HS | 25 | yes |
| 368 | 1 | 15 | 15 | 1:5 | in house prot | 365 | 1785 | rGrG + G | 1 | SSRTIII | 9 | 90' @42° C., then 10x (2' @50° C.-2' @42° C.) | 1 | — | KAPA HiFi HS | 25 | yes |

TABLE S1-continued

Tables of cDNA library yield and length starting with purified total RNA

| | | | | | | | | | | | | | | |
|---|---|---|---|---|---|---|---|---|---|---|---|---|---|---|
| 369 | 1 | 15 | 15 | 1:5 | in house prot | 333 | 1840 rGrG + G | 1 | SSRTIII | 9 | 90' @42° C., then 10x (2' @50° C.-2' @42° C.) | 1 | — | KAPA HiFi HS | 25 | yes |
| 370 | 1 | 15 | 15 | 1:5 | in house prot | 477 | 1818 rGrG + G | 1 | SSRTIII | 12 | 90' @42° C., then 10x (2' @50° C.-2' @42° C.) | 1 | — | KAPA HiFi HS | 25 | yes |
| 371 | 1 | 15 | 15 | 1:5 | in house prot | 517 | 1754 rGrG + G | 1 | SSRTIII | 12 | 90' @42° C., then 10x (2' @50° C.-2' @42° C.) | 1 | — | KAPA HiFi HS | 25 | yes |
| 372 | 1 | 15 | 15 | 1:5 | in house prot | 265 | 1917 rGrG + G | 1 | SSRTIII | 12 | 90' @42° C., then 10x (2' @50° C.-2' @42° C.) | 1 | — | KAPA HiFi HS | 25 | yes |
| 373 | 1 | 15 | 15 | 1:5 | in house prot | 349 | 1815 rGrG + G | 1 | SSRTIII | 12 | 90' @42° C., then 10x (2' @50° C.-2' @42° C.) | 1 | — | KAPA HiFi HS | 25 | yes |
| 374 | 1 | 15 | 15 | 1:5 | in house prot | 255 | 1763 rGrG + G | 1 | SSRTIII | 12 | 90' @42° C., then 10x (2' @50° C.-2' @42° C.) | 1 | — | KAPA HiFi HS | 25 | yes |
| 375 | 1 | 15 | 15 | 1:5 | in house prot | 388 | 1760 rGrG + G | 1 | SSRTIII | 12 | 90' @42° C., then 10x (2' @50° C.-2' @42° C.) | 1 | — | KAPA HiFi HS | 25 | yes |
| 376 | 1 | 15 | 15 | 1:5 | in house prot | 387 | 1816 rGrG + G | 1 | SSRTIII | 12 | 90' @42° C., then 10x (2' @50° C.-2' @42° C.) | 1 | — | KAPA HiFi HS | 25 | yes |
| 377 | 1 | 15 | 15 | 1:5 | in house prot | 635 | 1928 rGrG + G | 1 | SSRTIII | 15 | 90' @42° C., then 10x (2' @50° C.-2' @42° C.) | 1 | — | KAPA HiFi HS | 25 | yes |
| 378 | 1 | 15 | 15 | 1:5 | in house prot | 515 | 1873 rGrG + G | 1 | SSRTIII | 15 | 90' @42° C., then 10x (2' @50° C.-2' @42° C.) | 1 | — | KAPA HiFi HS | 25 | yes |
| 379 | 1 | 15 | 15 | 1:5 | in house prot | 658 | 1989 rGrG + G | 1 | SSRTIII | 15 | 90' @42° C., then 10x (2' @50° C.-2' @42° C.) | 1 | — | KAPA HiFi HS | 25 | yes |
| 380 | 1 | 15 | 15 | 1:5 | in house prot | 602 | 1905 rGrG + G | 1 | SSRTIII | 15 | 90' @42° C., then 10x (2' @50° C.-2' @42° C.) | 1 | — | KAPA HiFi HS | 25 | yes |

TABLE S1-continued

Tables of cDNA library yield and length starting with purified total RNA

| | | | | | | | | | | | | | |
|---|---|---|---|---|---|---|---|---|---|---|---|---|---|
| 381 | 1 | 15 | 15 | 1:5 | in house prot | 412 | 1896 rGrG + G | 1 | SSRTIII | 15 | 90' @42° C., then 10x (2' @50° C.- 2' @42° C.) | 1 | — | KAPA HiFi HS | 25 | yes |
| 382 | 1 | 15 | 15 | 1:5 | in house prot | 476 | 1958 rGrG + G | 1 | SSRTIII | 15 | 90' @42° C., then 10x (2' @50° C.- 2' @42° C.) | 1 | — | KAPA HiFi HS | 25 | yes |
| 383 | 1 | 15 | 15 | 1:5 | in house prot | 422 | 1853 rGrG + G | 1 | SSRTIII | 15 | 90' @42° C., then 10x (2' @50° C.- 2' @42° C.) | 1 | — | KAPA HiFi HS | 25 | yes |
| 384 | 1 | 15 | 15 | 1:5 | in house prot | 551 | 1876 rGrG + G | 1 | SSRTIII | 15 | 90' @42° C., then 10x (2' @50° C.- 2' @42° C.) | 1 | — | KAPA HiFi HS | 25 | yes |
| 385 | 1 | 15 | 15 | 1:5 | in house prot | 1736 | 1698 rGrG + G | 1 | SSRTIII | 20 | 90' @42° C., then 10x (2' @50° C.- 2' @42° C.) | 1 | — | KAPA HiFi HS | 25 | yes |
| 386 | 1 | 15 | 15 | 1:5 | in house prot | 1294 | 1750 rGrG + G | 1 | SSRTIII | 20 | 90' @42° C., then 10x (2' @50° C.- 2' @42° C.) | 1 | — | KAPA HiFi HS | 25 | yes |
| 387 | 1 | 15 | 15 | 1:5 | in house prot | 1160 | 1736 rGrG + G | 1 | SSRTIII | 20 | 90' @42° C., then 10x (2' @50° C.- 2' @42° C.) | 1 | — | KAPA HiFi HS | 25 | yes |
| 388 | 1 | 15 | 15 | 1:5 | in house prot | 1245 | 1786 rGrG + G | 1 | SSRTIII | 20 | 90' @42° C., then 10x (2' @50° C.- 2' @42° C.) | 1 | — | KAPA HiFi HS | 25 | yes |
| 389 | 1 | 15 | 15 | 1:5 | in house prot | 1234 | 1733 rGrG + G | 1 | SSRTIII | 25 | 90' @42° C., then 10x (2' @50° C.- 2' @42° C.) | 1 | — | KAPA HiFi HS | 25 | yes |
| 390 | 1 | 15 | 15 | 1:5 | in house prot | 1654 | 1684 rGrG + G | 1 | SSRTIII | 25 | 90' @42° C., then 10x (2' @50° C.- 2' @42° C.) | 1 | — | KAPA HiFi HS | 25 | yes |
| 391 | 1 | 15 | 15 | 1:5 | in house prot | 1327 | 1696 rGrG + G | 1 | SSRTIII | 25 | 90' @42° C., then 10x (2' @50° C.- 2' @42° C.) | 1 | — | KAPA HiFi HS | 25 | yes |
| 392 | 1 | 15 | 15 | 1:5 | in house prot | 1713 | 1596 rGrG + G | 1 | SSRTIII | 25 | 90' @42° C., then 10x (2' @50° C.- 2' @42° C.) | 1 | — | KAPA HiFi HS | 25 | yes |

TABLE S1-continued

Tables of cDNA library yield and length starting with purified total RNA

| | | | | | | | | | | | | | |
|---|---|---|---|---|---|---|---|---|---|---|---|---|---|
| 393 | 1 | 15 | 15 | 1:5 | in house prot | 1428 | 1667 rGrG + G | 1 | SSRTIII | 30 | 90' @42° C., then 10x (2' @50° C.-2' @42° C.) | 1 | — | KAPA HiFi HS | 25 | yes |
| 394 | 1 | 15 | 15 | 1:5 | in house prot | 1274 | 1711 rGrG + G | 1 | SSRTIII | 30 | 90' @42° C., then 10x (2' @50° C.-2' @42° C.) | 1 | — | KAPA HiFi HS | 25 | yes |
| 395 | 1 | 15 | 15 | 1:5 | in house prot | 1471 | 1651 rGrG + G | 1 | SSRTIII | 30 | 90' @42° C., then 10x (2' @50° C.-2' @42° C.) | 1 | — | KAPA HiFi HS | 25 | yes |
| 396 | 1 | 15 | 15 | 1:5 | in house prot | 1362 | 1653 rGrG + G | 1 | SSRTIII | 30 | 90' @42° C., then 10x (2' @50° C.-2' @42° C.) | 1 | — | KAPA HiFi HS | 25 | yes |
| 397 | 1 | 15 | 15 | 1:5 | in house prot | 86 | 1996 rGrG + G | 1 | SSRTIII | 6 | 90' @42° C., then 10x (2' @50° C.-2' @42° C.) | 1 | — | KAPA HiFi HS | 25 | yes |
| 398 | 1 | 15 | 15 | 1:5 | in house prot | 66 | 2002 rGrG + G | 1 | SSRTIII | 6 | 90' @42° C., then 10x (2' @50° C.-2' @42° C.) | 1 | — | KAPA HiFi HS | 25 | yes |
| 399 | 1 | 15 | 15 | 1:5 | in house prot | 92 | 1941 rGrG + G | 1 | SSRTIII | 6 | 90' @42° C., then 10x (2' @50° C.-2' @42° C.) | 1 | — | KAPA HiFi HS | 25 | yes |
| 400 | 1 | 15 | 15 | 1:5 | in house prot | 86 | 1898 rGrG + G | 1 | SSRTIII | 6 | 90' @42° C., then 10x (2' @50° C.-2' @42° C.) | 1 | — | KAPA HiFi HS | 25 | yes |
| 401 | 1 | 15 | 15 | 1:5 | in house prot | 85 | 2071 rGrG + G | 1 | SSRTIII | 9 | 90' @42° C., then 10x (2' @50° C.-2' @42° C.) | 1 | — | KAPA HiFi HS | 25 | yes |
| 402 | 1 | 15 | 15 | 1:5 | in house prot | 75 | 2078 rGrG + G | 1 | SSRTIII | 9 | 90' @42° C., then 10x (2' @50° C.-2' @42° C.) | 1 | — | KAPA HiFi HS | 25 | yes |
| 403 | 1 | 15 | 15 | 1:5 | in house prot | 120 | 2081 rGrG + G | 1 | SSRTIII | 9 | 90' @42° C., then 10x (2' @50° C.-2' @42° C.) | 1 | — | KAPA HiFi HS | 25 | yes |
| 404 | 1 | 15 | 15 | 1:5 | in house prot | 150 | 1984 rGrG + G | 1 | SSRTIII | 9 | 90' @42° C., then 10x (2' @50° C.-2' @42° C.) | 1 | — | KAPA HiFi HS | 25 | yes |

TABLE S1-continued

Tables of cDNA library yield and length starting with purified total RNA

| | | | | | | | | | | | | | | | | | |
|---|---|---|---|---|---|---|---|---|---|---|---|---|---|---|---|---|---|
| 405 | 1 | 15 | 15 | 1:5 | in house prot | 132 | 2088 | rGrG + G | 1 | SSRTIII | 12 | 90' @42° C., then 10x (2' @50° C.- 2' @42° C.) | 1 | — | KAPA HiFi HS | 25 | yes |
| 406 | 1 | 15 | 15 | 1:5 | in house prot | 101 | 2139 | rGrG + G | 1 | SSRTIII | 12 | 90' @42° C., then 10x (2' @50° C.- 2' @42° C.) | 1 | — | KAPA HiFi HS | 25 | yes |
| 407 | 1 | 15 | 15 | 1:5 | in house prot | 131 | 2221 | rGrG + G | 1 | SSRTIII | 12 | 90' @42° C., then 10x (2' @50° C.- 2' @42° C.) | 1 | — | KAPA HiFi HS | 25 | yes |
| 408 | 1 | 15 | 15 | 1:5 | in house prot | 149 | 2083 | rGrG + G | 1 | SSRTIII | 12 | 90' @42° C., then 10x (2' @50° C.- 2' @42° C.) | 1 | — | KAPA HiFi HS | 25 | yes |
| 409 | 1 | 15 | 15 | 1:5 | in house prot | 169 | 2105 | rGrG + G | 1 | SSRTIII | 15 | 90' @42° C., then 10x (2' @50° C.- 2' @42° C.) | 1 | — | KAPA HiFi HS | 25 | yes |
| 410 | 1 | 15 | 15 | 1:5 | in house prot | 195 | 2020 | rGrG + G | 1 | SSRTIII | 15 | 90' @42° C., then 10x (2' @50° C.- 2' @42° C.) | 1 | — | KAPA HiFi HS | 25 | yes |
| 411 | 1 | 15 | 15 | 1:5 | in house prot | 141 | 2042 | rGrG + G | 1 | SSRTIII | 15 | 90' @42° C., then 10x (2' @50° C.- 2' @42° C.) | 1 | — | KAPA HiFi HS | 25 | yes |
| 412 | 1 | 15 | 15 | 1:5 | in house prot | 196 | 2077 | rGrG + G | 1 | SSRTIII | 15 | 90' @42° C., then 10x (2' @50° C.- 2' @42° C.) | 1 | — | KAPA HiFi HS | 25 | yes |
| 413 | 1 | 15 | 15 | 1:5 | in house prot | 123 | 2133 | rGrG + G | 1 | SSRTIII | 20 | 90' @42° C., then 10x (2' @50° C.- 2' @42° C.) | 1 | — | KAPA HiFi HS | 25 | yes |
| 414 | 1 | 15 | 15 | 1:5 | in house prot | 136 | 2042 | rGrG + G | 1 | SSRTIII | 20 | 90' @42° C., then 10x (2' @50° C.- 2' @42° C.) | 1 | — | KAPA HiFi HS | 25 | yes |
| 415 | 1 | 15 | 15 | 1:5 | in house prot | 153 | 2008 | rGrG + G | 1 | SSRTIII | 20 | 90' @42° C., then 10x (2' @50° C.- 2' @42° C.) | 1 | — | KAPA HiFi HS | 25 | yes |
| 416 | 1 | 15 | 15 | 1:5 | in house prot | 166 | 2111 | rGrG + G | 1 | SSRTIII | 20 | 90' @42° C., then 10x (2' @50° C.- 2' @42° C.) | 1 | — | KAPA HiFi HS | 25 | yes |

TABLE S1-continued

Tables of cDNA library yield and length starting with purified total RNA

| | | | | | | | | | | | | |
|---|---|---|---|---|---|---|---|---|---|---|---|---|
| 417 | 1 | 15 | 15 | 1:5 | in house prot | 259 | 2484 rGrG + G | 1 | SSRTIII | 6 | 90' @42° C., then 10x (2' @50° C.-2' @42° C.) | — | KAPA HiFi HS | 25 | yes |
| 418 | 1 | 15 | 15 | 1:5 | in house prot | 255 | 2505 rGrG + G | 1 | SSRTIII | 6 | 90' @42° C., then 10x (2' @50° C.-2' @42° C.) | — | KAPA HiFi HS | 25 | yes |
| 419 | 1 | 15 | 15 | 1:5 | in house prot | 231 | 2493 rGrG + G | 1 | SSRTIII | 6 | 90' @42° C., then 10x (2' @50° C.-2' @42° C.) | — | KAPA HiFi HS | 25 | yes |
| 420 | 1 | 15 | 15 | 1:5 | in house prot | 258 | 2469 rGrG + G | 1 | SSRTIII | 6 | 90' @42° C., then 10x (2' @50° C.-2' @42° C.) | — | KAPA HiFi HS | 25 | yes |
| 421 | 1 | 15 | 15 | 1:5 | in house prot | 226 | 2529 rGrG + G | 1 | SSRTIII | 6 | 90' @42° C., then 10x (2' @50° C.-2' @42° C.) | — | KAPA HiFi HS | 25 | yes |
| 422 | 1 | 15 | 15 | 1:5 | in house prot | 280 | 2402 rGrG + G | 1 | SSRTIII | 6 | 90' @42° C., then 10x (2' @50° C.-2' @42° C.) | — | KAPA HiFi HS | 25 | yes |
| 423 | 1 | 15 | 15 | 1:5 | in house prot | 270 | 2449 rGrG + G | 1 | SSRTIII | 6 | 90' @42° C., then 10x (2' @50° C.-2' @42° C.) | — | KAPA HiFi HS | 25 | yes |
| 424 | 1 | 15 | 15 | 1:5 | in house prot | 249 | 2557 rGrG + G | 1 | SSRTIII | 6 | 90' @42° C., then 10x (2' @50° C.-2' @42° C.) | — | KAPA HiFi HS | 25 | yes |
| 425 | 1 | 15 | 15 | 1:5 | in house prot | 423 | 1680 rGrG + G | 1 | SSRTIII | 9 | 90' @42° C., then 10x (2' @50° C.-2' @42° C.) | — | KAPA HiFi HS | 25 | yes |
| 426 | 1 | 15 | 15 | 1:5 | in house prot | 433 | 2537 rGrG + G | 1 | SSRTIII | 9 | 90' @42° C., then 10x (2' @50° C.-2' @42° C.) | — | KAPA HiFi HS | 25 | yes |
| 427 | 1 | 15 | 15 | 1:5 | in house prot | 504 | 2571 rGrG + G | 1 | SSRTIII | 9 | 90' @42° C., then 10x (2' @50° C.-2' @42° C.) | — | KAPA HiFi HS | 25 | yes |
| 428 | 1 | 15 | 15 | 1:5 | in house prot | 483 | 2002 rGrG + G | 1 | SSRTIII | 9 | 90' @42° C., then 10x (2' @50° C.-2' @42° C.) | — | KAPA HiFi HS | 25 | yes |

TABLE S1-continued

Tables of cDNA library yield and length starting with purified total RNA

| | | | | | | | | | | | | |
|---|---|---|---|---|---|---|---|---|---|---|---|---|
| 429 | 1 | 15 | 15 | 1:5 | in house prot | 585 | 2409 rGrG + G | 1 | SSRTIII | 9 | 90' @42° C., then 10x (2' @50° C.-2' @42° C.) | — | KAPA HiFi HS | 25 | yes |
| 430 | 1 | 15 | 15 | 1:5 | in house prot | 502 | 2591 rGrG + G | 1 | SSRTIII | 9 | 90' @42° C., then 10x (2' @50° C.-2' @42° C.) | — | KAPA HiFi HS | 25 | yes |
| 431 | 1 | 15 | 15 | 1:5 | in house prot | 541 | 2533 rGrG + G | 1 | SSRTIII | 9 | 90' @42° C., then 10x (2' @50° C.-2' @42° C.) | — | KAPA HiFi HS | 25 | yes |
| 432 | 1 | 15 | 15 | 1:5 | in house prot | 554 | 2555 rGrG + G | 1 | SSRTIII | 9 | 90' @42° C., then 10x (2' @50° C.-2' @42° C.) | — | KAPA HiFi HS | 25 | yes |
| 433 | 1 | 15 | 15 | 1:5 | in house prot | 677 | 2368 rGrG + G | 1 | SSRTIII | 12 | 90' @42° C., then 10x (2' @50° C.-2' @42° C.) | — | KAPA HiFi HS | 25 | yes |
| 434 | 1 | 15 | 15 | 1:5 | in house prot | 792 | 2287 rGrG + G | 1 | SSRTIII | 12 | 90' @42° C., then 10x (2' @50° C.-2' @42° C.) | — | KAPA HiFi HS | 25 | yes |
| 435 | 1 | 15 | 15 | 1:5 | in house prot | 842 | 2325 rGrG + G | 1 | SSRTIII | 12 | 90' @42° C., then 10x (2' @50° C.-2' @42° C.) | — | KAPA HiFi HS | 25 | yes |
| 436 | 1 | 15 | 15 | 1:5 | in house prot | 737 | 2312 rGrG + G | 1 | SSRTIII | 12 | 90' @42° C., then 10x (2' @50° C.-2' @42° C.) | — | KAPA HiFi HS | 25 | yes |
| 437 | 1 | 15 | 15 | 1:5 | in house prot | 831 | 2233 rGrG + G | 1 | SSRTIII | 12 | 90' @42° C., then 10x (2' @50° C.-2' @42° C.) | — | KAPA HiFi HS | 25 | yes |
| 438 | 1 | 15 | 15 | 1:5 | in house prot | 780 | 2468 rGrG + G | 1 | SSRTIII | 12 | 90' @42° C., then 10x (2' @50° C.-2' @42° C.) | — | KAPA HiFi HS | 25 | yes |
| 439 | 1 | 15 | 15 | 1:5 | in house prot | 41 | 2536 rGrG + G | 1 | SSRTIII | 6 | 90' @42° C., then 10x (2' @50° C.-2' @42° C.) | — | KAPA HiFi HS | 25 | yes |
| 440 | 1 | 15 | 15 | 1:5 | in house prot | 28 | 2646 rGrG + G | 1 | SSRTIII | 6 | 90' @42° C., then 10x (2' @50° C.-2' @42° C.) | — | KAPA HiFi HS | 25 | yes |

TABLE S1-continued

Tables of cDNA library yield and length starting with purified total RNA

| | | | | | | | | | | | |
|---|---|---|---|---|---|---|---|---|---|---|---|
| 441 | 1 | 15 | 15 | 1:5 | in house prot | 44 | 2702 rGrG + G | 1 | SSRTIII | 6 | 90' @42° C., then 10x (2' @50° C.-2' @42° C.) | — | KAPA HiFi HS | 25 | yes |
| 442 | 1 | 15 | 15 | 1:5 | in house prot | 30 | 2504 rGrG + G | 1 | SSRTIII | 6 | 90' @42° C., then 10x (2' @50° C.-2' @42° C.) | — | KAPA HiFi HS | 25 | yes |
| 443 | 1 | 15 | 15 | 1:5 | in house prot | 47 | 2664 rGrG + G | 1 | SSRTIII | 9 | 90' @42° C., then 10x (2' @50° C.-2' @42° C.) | — | KAPA HiFi HS | 25 | yes |
| 444 | 1 | 15 | 15 | 1:5 | in house prot | 54 | 2652 rGrG + G | 1 | SSRTIII | 9 | 90' @42° C., then 10x (2' @50° C.-2' @42° C.) | — | KAPA HiFi HS | 25 | yes |
| 445 | 1 | 15 | 15 | 1:5 | in house prot | 70 | 2502 rGrG + G | 1 | SSRTIII | 9 | 90' @42° C., then 10x (2' @50° C.-2' @42° C.) | — | KAPA HiFi HS | 25 | yes |
| 446 | 1 | 15 | 15 | 1:5 | in house prot | 80 | 2555 rGrG + G | 1 | SSRTIII | 9 | 90' @42° C., then 10x (2' @50° C.-2' @42° C.) | — | KAPA HiFi HS | 25 | yes |
| 447 | 1 | 15 | 15 | 1:5 | in house prot | 122 | 2374 rGrG + G | 1 | SSRTIII | 12 | 90' @42° C., then 10x (2' @50° C.-2' @42° C.) | — | KAPA HiFi HS | 25 | yes |
| 448 | 1 | 15 | 15 | 1:5 | in house prot | 138 | 2368 rGrG + G | 1 | SSRTIII | 12 | 90' @42° C., then 10x (2' @50° C.-2' @42° C.) | — | KAPA HiFi HS | 25 | yes |
| 449 | 1 | 15 | 15 | 1:5 | in house prot | 105 | 2441 rGrG + G | 1 | SSRTIII | 12 | 90' @42° C., then 10x (2' @50° C.-2' @42° C.) | — | KAPA HiFi HS | 25 | yes |
| 450 | 1 | 15 | 15 | 1:5 | in house prot | 108 | 2377 rGrG + G | 1 | SSRTIII | 12 | 90' @42° C., then 10x (2' @50° C.-2' @42° C.) | — | KAPA HiFi HS | 25 | yes |
| 451 | 1 | 15 | 15 | 1:5 | in house prot | 128 | 2113 rGrG + G | 1 | SSRTIII | 15 | 90' @42° C., then 10x (2' @50° C.-2' @42° C.) | — | KAPA HiFi HS | 25 | yes |
| 452 | 1 | 15 | 15 | 1:5 | in house prot | 147 | 2049 rGrG + G | 1 | SSRTIII | 15 | 90' @42° C., then 10x (2' @50° C.-2' @42° C.) | — | KAPA HiFi HS | 25 | yes |

TABLE S1-continued

Tables of cDNA library yield and length starting with purified total RNA

| 453 | 1 | 15 | 1:5 | in house prot | 1 | 2127 rGrG + G | 15 | 90' @42° C., then 10x (2' @50° C.-2' 42° C.) | — | KAPA HiFi HS | 25 | yes |
| 454 | 1 | 15 | 1:5 | in house prot | 1 | 2251 rGrG + G | 15 | 90' @42° C., then 10x (2' @50° C.-2' 42° C.) | — | KAPA HiFi HS | 25 | yes |
| 455 | 1 | 15 | 1:5 | in house prot | 1 | 2007 rGrG + G | 20 | 90' @42° C., then 10x (2' @50° C.-2' 42° C.) | — | KAPA HiFi HS | 25 | yes |
| 456 | 1 | 15 | 1:5 | in house prot | 1 | 2104 rGrG + G | 20 | 90' @42° C., then 10x (2' @50° C.-2' 42° C.) | — | KAPA HiFi HS | 25 | yes |
| 457 | 1 | 15 | 1:5 | in house prot | 1 | 2147 rGrG + G | 20 | 90' @42° C., then 10x (2' @50° C.-2' 42° C.) | — | KAPA HiFi HS | 25 | yes |
| 458 | 1 | 15 | 1:5 | in house prot | 1 | 1963 rGrG + G | 20 | 90' @42° C., then 10x (2' @50° C.-2' 42° C.) | — | KAPA HiFi HS | 25 | yes |

B. Analyses of experimental variables effecting cDNA library yield and length

To evaluate the effect on cDNA yield and length of each component of the protocol, we compiled groups of replicates from different experiments that only differed in the experimental variable evaluated (column A). These experiments were used to compute Student t-test p-values and Wilcoxon rank sum test p-values for both cDNA yield and cDNA average length.

| Experi-mental Variable Tested | Variant 1 | Variant 2 | cDNA Yield ||||  cDNA length |||| Number of replicates |
|---|---|---|---|---|---|---|---|---|---|---|---|
| | | | t-test Yield | Wilcoxon-test Yield | mean yield (Var1) | mean yield (Var2) | t-test cDNA length | wilcoxon-test cDNA length | mean length (Var1) | mean length (Var2) | |
| elution volume (ul) | 20 | 30 | 2.69E-02 | 3.33E-01 | 166.79 | 56.535 | 2.43E-01 | 3.33E-01 | 2230.5 | 1930 | 2 |
| TSO | 2rGrG + G | 3rGrG + G | 3.01E-02 | 3.33E-01 | 83.025 | 138.225 | 1.50E-01 | 3.33E-01 | 1887 | 1722.5 | 2 |
| TSO | 2rGrG + G | C6 amino | 4.43E-02 | 3.33E-01 | 83.025 | 36.1875 | 3.11E-01 | 3.33E-01 | 1887 | 1747 | 2 |
| TSO | 2rGrG + G | rGrG + G phosphate | 2.56E-04 | 3.33E-01 | 83.025 | 299.025 | 1.71E-01 | 3.33E-01 | 1887 | 1707 | 2 |
| TSO | 2rGrG + G | ddC | 1.12E-02 | 3.33E-01 | 83.025 | 44.0625 | 7.13E-01 | 1.00E+00 | 1887 | 1907 | 2 |
| TSO | 2OMe | rGrG + G | 2.00E-01 | 9.52E-02 | 117.39 | 62.7 | 8.95E-01 | 8.41E-01 | 1779.2 | 1795.8 | 5 |
| TSO | 2OMe | rGrG | 2.59E-02 | 7.94E-03 | 117.39 | 369.615 | 7.72E-02 | 1.51E-01 | 1779.2 | 1597 | 5 |
| TSO | 2OMe | SMARTer Oligo IIA | 7.68E-01 | 8.86E-01 | 123.675 | 109.9313 | 8.19E-03 | 2.86E-02 | 1797.75 | 1416.5 | 4 |
| TSO | | | — | — | 69.225 | 84.225 | — | — | 1734 | 1652 | 1 |
| TSO | 3rGrG + G | C6 amino | 4.11E-03 | 3.33E-01 | 138.225 | 36.1875 | 8.17E-01 | 1.00E+00 | 1722.5 | 1747 | 2 |
| TSO | 3rGrG + G | rGrG + G | 1.36E-03 | 1.00E-01 | 130.375 | 285.775 | 6.09E-01 | 1.00E+00 | 1691.3333 | 1646.3333 | 3 |
| TSO | 3rGrG + G | phosphate | 2.63E-02 | 3.33E-01 | 138.225 | 44.0625 | 3.09E-02 | 3.33E-01 | 1722.5 | 1907 | 2 |

TABLE S1-continued

Tables of cDNA library yield and length starting with purified total RNA

| | | | | | | | | | | | |
|---|---|---|---|---|---|---|---|---|---|---|---|
| TSO | C6 amino | rGrG + G | 3.25E-03 | 3.33E-01 | 36.1875 | 299.025 | 7.44E-01 | 6.67E-01 | 1747 | 1707 | 2 |
| TSO | C6 amino | phosphate | 3.42E-01 | 3.33E-01 | 36.1875 | 44.0625 | 2.97E-01 | 3.33E-01 | 1747 | 1907 | 2 |
| TSO | ddC | rGrG + G | 1.36E-02 | 7.94E-03 | 62.7 | 369.615 | 1.53E-01 | 2.22E-01 | 1795.8 | 1597 | 5 |
| TSO | ddC | rGrGrG | 2.16E-01 | 2.00E-01 | 66.4313 | 109.9313 | 6.64E-02 | 1.14E-01 | 1770.5 | 1416.5 | 4 |
| TSO | ddC | SMARTer Oligo IIA | — | — | 30.075 | 84.225 | — | — | 1463 | 1652 | 1 |
| TSO | dGCGGG | dGCGGGp | 2.63E-03 | 1.00E-01 | 47.3067 | 14.2533 | 9.78E-04 | 1.00E-01 | 2104.6667 | 2309.3333 | 3 |
| TSO | dGCGGG | rGrGrG | 2.21E-02 | 1.00E-01 | 47.3067 | 150.6733 | 9.85E-01 | 7.00E-01 | 2104.6667 | 2107.3333 | 2 |
| TSO | dGCGGG | rGrGrGp | 1.32E-01 | 3.33E-01 | 48.33 | 35.64 | 2.38E-03 | 3.33E-01 | 2117.5 | 2588.5 | 3 |
| TSO | dGCGGGp | rGrGrG | 1.37E-02 | 1.00E-01 | 14.253 | 150.6733 | 2.41E-01 | 1.00E-01 | 2309.3333 | 2107.3333 | 3 |
| TSO | dGCGGGp | rGrGrGp | 2.47E-03 | 3.33E-01 | 14.48 | 35.64 | 5.93E-02 | 3.33E-01 | 2317 | 2588.5 | 2 |
| TSO | rGrG + G | phosphate | 2.41E-03 | 3.33E-01 | 299.025 | 44.0625 | 1.89E-01 | 3.33E-01 | 1707 | 1907 | 2 |
| TSO | rGrG + G | rGrGrG | 6.55E-03 | 4.96E-04 | 235.7125 | 82.075 | 1.71E-01 | 2.14E-01 | 1588.8333 | 1713 | 12 |
| TSO | rGrG + G | SMARTer Oligo IIA | 2.74E-01 | 3.33E-01 | 197.6625 | 77.175 | 5.20E-02 | 3.33E-01 | 1444 | 1622.5 | 2 |
| TSO | rGrGrG | rGrGrGp | 4.64E-04 | 2.86E-02 | 154.565 | 32.765 | 2.56E-05 | 2.86E-02 | 2256.5 | 2583.5 | 4 |
| TSO | rGrGrG | SMARTer Oligo IIA | 1.62E-01 | 3.33E-01 | 106.0125 | 77.175 | 4.67E-01 | 6.67E-01 | 1475.5 | 1622.5 | 2 |
| MgCl2 concentration (mM) | 0 | 3 | 5.27E-01 | 4.00E-01 | 65.95 | 82.975 | 9.97E-01 | 1.00E+00 | 1588.6667 | 1589 | 3 |
| MgCl2 concentration (mM) | 0 | 12 | 6.31E-01 | 1.00E+00 | 75.3375 | 107.2125 | 7.78E-01 | 1.00E+00 | 1511.5 | 1480 | 2 |
| MgCl2 concentration (mM) | 4 | 6 | 3.46E-01 | 6.67E-01 | 102.3 | 124.05 | 2.28E-01 | 3.33E-01 | 1517.5 | 1398 | 2 |
| MgCl2 concentration (mM) | 4 | 9 | 2.52E-02 | 3.33E-01 | 102.3 | 211.875 | 5.08E-01 | 6.67E-01 | 1517.5 | 1563.5 | 2 |
| MgCl2 concentration (mM) | 4 | 12 | 9.44E-05 | 1.30E-04 | 91.395 | 198.795 | 3.07E-01 | 2.47E-01 | 1918.8 | 1753.9 | 10 |
| MgCl2 concentration (mM) | 4 | 15 | 3.32E-01 | 3.33E-01 | 102.3 | 130.875 | 3.81E-01 | 6.67E-01 | 1517.5 | 1360 | 2 |
| MgCl2 concentration (mM) | 6 | 9 | 5.94E-01 | 6.86E-01 | 154.5938 | 178.1625 | 3.80E-03 | 2.86E-02 | 1390.75 | 1607 | 4 |
| MgCl2 concentration (mM) | 6 | 12 | 8.77E-01 | 7.30E-01 | 127.0167 | 132.9417 | 4.77E-01 | 2.58E-01 | 1709.7778 | 1845.8889 | 9 |
| MgCl2 concentration (mM) | 6 | 15 | 4.50E-01 | 8.41E-01 | 140.52 | 113.79 | 7.04E-01 | 5.48E-01 | 1443 | 1477 | 5 |
| MgCl2 concentration (mM) | 9 | 12 | 8.71E-01 | 6.86E-01 | 178.1625 | 170.8125 | 8.05E-01 | 8.86E-01 | 1607 | 1582.25 | 4 |
| MgCl2 concentration (mM) | 9 | 15 | 1.17E-01 | 2.00E-01 | 178.1625 | 124.7062 | 1.24E-01 | 2.00E-01 | 1607 | 1448 | 4 |

TABLE S1-continued

Tables of cDNA library yield and length starting with purified total RNA

| MgCl2 concentration (mM) | betaine concentration (M) | betaine concentration (M) | betaine concentration (M) | betaine concentration (M) | RT enzyme | RT enzyme | RT enzyme | RT enzyme | RT protocol | | | | | | | | |
|---|---|---|---|---|---|---|---|---|---|---|---|---|---|---|---|---|---|
| 12 | 15 | | | | | | | | | 2.94E-01 | 3.43E-01 | 170.8125 | 124.7062 | 2.87E-01 | 3.43E-01 | 1582.25 | 1448 | 4 |
| 0 | 0.6 | | | | | | | | | 7.74E-01 | 6.86E-01 | 80.6063 | 73.725 | 3.70E-02 | 1.14E-01 | 1690.75 | 1540.5 | 4 |
| 0 | 1 | | | | | | | | | 1.61E-01 | 1.65E-01 | 51.93 | 81.2025 | 3.55E-01 | 2.18E-01 | 2127.8 | 2006.9 | 10 |
| 0.6 | 1 | | | | | | | | | 4.49E-01 | 1.00E+00 | 87.1 | 69.875 | 7.58E-01 | 1.00E+00 | 1618.3333 | 1596.6667 | 3 |
| 1 | 1.5 | | | | | | | | | 7.73E-01 | 3.43E-01 | 101.215 | 86.115 | 8.82E-01 | 6.86E-01 | 2409.5 | 2430.5 | 4 |
| Maxima H-Revertaid Premium | | | | | | | | | | 1.92E-02 | 3.33E-01 | 192 | 15.6375 | 1.66E-01 | 3.33E-01 | 1696 | 1603.5 | 2 |
| Revertaid H-SMARTscribe | | | | | | | | | | 2.47E-02 | 4.11E-02 | 148.2125 | 222.375 | 9.03E-02 | 1.32E-01 | 1423 | 1552.8333 | 6 |
| SSRTII | | | | | | | | | | — | — | 15.9 | 19.65 | — | — | 1669 | 1683 | 1 |
| SSRTII | | | | | | | | | | 1.21E-06 | 1.55E-04 | 252.3094 | 9.7031 | 8.59E-01 | 6.74E-01 | 1637.125 | 1618.875 | 8 |
| SSRTIII | | | | | | | | | | 1.47E-01 | 3.33E-01 | 73.95 | 43.05 | 5.70E-01 | 1.00E+00 | 1628 | 1577.5 | 2 |
| 60@42 C., then 90@60 C. | | | | | | | | | | 1.50E-01 | 3.33E-01 | 73.95 | 107.3625 | 3.70E-01 | 3.33E-01 | 1628 | 1719 | 2 |
| 60@42 C., then 90@60 C. | | | | | | | | | | | | | | | | | | |
| 60@50 C., then 30@60 C., then 30@42 C. | | | | | | | | | | 5.90E-02 | 2.00E-01 | 55.7437 | 110.7375 | 1.58E-01 | 1.46E-01 | 1515 | 1629 | 4 |
| 60@42 C., then 30@60 C., then 30@42 C. | | | | | | | | | | | | | | | | | | |
| 90@42 C., then 10x (2@50 C.-2@42 C.) | | | | | | | | | | 3.09E-01 | 3.43E-01 | 173.1562 | 235.8 | 6.43E-01 | 4.86E-01 | 1877.5 | 1973 | 4 |
| 90@42 C., then 10x (2@42 C.) | | | | | | | | | | 6.72E-02 | 3.33E-01 | 101.55 | 109.8375 | 1.90E-01 | 3.33E-01 | 2075 | 2226 | 2 |
| 90@42 C., then 10x (2@55 C.-2@42 C.) | | | | | | | | | | 8.90E-01 | 4.00E-01 | 158.45 | 170.475 | 6.57E-01 | 4.00E-01 | 1924.3333 | 2025.3333 | 3 |
| 90@42 C., then 10x (2@60 C.-2@42 C.) | | | | | | | | | | 4.30E-01 | 6.67E-01 | 244.7625 | 278.1375 | 6.57E-01 | 6.67E-01 | 1680 | 1644.5 | 2 |
| 90@42 C., then 15x (2@50 C.-2@42 C.) | | | | | | | | | | | | | | | | | | |

TABLE S1-continued

Tables of cDNA library yield and length starting with purified total RNA

| | | | | | | | | | | |
|---|---|---|---|---|---|---|---|---|---|---|
| RT protocol | 90@42 C. | 90@42 C., then 20x (2@50 C.-2@42 C.) | 8.51E-01 | 6.67E-01 | 244.7625 | 237.225 | 1.20E-01 | 3.33E-01 | 1680 | 1467 | 2 |
| RT protocol | 90@42 C. | 90@42 C., then 5x (2@50 C.-2@42 C.) | 2.86E-01 | 3.33E-01 | 244.7625 | 297.7125 | 4.87E-01 | 6.67E-01 | 1680 | 1738.5 | 2 |
| RT protocol | 90@42 C., then 10x (2@50 C.-2@42 C.) | 90@42 C., then 10x (2@55 C.-2@42 C.) | 5.04E-03 | 1.00E-01 | 165.375 | 105.925 | 5.96E-01 | 1.00E+00 | 2248.6667 | 2227.6667 | 3 |
| RT protocol | 90@42 C., then 10x (2@50 C.-2@42 C.) | 90@42 C., then 10x (2@60 C.-2@42 C.) | 5.23E-01 | 4.21E-01 | 206.295 | 175.17 | 9.27E-01 | 5.48E-01 | 2031.2 | 2015.4 | 5 |
| RT protocol | 90@42 C., then 10x (2@50 C.-2@42 C.) | 90@42 C., then 15x (2@50 C.-2@42 C.) | 7.32E-01 | 1.00E+00 | 291.125 | 300.3 | 1.71E-01 | 2.00E-01 | 1722.3333 | 1639.6667 | 3 |
| RT protocol | 90@42 C., then 10x (2@50 C.-2@42 C.) | 90@42 C., then 20x (2@50 C.-2@42 C.) | 4.97E-01 | 4.00E-01 | 246.875 | 196.375 | 7.32E-02 | 1.00E-01 | 1714 | 1521 | 3 |
| RT protocol | 90@42 C., then 10x (2@50 C.-2@42 C.) | 90@42 C., then 5x (2@50 C.-2@42 C.) | 9.92E-01 | 1.00E+00 | 291.125 | 291.25 | 5.65E-01 | 7.00E-01 | 1722.3333 | 1752.6667 | 3 |
| RT protocol | 90@42 C., then 10x (2@55 C.-2@42 C.) | 90@42 C., then 10x (2@60 C.-2@42 C.) | 2.69E-01 | 4.00E-01 | 105.925 | 114.775 | 2.23E-01 | 4.00E-01 | 2227.6667 | 2172.3333 | 3 |
| RT protocol | 90@42 C., then 10x (2@60 C.-2@42 C.) | 90@42 C., then 15x (2@50 C.-2@42 C.) | — | — | 286.2 | 285.3 | — | — | 1732 | 1610 | 1 |
| RT protocol | 90@42 C., then 10x (2@60 C.-2@42 C.) | 90@42 C., then 20x (2@50 C.-2@42 C.) | — | — | 286.2 | 259.275 | — | — | 1732 | 1525 | 1 |
| RT protocol | 90@42 C., then 10x (2@60 C.-2@42 C.) | 90@42 C., then 5x (2@50 C.-2@42 C.) | — | — | 286.2 | 306.075 | — | — | 1732 | 1706 | 1 |
| RT protocol | 90@42 C., then 15x (2@50 C.-2@42 C.) | 90@42 C., then 20x (2@50 C.-2@42 C.) | 2.94E-01 | 3.33E-01 | 278.1375 | 237.225 | 1.47E-01 | 3.33E-01 | 1644.5 | 1467 | 2 |
| RT protocol | 90@42 C., then 15x (2@50 C.-2@42 C.) | 90@42 C., then 5x (2@50 C.-2@42 C.) | 7.35E-01 | 1.00E+00 | 300.3 | 291.25 | 2.30E-02 | 1.00E-01 | 1639.6667 | 1752.6667 | 3 |

TABLE S1-continued

Tables of cDNA library yield and length starting with purified total RNA

| Category | Condition | | | | | | | | | |
|---|---|---|---|---|---|---|---|---|---|---|
| RT protocol | 2@42 C., 90@42 C., then 20x (2@50 C.-2@42 C.) | 1.90E-01 | 3.33E-01 | 237.225 | 297.7125 | 8.13E-02 | 3.33E-01 | 1467 | 1738.5 | 2 |
| RT protocol | 2@42 C., 90@42 C., then 5x (2@50 C.-2@42 C.) | 3.50E-03 | 7.94E-03 | 62.595 | 12.24 | 2.09E-01 | 1.51E-01 | 2146.2 | 2051 | 5 |
| RT protocol | 90@55 C. | — | — | 164.4 | 6 | — | — | 1858 | 1933 | 1 |
| RT protocol | 90@60 C. | 6.44E-01 | 7.55E-01 | 186.6375 | 171.0125 | 5.18E-01 | 5.90E-01 | 1929.4167 | 2029.5 | 12 |
| PCR enzyme | Advantage 2 Pol. | 4.33E-01 | 4.86E-01 | 212.3625 | 182.6813 | 8.11E-01 | 3.43E-01 | 1701 | 1722.75 | 4 |
| PCR enzyme | Advantage 2 Pol. | 5.85E-02 | 2.86E-02 | 212.3625 | 133.8562 | 6.29E-01 | 3.43E-01 | 1701 | 1743.75 | 4 |
| PCR enzyme | Advantage 2 Pol. | 2.60E-01 | 3.43E-01 | 223.725 | 182.6813 | 7.49E-01 | 8.86E-01 | 1702 | 1722.75 | 4 |
| PCR enzyme | KAPA HiFi HS | 2.99E-02 | 2.86E-02 | 223.725 | 133.8562 | 4.93E-01 | 8.86E-01 | 1702 | 1743.75 | 4 |
| PCR enzyme | KAPA HiFi HS | 1.25E-01 | 1.14E-01 | 182.683 | 133.8562 | 5.99E-01 | 8.86E-01 | 1722.75 | 1743.75 | 4 |
| PCR enzyme | Phusion HS | 6.77E-01 | 6.05E-01 | 186.85 | 203.225 | 3.44E-01 | 3.87E-01 | 2022.2222 | 1875.4444 | 9 |
| PCR enzyme purification | Q5 NEB | 4.55E-03 | 1.37E-02 | 193.6781 | 134.3812 | 3.44E-04 | 5.55E-05 | 1709.4167 | 2008.0833 | 24 |
| dNTPs added in the beginning | yes | 6.89E-04 | 1.00E-01 | 291.125 | 103.95 | 3.50E-03 | 1.00E-01 | 1722.3333 | 1093 | 3 |
| other additives | 0.816M 1,2 propandiol | 1.82E-01 | 3.33E-01 | 299.025 | 178.4625 | 9.93E-02 | 3.33E-01 | 1707 | 1421.5 | 2 |
| other additives | 1.075M ethylene glycol | 1.10E-01 | 3.33E-01 | 56.535 | 28.095 | 1.13E-01 | 3.33E-01 | 1930 | 1479.5 | 2 |
| other additives | 3 mM MnCl2 | 1.05E-01 | 3.33E-01 | 56.535 | 16.95 | 1.03E-01 | 3.33E-01 | 1930 | 1213 | 2 |
| other additives | 6 mM MnCl2 | 8.18E-01 | 6.86E-01 | 77.0625 | 72.3563 | 4.45E-01 | 4.86E-01 | 1679 | 1634.25 | 4 |
| other additives | 0.6M trehalose | 2.82E-01 | 3.33E-01 | 104.4375 | 178.4625 | 3.99E-02 | 3.33E-01 | 1095 | 1421.5 | 2 |
| other additives | 1.075M ethylene glycol | 1.45E-01 | 3.33E-01 | 28.095 | 16.95 | 1.46E-01 | 3.33E-01 | 1479.5 | 1213 | 2 |

TABLE S2

List of all template switching oligonucleotides tested.

| TSO name | Sequence (5'->3') | 5'-end blocking groups | 5'-end modifications | 3'-end modifications | 3'-end blocking groups |
|---|---|---|---|---|---|
| 2OMe | AAGCAGTGGTATCAACGCAGAGTACrGrGrGmG | — | — | 3 Riboguanosines + 1 Guanosine | 2O'-Methyl |
| C6 Amino | AAGCAGTGGTATCAACGCAGAGTACATrGrGrG | — | — | 3 Riboguanosines | Aminolink C6 |
| ddC | AAGCAGTGGTATCAACGCAGAGTACrGrGrGrGddC | — | — | 4 Riboguanosines + 1 Dideoxycytosine | — |
| dGCGGG | AAGCAGTGGTATCAACGCAGAGTACGCGGG | — | — | 1 Guanosine + 1 Cytosine + 3 Guanosines | — |
| dGCGGGp | AAGCAGTGGTATCAACGCAGAGTACGCGGG | — | — | 1 Guanosine + 1 Cytosine + 3 Guanosines | Phosphate |
| ISO | iGiCiGAAGCAGTGGTATCAACGCAGAGTACrGrGrCrGrGrG | Methyl C5 | isoGuanosine-isoCytosine-isoGuanosine | 1 Riboguanosine + 1 Ribocytosine + 3 Riboguanosines | Phosphate |
| rGrG + G | AAGCAGTGGTATCAACGCAGAGTACrGrG + G | — | — | 2 Riboguanosines + 1 LNA-modified Guanosine | — |
| rGrG + N | AAGCAGTGGTATCAACGCAGAGTACrGrG + N | — | — | 2 Riboguanosines + 1 LNA-modified nucleotide (any) | — |
| +G + G + G | AAGCAGTGGTATCAACGCAGAGTAC + G + G + G | — | — | 3 LNA-modified Guanosines | — |
| rG + G + G | AAGCAGTGGTATCAACGCAGAGTACrG + G + G | — | — | 2 LNA-modified Guanosines | — |
| rGrGrG | AAGCAGTGGTATCAACGCAGAGTACATrGrGrG | — | — | 3 Riboguanosines | — |
| rG3p | AAGCAGTGGTATCAACGCAGAGTACATrGrGrGp | — | — | 3 Riboguanosines | Phosphate |
| rG5 | AAGCAGTGGTATCAACGCAGAGTACrGrGrGrGrG | — | — | 5 Riboguanosines | — |

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_2 | HEK293T | H. sapiens | 10.778 | 1099 | rGrG + G | 1 | SSRTII | SMARTer dT30VN | 13 | 1 | yes | Advantage | 50 | Could be a cell aggregate |
| HEK_3 | HEK293T | H. sapiens | 9.596 | 1142 | rGrG + G | 1 | SSRTII | SMARTer dT30VN | 14 | 1 | yes | Advantage | 50 | Could be a cell aggregate |
| HEK_4 | HEK293T | H. sapiens | 1.160 | 1098 | rGrG + G | 1 | SSRTII | SMARTer dT30VN | 15 | 1 | yes | Advantage | 50 | |
| HEK_5 | HEK293T | H. sapiens | 0.590 | 1203 | rGrG + G | 1 | SSRTII | SMARTer dT30VN | 16 | 1 | yes | Advantage | 50 | |
| HEK_6 | HEK293T | H. sapiens | 2.210 | 1175 | rGrG + G | 1 | SSRTII | SMARTer dT30VN | 17 | 1 | yes | Advantage | 50 | |
| HEK_7 | HEK293T | H. sapiens | 0.410 | 1136 | rGrG + G | 1 | SSRTII | SMARTer dT30VN | 18 | 1 | yes | Advantage | 50 | |
| HEK_8 | HEK293T | H. sapiens | 4.184 | 1146 | rGrG + G | 1 | SSRTII | SMARTer dT30VN | 19 | 1 | yes | Advantage | 50 | Could be a cell aggregate |
| HEK_9 | HEK293T | H. sapiens | 0.840 | 1141 | rGrG + G | 1 | SSRTII | SMARTer dT30VN | 20 | 1 | yes | Advantage | 50 | |
| HEK_10 | HEK293T | H. sapiens | 1.130 | 1088 | rGrG + G | 1 | SSRTII | SMARTer dT30VN | 21 | 1 | yes | Advantage | 50 | Could be a cell aggregate |
| HEK_12 | HEK293T | H. sapiens | 9.095 | 1106 | rGrG + G | 1 | SSRTII | SMARTer dT30VN | 23 | 1 | yes | Advantage | 50 | |
| HEK_13 | HEK293T | H. sapiens | 0.490 | 1017 | rGrG + G | 1 | SSRTII | SMARTer dT30VN | 24 | 1 | yes | Advantage | 50 | Could be a cell aggregate |
| HEK_14 | HEK293T | H. sapiens | 3.640 | 1046 | rGrG + G | 1 | SSRTII | SMARTer dT30VN | 25 | 1 | yes | Advantage | 50 | Could be a cell aggregate |
| HEK_16 | HEK293T | H. sapiens | 17.225 | 1072 | rGrG + G | 1 | SSRTII | SMARTer dT30VN | 27 | 1 | yes | Advantage | 50 | Could be a cell aggregate |
| HEK_SMRT_1 | HEK293T | H. sapiens | 0.760 | 1429 | SMARTer Oligo IIA | 1 | SMARTscribe | SMARTer dT30VN | 6 | 1 | yes | Advantage | 50 | |
| HEK_SMRT_2 | HEK293T | H. sapiens | 2.304 | 1411 | SMARTer Oligo IIA | 1 | SMARTscribe | SMARTer dT30VN | 6 | 1 | yes | Advantage | 50 | |
| HEK_SMRT_3 | HEK293T | H. sapiens | 1.544 | 1424 | SMARTer Oligo IIA | 1 | SMARTscribe | SMARTer dT30VN | 6 | 1 | yes | Advantage | 50 | |
| HEK_SMRT_4 | HEK293T | H. sapiens | 0.422 | 1457 | SMARTer Oligo IIA | 1 | SMARTscribe | SMARTer dT30VN | 6 | 1 | yes | Advantage | 50 | |
| HEK_18 | HEK293T | H. sapiens | 0.208 | 1384 | rGrGrG | 1 | SSRTII | SMARTer dT30VN | 12 | 1 | yes | Advantage | 50 | 40 u SSRT II |
| HEK_19 | HEK293T | H. sapiens | 0.512 | 1541 | rGrGrG | 1 | SSRTII | SMARTer dT30VN | 12 | 1 | yes | Advantage | 50 | 40 u SSRT II |
| HEK_20 | HEK293T | H. sapiens | 0.550 | 1614 | rGrGrG | 1 | SSRTII | SMARTer dT30VN | 12 | 1 | yes | Advantage | 50 | 40 u SSRT II |
| HEK_21 | HEK293T | H. sapiens | 0.240 | 1492 | rGrGrG | 1 | SSRTII | SMARTer dT30VN | 12 | 1 | yes | Advantage | 50 | 40 u SSRT II |
| HEK_22 | HEK293T | H. sapiens | 0.957 | 1222 | rGrGrG | 1 | SSRTII | SMARTer dT30VN | 12 | 1 | yes | Advantage | 50 | 40 u SSRT II |
| HEK_23 | HEK293T | H. sapiens | 0.872 | 1392 | rGrGrG | 1 | SSRTII | SMARTer dT30VN | 12 | 1 | yes | Advantage | 50 | 40 u SSRT II |
| HEK_24 | HEK293T | H. sapiens | 0.315 | 1326 | rGrGrG | 1 | SSRTII | SMARTer dT30VN | 12 | 1 | yes | Advantage | 50 | 40 u SSRT II |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_25 | HEK293T | H. sapiens | 0.462 | 1474 | rGrG + G | 1 | SSRTII | dT30VN | 12 | 1 | yes | Advantage | 50 | |
| HEK_26 | HEK293T | H. sapiens | 0.248 | 1441 | rGrG + G | 1 | SSRTII | SMARTer | 12 | 1 | yes | Advantage | 50 | |
| HEK_27 | HEK293T | H. sapiens | 0.244 | 1487 | rGrG + G | 1 | SSRTII | dT30VN | 12 | 1 | yes | Advantage | 50 | |
| HEK_28 | HEK293T | H. sapiens | 0.262 | 1496 | rGrG + G | 1 | SSRTII | SMARTer | 12 | 1 | yes | Advantage | 50 | |
| HEK_29 | HEK293T | H. sapiens | 0.761 | 1402 | rGrG + G | 1 | SSRTII | dT30VN | 12 | 1 | yes | Advantage | 50 | |
| HEK_31 | HEK293T | H. sapiens | 0.594 | 1583 | rGrG + G | 1 | SSRTII | SMARTer | 12 | 1 | yes | Advantage | 50 | |
| HEK_32 | HEK293T | H. sapiens | 0.457 | 1347 | rGrG + G | 1 | SSRTII | dT30VN | 12 | 1 | yes | Advantage | 50 | |
| HEK_33 | HEK293T | H. sapiens | 0.473 | 1507 | rGrG + G | 1 | SSRTII | SMARTer | 12 | 1 | yes | Advantage | 50 | |
| HEK_34 | HEK293T | H. sapiens | 0.315 | 1501 | rGrG + G | 1 | SSRTII | dT30VN | 12 | 1 | yes | Advantage | 50 | |
| HEK_35 | HEK293T | H. sapiens | 0.744 | 1917 | rGrG + G | 1 | SSRTII | SMARTer | 12 | 1 | — | Advantage | 50 | |
| HEK_37 | HEK293T | H. sapiens | 1.531 | 1626 | rGrG + G | 1 | SSRTII | dT30VN | 12 | 1 | — | Advantage | 50 | |
| HEK_38 | HEK293T | H. sapiens | 0.344 | 1870 | rGrG + G | 1 | SSRTII | SMARTer | 12 | 1 | — | Advantage | 50 | |
| HEK_39 | HEK293T | H. sapiens | 0.453 | 1968 | rGrG + G | 1 | SSRTII | dT30VN | 12 | 1 | — | Advantage | 50 | |
| HEK_40 | HEK293T | H. sapiens | 0.580 | 1958 | rGrG + G | 1 | SSRTII | SMARTer | 12 | 1 | — | Advantage | 50 | |
| HEK_41 | HEK293T | H. sapiens | 0.382 | 1202 | rGrG + G | 1 | SSRTII | dT30VN | 12 | 1 | yes | Advantage | 50 | |
| HEK_42 | HEK293T | H. sapiens | 0.392 | 1288 | rGrG + G | 1 | SSRTII | SMARTer | 12 | 1 | yes | Advantage | 50 | |
| HEK_43 | HEK293T | H. sapiens | 0.844 | 1319 | rGrG + G | 1 | SSRTII | dT30VN | 12 | 1 | yes | Advantage | 50 | |
| HEK_44 | HEK293T | H. sapiens | 0.582 | 1452 | rGrG + G | 1 | SSRTII | SMARTer | 12 | 1 | yes | Advantage | 50 | |
| HEK_45 | HEK293T | H. sapiens | 0.682 | 1312 | rGrG + G | 1 | SSRTII | dT30VN | 12 | 1 | yes | Advantage | 50 | |
| HEK_46 | HEK293T | H. sapiens | 0.692 | 1411 | rGrG + G | 1 | SSRTII | SMARTer | 12 | 1 | yes | Advantage | 50 | |
| HEK_47 | HEK293T | H. sapiens | 0.716 | 1337 | rGrGrG | 1 | SSRTII | dT30VN | 12 | 1 | yes | Advantage | 50 | |
| HEK_48 | HEK293T | H. sapiens | 0.578 | 1391 | rGrGrG | 1 | SSRTII | SMARTer | 12 | 1 | yes | Advantage | 50 | |
| HEK_49 | HEK293T | H. sapiens | 2.681 | 1440 | rGrGrG | 1 | SSRTII | dT30VN | 12 | 1 | yes | Advantage | 50 | Could be a cell aggregate |
| HEK_50 | HEK293T | H. sapiens | 1.158 | 1507 | rGrGrG | 1 | SSRTII | SMARTer | 12 | 1 | yes | Advantage | 50 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_51 | HEK293T | H. sapiens | 0.710 | 1389 | rGrGrG | 1 | SSRTII | dT30VN | 12 | 1 | yes | Advantage | 50 | |
| HEK_52 | HEK293T | H. sapiens | 1.050 | 1463 | rGrGrG | 1 | SSRTII | SMARTer dT30VN | 12 | 1 | yes | Advantage | 50 | |
| HEK_53 | HEK293T | H. sapiens | 0.714 | 1384 | rGrGrG | 1 | SSRTII | SMARTer dT30VN | 12 | 1 | yes | Advantage | 50 | |
| HEK_54 | HEK293T | H. sapiens | 0.637 | 1509 | rGrGrG | 1 | SSRTII | SMARTer dT30VN | 12 | 1 | yes | Advantage | 50 | |
| HEK_55 | HEK293T | H. sapiens | 1.338 | 1873 | rGrGrG | 1 | SSRTII | SMARTer dT30VN | 12 | 1 | — | KAPA HiFi HS | 50 | |
| HEK_56 | HEK293T | H. sapiens | 1.258 | 1846 | rGrGrG | 1 | SSRTII | SMARTer dT30VN | 12 | 1 | — | KAPA HiFi HS | 50 | |
| HEK_57 | HEK293T | H. sapiens | 3.012 | 1798 | rGrG + G | 1 | SSRTII | SMARTer dT30VN | 12 | 1 | — | KAPA HiFi HS | 50 | |
| HEK_58 | HEK293T | H. sapiens | 1.763 | 1734 | rGrG + G | 1 | SSRTII | SMARTer dT30VN | 12 | 1 | — | Advantage | 50 | |
| HEK_59 | HEK293T | H. sapiens | 2.837 | 1833 | rGrGrG | 1 | SSRTII | SMARTer dT30VN | 12 | 1 | — | Advantage | 50 | |
| HEK_60 | HEK293T | H. sapiens | 1.889 | 1758 | rGrGrG | 1 | SSRTII | SMARTer dT30VN | 12 | 1 | — | Advantage | 50 | |
| HEK_61 | HEK293T | H. sapiens | 3.733 | 1841 | rGrG + G | 1 | SSRTII | SMARTer dT30VN | 12 | 1 | — | Advantage | 50 | |
| HEK_62 | HEK293T | H. sapiens | 2.430 | 1849 | rGrG + G | 1 | SSRTII | SMARTer dT30VN | 12 | 1 | — | Advantage | 50 | |
| HEK_63 | HEK293T | H. sapiens | 0.758 | 1845 | rGrGrG | 1 | SSRTII | SMARTer dT30VN | 12 | 1 | — | KAPA HiFi HS | 50 | |
| HEK_64 | HEK293T | H. sapiens | 0.948 | 1907 | rGrGrG | 1 | SSRTII | SMARTer dT30VN | 12 | 1 | — | KAPA HiFi HS | 50 | |
| HEK_65 | HEK293T | H. sapiens | 1.364 | 1837 | rGrGrG | 1 | SSRTII | SMARTer dT30VN | 12 | 1 | — | KAPA HiFi HS | 50 | |
| HEK_66 | HEK293T | H. sapiens | 1.897 | 1821 | rGrGrG | 1 | SSRTII | SMARTer dT30VN | 12 | 1 | — | KAPA HiFi HS | 50 | |
| HEK_67 | HEK293T | H. sapiens | 2.721 | 1746 | rGrG + G | 1 | SSRTII | SMARTer dT30VN | 12 | 1 | — | KAPA HiFi HS | 50 | |
| HEK_68 | HEK293T | H. sapiens | 5.123 | 1699 | rGrGrG | 1 | SSRTII | SMARTer dT30VN | 12 | 1 | — | KAPA HiFi HS | 50 | Could be a cell aggregate |
| HEK_69 | HEK293T | H. sapiens | 2.499 | 1892 | rGrG + G | 1 | SSRTII | SMARTer dT30VN | 12 | 1 | — | KAPA HiFi HS | 50 | |
| HEK_70 | HEK293T | H. sapiens | 1.632 | 1715 | rGrG + G | 1 | SSRTII | SMARTer dT30VN | 12 | 1 | — | KAPA HiFi HS | 50 | |
| HEK_71 | HEK293T | H. sapiens | 2.614 | 1438 | rGrG + G | 1 | SSRTII | SMARTer dT30VN | 12 | 1 | yes | Advantage | 50 | |
| HEK_72 | HEK293T | H. sapiens | 1.343 | 1535 | rGrG + G | 1 | SSRTII | SMARTer dT30VN | 12 | 1 | yes | Advantage | 50 | |
| HEK_73 | HEK293T | H. sapiens | 2.618 | 1570 | rGrG + G | 1 | SSRTII | SMARTer dT30VN | 12 | 1 | yes | Advantage | 50 | |
| HEK_74 | HEK293T | H. sapiens | 2.037 | 1611 | rGrG + G | 1 | SSRTII | SMARTer dT30VN | 12 | 1 | yes | Advantage | 50 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_75 | HEK293T | H. sapiens | 1.862 | 1494 | rGrGrG | 1 | SSRTII | dT30VN | 12 | 1 | yes | Advantage | 50 | |
| HEK_76 | HEK293T | H. sapiens | 0.560 | 1567 | rGrGrG | 1 | SSRTII | SMARTer dT30VN | 12 | 1 | yes | Advantage | 50 | |
| HEK_77 | HEK293T | H. sapiens | 1.609 | 1604 | rGrGrG | 1 | SSRTII | SMARTer dT30VN | 12 | 1 | yes | Advantage | 50 | |
| HEK_78 | HEK293T | H. sapiens | 0.748 | 1392 | rGrGrG | 1 | SSRTII | SMARTer dT30VN | 12 | 1 | yes | Advantage | 50 | |
| HEK_79 | HEK293T | H. sapiens | 2.876 | 2093 | rGrG + G | 1 | SSRTII | SMARTer dT30VN | 12 | 1 | — | Advantage | 50 | |
| HEK_80 | HEK293T | H. sapiens | 6.017 | 1975 | rGrG + G | 1 | SSRTII | SMARTer dT30VN | 12 | 1 | — | Advantage | 50 | Could be a cell aggregate |
| HEK_81 | HEK293T | H. sapiens | 5.110 | 1834 | rGrG + G | 1 | SSRTII | SMARTer dT30VN | 12 | 1 | — | Advantage | 50 | Could be a cell aggregate |
| HEK_82 | HEK293T | H. sapiens | 2.659 | 1912 | rGrG + G | 1 | SSRTII | SMARTer dT30VN | 12 | 1 | — | KAPA HiFi HS | 50 | |
| HEK_83 | HEK293T | H. sapiens | 3.820 | 1848 | rGrG + G | 1 | SSRTII | SMARTer dT30VN | 12 | 1 | — | KAPA HiFi HS | 50 | Could be a cell aggregate |
| HEK_84 | HEK293T | H. sapiens | 1.875 | 1941 | rGrG + G | 1 | SSRTII | SMARTer dT30VN | 12 | 1 | — | KAPA HiFi HS | 50 | |
| HEK_85 | HEK293T | H. sapiens | 4.477 | 2003 | rGrG + G | 1 | SSRTII | SMARTer dT30VN | 12 | 1 | — | KAPA HiFi HS | 50 | Could be a cell aggregate |
| HEK_86 | HEK293T | H. sapiens | 4.162 | 1784 | rGrG + G | 1 | SSRTII | SMARTer dT30VN | 12 | 1 | — | Advantage | 50 | |
| HEK_87 | HEK293T | H. sapiens | 0.539 | 1964 | rGrG + G | 1 | Maxima H minus | SMARTer dT30VN | 12 | 1 | — | KAPA HiFi HS | 50 | |
| HEK_88 | HEK293T | H. sapiens | 0.526 | 1860 | rGrG + G | 1 | Maxima H minus | SMARTer dT30VN | 12 | 1 | — | KAPA HiFi HS | 50 | |
| HEK_89 | HEK293T | H. sapiens | 0.288 | 1881 | rGrG + G | 1 | Maxima H minus | SMARTer dT30VN | 12 | 1 | — | KAPA HiFi HS | 50 | |
| HEK_90 | HEK293T | H. sapiens | 0.650 | 1560 | rGrG + G | 1 | Maxima H minus | SMARTer dT30VN | 12 | 1 | — | KAPA HiFi HS | 50 | |
| HEK_91 | HEK293T | H. sapiens | 0.341 | 1852 | rGrG + N | 1 | SSRTII | SMARTer dT30 | 12 | 1 | — | KAPA HiFi HS | 50 | |
| HEK_92 | HEK293T | H. sapiens | 0.354 | 1783 | rGrG + N | 1 | SSRTII | SMARTer dT30 | 12 | 1 | — | KAPA HiFi HS | 50 | |
| HEK_93 | HEK293T | H. sapiens | 1.520 | 1939 | rGrG + N | 1 | SSRTII | SMARTer dT30 | 12 | 1 | — | KAPA HiFi HS | 50 | |
| HEK_94 | HEK293T | H. sapiens | 1.722 | 1740 | rGrG + N | 1 | SSRTII | SMARTer dT30VN | 12 | 1 | — | KAPA HiFi HS | 50 | |
| HEK_95 | HEK293T | H. sapiens | 0.485 | 1740 | rGrG + N | 1 | SSRTII | SMARTer dT30VN | 12 | 1 | — | KAPA HiFi HS | 50 | |
| HEK_96 | HEK293T | H. sapiens | 1.090 | 1833 | rGrG + N | 1 | SSRTII | SMARTer dT30VN | 12 | 1 | — | KAPA HiFi HS | 50 | |
| HEK_97 | HEK293T | H. sapiens | 2.856 | 1731 | rGrG + N | 2 | SSRTII | SMARTer dT30VN | 12 | 1 | — | KAPA HiFi HS | 50 | |
| HEK_98 | HEK293T | H. sapiens | 2.776 | 1881 | rGrG + N | 2 | SSRTII | SMARTer dT30VN | 12 | 1 | — | KAPA HiFi HS | 50 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_99 | HEK293T | H. sapiens | 1.954 | 1730 | rGrG + N | 2 | SSRTII | dT30VN | 12 | 1 | — | HiFi HS | 50 | |
| HEK_100 | HEK293T | H. sapiens | 2.836 | 1909 | rGrG + N | 2 | SSRTII | SMARTer | 12 | 1 | — | KAPA HiFi HS | 50 | |
| HEK_101 | HEK293T | H. sapiens | 2.266 | 1750 | rGrG + G | 2 | SSRTII | dT30VN | 12 | 1 | — | KAPA HiFi HS | 50 | |
| HEK_102 | HEK293T | H. sapiens | 1.530 | 1850 | rGrG + G | 2 | SSRTII | SMARTer | 12 | 1 | — | KAPA HiFi HS | 50 | |
| HEK_103 | HEK293T | H. sapiens | 1.883 | 1703 | rGrG + G | 2 | SSRTII | dT30VN | 12 | 1 | — | KAPA HiFi HS | 50 | |
| HEK_105 | HEK293T | H. sapiens | 4.105 | 1929 | rGrG + G | 2 | SSRTII | SMARTer | 12 | 1 | — | KAPA HiFi HS | 50 | Could be a cell aggregate |
| HEK_106 | HEK293T | H. sapiens | 2.580 | 2009 | rGrG + G | 2 | SSRTII | dT30VN | 12 | 1 | — | KAPA HiFi HS | 50 | |
| HEK_107 | HEK293T | H. sapiens | 2.572 | 1910 | rGrG + G | 2 | SSRTII | SMARTer | 12 | 1 | — | KAPA HiFi HS | 50 | |
| HEK_108 | HEK293T | H. sapiens | 1.496 | 1973 | rGrG + G | 2 | SSRTII | dT30VN | 12 | 1 | — | KAPA HiFi HS | 50 | |
| HEK_109 | HEK293T | H. sapiens | 3.459 | 1908 | rGrG + G | 2 | SSRTII | SMARTer | 12 | 1 | — | KAPA HiFi HS | 50 | Could be a cell aggregate |
| HEK_110 | HEK293T | H. sapiens | 4.591 | 1921 | rGrG + G | 2 | SSRTII | dT30VN | 12 | 1 | — | Advantage | 50 | Could be a cell aggregate |
| HEK_111 | HEK293T | H. sapiens | 3.841 | 1972 | rGrG + G | 2 | SSRTII | SMARTer | 12 | 1 | — | Advantage | 50 | Could be a cell aggregate |
| HEK_112 | HEK293T | H. sapiens | 4.279 | 1916 | rGrG + G | 2 | SSRTII | dT30VN | 12 | 1 | — | KAPA HiFi HS | 50 | |
| HEK_113 | HEK293T | H. sapiens | 2.123 | 1648 | rGrG + G | 2 | SSRTII | SMARTer | 12 | 1 | — | KAPA HiFi HS | 50 | |
| HEK_114 | HEK293T | H. sapiens | 2.526 | 1845 | rGrG + G | 2 | SSRTII | dT30VN | 12 | 1 | — | KAPA HiFi HS | 50 | |
| HEK_115 | HEK293T | H. sapiens | 2.084 | 1569 | rGrG + N | 2 | SSRTII | SMARTer | 12 | 1 | — | KAPA HiFi HS | 50 | |
| HEK_116 | HEK293T | H. sapiens | 0.511 | 1628 | rGrG + N | 2 | SSRTII | dT30VN | 12 | 1 | — | KAPA HiFi HS | 50 | |
| HEK_117 | HEK293T | H. sapiens | 2.690 | 1823 | rGrG + N | 2 | SSRTII | SMARTer | 12 | 1 | — | Advantage | 50 | |
| HEK_118 | HEK293T | H. sapiens | 1.454 | 1774 | rGrG + N | 2 | SSRTII | dT30VN | 12 | 1 | — | Advantage | 50 | |
| HEK_119 | HEK293T | H. sapiens | 0.361 | 1598 | rGrG + N | 2 | SSRTII | SMARTer | 12 | 1 | — | Advantage | 50 | |
| HEK_120 | HEK293T | H. sapiens | 1.215 | 1935 | rGrG + N | 2 | SSRTII | dT30VN | 12 | 1 | — | KAPA HiFi HS | 50 | |
| HEK_121 | HEK293T | H. sapiens | 0.434 | 1682 | rGrG + N | 2 | SSRTII | SMARTer | 12 | 1 | — | KAPA HiFi HS | 50 | |
| HEK_122 | HEK293T | H. sapiens | 0.739 | 1553 | rGrG + N | 2 | SSRTII | dT30VN | 12 | 1 | — | KAPA HiFi HS | 50 | |
| HEK_123 | HEK293T | H. sapiens | 1.599 | 1688 | rGrG + N | 2 | SSRTII | SMARTer | 12 | 1 | — | KAPA | 50 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_124 | HEK293T | H. sapiens | 2.301 | 1617 | rGrG + N | 2 | SSRTII | dT30VN | 12 | 1 | — | HiFi HS | 50 | |
| HEK_135 | HEK293T | H. sapiens | 0.784 | 1810 | rGrG + G | 1 | SSRTII | SMARTer dT30VN | 12 | 1 | — | KAPA HiFi HS | 50 | 2x dCTP |
| HEK_136 | HEK293T | H. sapiens | 1.311 | 1990 | rGrG + G | 1 | SSRTII | SMARTer dT30VN | 12 | 1 | — | KAPA HiFi HS | 50 | 2x dCTP |
| HEK_137 | HEK293T | H. sapiens | 0.895 | 1829 | rGrG + G | 1 | SSRTII | SMARTer dT30VN | 12 | 1 | — | KAPA HiFi HS | 50 | 2x dCTP |
| HEK_138 | HEK293T | H. sapiens | 1.318 | 1948 | rGrG + G | 1 | SSRTII | SMARTer dT30VN | 12 | 1 | — | KAPA HiFi HS | 50 | 2x dCTP |
| HEK_139 | HEK293T | H. sapiens | 1.853 | 1704 | rGrG + G | 1 | SSRTII | SMARTer dT30VN | 12 | 1 | — | KAPA HiFi HS | 50 | 2x dCTP |
| HEK_140 | HEK293T | H. sapiens | 4.009 | 1833 | rGrG + G | 1 | SSRTII | SMARTer dT30VN | 12 | 1 | — | KAPA HiFi HS | 50 | 2x dCTP (NOT SINGLE CELL) |
| HEK_141 | HEK293T | H. sapiens | 5.230 | 1820 | rGrG + G | 1 | SSRTII | SMARTer dT30VN | 12 | 1 | — | KAPA HiFi HS | 50 | Could be a cell aggregate |
| HEK_144 | HEK293T | H. sapiens | 4.803 | 1766 | rGrG + G | 2 | SSRTII | SMARTer dT30VN | 12 | 1 | — | Advantage | 50 | Could be a cell aggregate |
| HEK_145 | HEK293T | H. sapiens | 2.166 | 1619 | rGrG + G | 2 | SSRTII | SMARTer dT30VN | 12 | 1 | — | Advantage | 50 | |
| HEK_146 | HEK293T | H. sapiens | 2.283 | 1552 | rGrG + G | 2 | SSRTII | SMARTer dT30VN | 12 | 1 | — | Advantage | 50 | |
| HEK_147 | HEK293T | H. sapiens | 2.099 | 1316 | rGrG + G | 2 | SSRTII | SMARTer dT30VN | 12 | 1 | — | Advantage | 50 | |
| HEK_148 | HEK293T | H. sapiens | 2.191 | 1339 | rGrG + G | 2 | SSRTII | SMARTer dT30VN | 12 | 1 | — | Advantage | 50 | HEDGEHOG PATTERN |
| HEK_149 | HEK293T | H. sapiens | 1.560 | 1426 | rGrG + G | 2 | SSRTII | SMARTer dT30VN | 12 | 1 | — | Advantage | 50 | |
| HEK_150 | HEK293T | H. sapiens | 2.830 | 1508 | rGrG + G | 2 | SSRTII | SMARTer dT30VN | 12 | 1 | — | Advantage | 50 | |
| HEK_151 | HEK293T | H. sapiens | 2.220 | 1220 | rGrG + G | 2 | SSRTII | SMARTer dT30VN | 12 | 1 | — | Advantage | 50 | |
| HEK_152 | HEK293T | H. sapiens | 2.654 | 1534 | rGrG + G | 2 | SSRTII | SMARTer dT30 | 12 | 1 | — | Advantage | 50 | HEDGEHOG PATTERN |
| HEK_153 | HEK293T | H. sapiens | 2.039 | 1655 | rGrG + G | 2 | SSRTII | SMARTer dT30 | 12 | 1 | — | Advantage | 50 | |
| HEK_154 | HEK293T | H. sapiens | 3.001 | 1837 | rGrG + G | 2 | SSRTII | SMARTer dT30 | 12 | 1 | — | Advantage | 50 | |
| HEK_155 | HEK293T | H. sapiens | 1.378 | 1846 | rGrG + G | 2 | SSRTII | SMARTer dT30 | 12 | 1 | — | Advantage | 50 | |
| HEK_156 | HEK293T | H. sapiens | 1.065 | 1853 | rGrG + G | 2 | SSRTII | SMARTer dT30 | 12 | 1 | — | Advantage | 50 | |
| HEK_157 | HEK293T | H. sapiens | 1.621 | 1772 | rGrG + G | 2 | SSRTII | SMARTer dT30 | 12 | 1 | — | Advantage | 50 | |
| HEK_158 | HEK293T | H. sapiens | 2.418 | 1706 | rGrG + G | 2 | SSRTII | SMARTer dT30 | 12 | 1 | — | Advantage | 50 | |

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_SMRT_5 | HEK293T | H. sapiens | 0.128 | 1495 | SMARTer Oligo IIA | 1 | SMARTscribe | SMARTer dT30VN | 6 | 1 | yes | Advantage | 50 | |
| HEK_SMRT_6 | HEK293T | H. sapiens | 0.042 | 1469 | SMARTer Oligo IIA | 1 | SMARTscribe | SMARTer dT30VN | 6 | 1 | yes | Advantage | 50 | |
| HEK_SMRT_7 | HEK293T | H. sapiens | 0.207 | 1359 | SMARTer Oligo IIA | 1 | SMARTscribe | SMARTer dT30VN | 6 | 1 | yes | Advantage | 50 | |
| HEK_SMRT_8 | HEK293T | H. sapiens | 0.246 | 1340 | SMARTer Oligo IIA | 1 | SMARTscribe | SMARTer dT30VN | 6 | 1 | yes | Advantage | 50 | |
| HEK_SMRT_9 | HEK293T | H. sapiens | 0.152 | 1455 | SMARTer Oligo IIA | 1 | SMARTscribe | SMARTer dT30VN | 6 | 1 | yes | Advantage | 50 | |
| HEK_SMRT_10 | HEK293T | H. sapiens | 0.256 | 1228 | SMARTer Oligo IIA | 1 | SMARTscribe | SMARTer dT30VN | 6 | 1 | yes | Advantage | 50 | |
| HEK_SMRT_11 | HEK293T | H. sapiens | 0.072 | 1238 | SMARTer Oligo IIA | 1 | SMARTscribe | SMARTer dT30VN | 6 | 1 | yes | Advantage | 50 | |
| HEK_SMRT_12 | HEK293T | H. sapiens | 0.256 | 1292 | SMARTer Oligo IIA | 1 | SMARTscribe | SMARTer dT30VN | 6 | 1 | yes | Advantage | 50 | |
| C_1 | C2C12 | M. musculus | 3.003 | 1696 | rGrG + G | 1 | SSRTII | SMARTer dT30VN | 12 | 1 | — | KAPA HiFi HS | 25 | Could be a cell aggregate |
| C_2 | C2C12 | M. musculus | 1.110 | 1772 | rGrG + G | 1 | SSRTII | SMARTer dT30VN | 12 | 1 | — | KAPA HiFi HS | 25 | |
| C_3 | C2C12 | M. musculus | 1.157 | 1660 | rGrG + G | 1 | SSRTII | SMARTer dT30VN | 12 | 1 | — | KAPA HiFi HS | 25 | |
| C_4 | C2C12 | M. musculus | 1.965 | 1674 | rGrG + G | 1 | SSRTII | SMARTer dT30VN | 12 | 1 | — | KAPA HiFi HS | 25 | |
| C_5 | C2C12 | M. musculus | 2.884 | 1708 | rGrG + G | 1 | SSRTII | SMARTer dT30VN | 12 | 1 | — | KAPA HiFi HS | 25 | Could be a cell aggregate |
| C_6 | C2C12 | M. musculus | 2.325 | 1646 | rGrG + G | 1 | SSRTII | SMARTer dT30VN | 12 | 1 | — | KAPA HiFi HS | 25 | |
| C_7 | C2C12 | M. musculus | 1.941 | 1577 | rGrG + G | 1 | SSRTII | SMARTer dT30VN | 12 | 1 | — | KAPA HiFi HS | 25 | |
| C_8 | C2C12 | M. musculus | 2.248 | 1666 | rGrG + G | 1 | SSRTII | SMARTer dT30VN | 12 | 1 | — | KAPA HiFi HS | 25 | |
| C_9 | C2C12 | M. musculus | 1.379 | 1614 | rGrG + G | 1 | SSRTII | SMARTer dT30VN | 12 | 1 | — | KAPA HiFi HS | 50 | |
| C_10 | C2C12 | M. musculus | 1.832 | 1809 | rGrG + G | 1 | SSRTII | SMARTer dT30VN | 12 | 1 | — | KAPA HiFi HS | 50 | |
| C_11 | C2C12 | M. musculus | 3.644 | 1735 | rGrG + G | 1 | SSRTII | SMARTer dT30VN | 12 | 1 | — | KAPA HiFi HS | 50 | Could be a cell aggregate |
| C_12 | C2C12 | M. musculus | 1.245 | 1735 | rGrG + G | 1 | SSRTII | SMARTer dT30VN | 12 | 1 | — | KAPA HiFi HS | 50 | |
| C_13 | C2C12 | M. musculus | 1.913 | 1896 | rGrG + G | 1 | SSRTII | SMARTer dT30VN | 12 | 1 | — | KAPA HiFi HS | 50 | |
| C_14 | C2C12 | M. musculus | 1.703 | 1836 | rGrG + G | 1 | SSRTII | SMARTer dT30VN | 12 | 1 | — | KAPA HiFi HS | 50 | |
| C_15 | C2C12 | M. musculus | 1.588 | 1937 | rGrG + G | 1 | SSRTII | SMARTer dT30VN | 12 | 1 | — | KAPA HiFi HS | 50 | |
| C_16 | C2C12 | M. musculus | 1.730 | 1937 | rGrG + G | 1 | SSRTII | SMARTer dT30VN | 12 | 1 | — | KAPA HiFi HS | 50 | |

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| MEF_1 | MEF | M. musculus | 0.999 | 1397 | rGrG + G | 1 | SSRTII | SMARTer dT30VN | 12 | 1 | — | KAPA HiFi HS | 25 | |
| MEF_2 | MEF | M. musculus | 2.862 | 1710 | rGrG + G | 1 | SSRTII | SMARTer dT30VN | 12 | 1 | — | KAPA HiFi HS | 25 | |
| MEF_3 | MEF | M. musculus | 1.571 | 1577 | rGrG + G | 1 | SSRTII | SMARTer dT30VN | 12 | 1 | — | KAPA HiFi HS | 25 | |
| MEF_4 | MEF | M. musculus | 1.120 | 1489 | rGrG + G | 1 | SSRTII | SMARTer dT30VN | 12 | 1 | — | KAPA HiFi HS | 25 | |
| MEF_5 | MEF | M. musculus | 2.121 | 1672 | rGrG + G | 1 | SSRTII | SMARTer dT30VN | 12 | 1 | — | KAPA HiFi HS | 25 | |
| MEF_6 | MEF | M. musculus | 5.025 | 1610 | rGrG + G | 1 | SSRTII | SMARTer dT30VN | 12 | 1 | — | KAPA HiFi HS | 25 | Could be a cell aggregate |
| MEF_7 | MEF | M. musculus | 5.874 | 1065 | rGrG + G | 1 | SSRTII | SMARTer dT30VN | 12 | 1 | — | KAPA HiFi HS | 25 | Could be a cell aggregate |
| MEF_8 | MEF | M. musculus | 1.272 | ? | rGrG + G | 1 | SSRTII | SMARTer dT30VN | 12 | 1 | — | KAPA HiFi HS | 25 | |
| MEF_9 | MEF | M. musculus | 1.650 | ? | rGrG + G | 1 | SSRTII | SMARTer dT30VN | 12 | 1 | — | KAPA HiFi HS | 25 | |
| MEF_10 | MEF | M. musculus | 2.071 | ? | rGrG + G | 1 | SSRTII | SMARTer dT30VN | 12 | 1 | — | KAPA HiFi HS | 25 | |
| MEF_11 | MEF | M. musculus | 0.755 | ? | rGrG + G | 1 | SSRTII | SMARTer dT30VN | 12 | 1 | — | KAPA HiFi HS | 25 | |
| MEF_12 | MEF | M. musculus | 7.528 | ? | rGrG + G | 1 | SSRTII | SMARTer dT30VN | 12 | 1 | — | KAPA HiFi HS | 25 | Could be a cell aggregate |
| MEF_13 | MEF | M. musculus | 2.271 | ? | rGrG + G | 1 | SSRTII | SMARTer dT30VN | 12 | 1 | — | KAPA HiFi HS | 25 | |
| MEF_14 | MEF | M. musculus | 2.327 | ? | rGrG + G | 1 | SSRTII | SMARTer dT30VN | 12 | 1 | — | KAPA HiFi HS | 25 | |
| MEF_15 | MEF | M. musculus | 3.149 | ? | rGrG + G | 1 | SSRTII | SMARTer dT30VN | 12 | 1 | — | KAPA HiFi HS | 25 | Could be a cell aggregate |
| MEF_16 | MEF | M. musculus | 2.045 | ? | rGrG + G | 1 | SSRTII | SMARTer dT30VN | 12 | 1 | — | KAPA HiFi HS | 25 | |
| MEF_17 | MEF | M. musculus | 0.497 | 1803 | rGrGrG | 1 | SSRTII | SMARTer dT30VN | 12 | 1 | — | KAPA HiFi HS | 50 | |
| MEF_18 | MEF | M. musculus | 0.427 | 1879 | rGrGrG | 1 | SSRTII | SMARTer dT30VN | 12 | 1 | — | KAPA HiFi HS | 50 | |
| MEF_19 | MEF | M. musculus | 0.406 | 1873 | rGrGrG | 1 | SSRTII | SMARTer dT30VN | 12 | 1 | — | KAPA HiFi HS | 50 | |
| MEF_20 | MEF | M. musculus | 0.680 | 1984 | rGrGrG | 1 | SSRTII | SMARTer dT30VN | 12 | 1 | — | KAPA HiFi HS | 50 | |
| MEF_21 | MEF | M. musculus | 0.429 | 1738 | rGrGrG | 1 | SSRTII | SMARTer dT30VN | 12 | 1 | — | KAPA HiFi HS | 50 | |
| MEF_22 | MEF | M. musculus | 0.634 | 2089 | rGrGrG | 1 | SSRTII | SMARTer dT30VN | 12 | 1 | — | KAPA HiFi HS | 50 | |
| MEF_23 | MEF | M. musculus | 0.722 | 2019 | rGrGrG | 1 | SSRTII | SMARTer dT30VN | 12 | 1 | — | KAPA HiFi HS | 50 | |
| MEF_24 | MEF | M. musculus | 0.397 | 1881 | rGrGrG | 1 | SSRTII | SMARTer dT30VN | 12 | 1 | — | KAPA HiFi HS | 50 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| MEF_25 | MEF | M. musculus | 0.981 | 2007 | rGrG + G | 1 | SSRTII | SMARTer dT30VN | 12 | 1 | — | Advantage | 50 | |
| MEF_26 | MEF | M. musculus | 0.626 | 1827 | rGrG + G | 1 | SSRTII | SMARTer dT30VN | 12 | 1 | — | Advantage | 50 | |
| MEF_28 | MEF | M. musculus | 0.656 | 1979 | rGrG + G | 1 | SSRTII | SMARTer dT30VN | 12 | 1 | — | Advantage | 50 | |
| MEF_29 | MEF | M. musculus | 1.356 | 2143 | rGrG + G | 1 | SSRTII | SMARTer dT30VN | 12 | 1 | — | Advantage | 50 | |
| MEF_30 | MEF | M. musculus | 1.242 | 2137 | rGrG + G | 1 | SSRTII | SMARTer dT30VN | 12 | 1 | — | Advantage | 50 | |
| MEF_31 | MEF | M. musculus | 2.240 | 2015 | rGrG + G | 1 | SSRTII | SMARTer dT30VN | 12 | 1 | — | Advantage | 50 | |
| MEF_32 | MEF | M. musculus | 0.781 | 1817 | rGrG + G | 1 | SSRTII | SMARTer dT30VN | 12 | 1 | — | Advantage | 50 | |
| MEF_33 | MEF | M. musculus | 0.603 | 1781 | rGrG + G | 1 | SSRTII | SMARTer dT30VN | 12 | 1 | — | KAPA HiFi HS | 50 | |
| MEF_34 | MEF | M. musculus | 5.014 | 1894 | rGrG + G | 1 | SSRTII | SMARTer dT30VN | 12 | 1 | — | KAPA HiFi HS | 50 | Could be a cell aggregate |
| MEF_35 | MEF | M. musculus | 1.651 | 2064 | rGrG + G | 1 | SSRTII | SMARTer dT30VN | 12 | 1 | — | KAPA HiFi HS | 50 | |
| MEF_36 | MEF | M. musculus | 1.017 | 1773 | rGrG + G | 1 | SSRTII | SMARTer dT30VN | 12 | 1 | — | KAPA HiFi HS | 50 | |
| MEF_37 | MEF | M. musculus | 1.119 | 1783 | rGrG + G | 1 | SSRTII | SMARTer dT30VN | 12 | 1 | — | KAPA HiFi HS | 50 | |
| MEF_38 | MEF | M. musculus | 0.681 | 1659 | rGrG + G | 1 | SSRTII | SMARTer dT30VN | 12 | 1 | — | KAPA HiFi HS | 50 | |
| MEF_39 | MEF | M. musculus | 1.444 | 1469 | rGrG + G | 1 | SSRTII | SMARTer dT30VN | 12 | 1 | — | KAPA HiFi HS | 50 | |
| MEF_40 | MEF | M. musculus | 0.845 | 1401 | rGrG + G | 1 | SSRTII | SMARTer dT30VN | 12 | 1 | — | KAPA HiFi HS | 50 | |
| SMRT_1 | C2C12 | M. musculus | 0.063 | 1170 | SMARTer Oligo IIA | 1 | SMARTscribe | SMARTer dT30VN | 12 | 1 | yes | Advantage | 50 | |
| SMRT_2 | C2C12 | M. musculus | 0.165 | 1127 | SMARTer Oligo IIA | 1 | SMARTscribe | SMARTer dT30VN | 12 | 1 | yes | Advantage | 50 | |
| SMRT_3 | C2C12 | M. musculus | 0.130 | 1169 | SMARTer Oligo IIA | 1 | SMARTscribe | SMARTer dT30VN | 12 | 1 | yes | Advantage | 50 | |
| SMRT_4 | C2C12 | M. musculus | 0.091 | 1325 | SMARTer Oligo IIA | 1 | SMARTscribe | SMARTer dT30VN | 12 | 1 | yes | Advantage | 50 | |
| SMRT_5 | C2C12 | M. musculus | 0.036 | 1282 | SMARTer Oligo IIA | 1 | SMARTscribe | SMARTer dT30VN | 12 | 1 | yes | Advantage | 50 | |
| SMRT_6 | C2C12 | M. musculus | 0.135 | 1373 | SMARTer Oligo IIA | 1 | SMARTscribe | SMARTer dT30VN | 12 | 1 | yes | Advantage | 50 | |
| SMRT_7 | C2C12 | M. musculus | 0.161 | 1525 | SMARTer Oligo IIA | 1 | SMARTscribe | SMARTer dT30VN | 12 | 1 | yes | Advantage | 50 | |
| SMRT_8 | C2C12 | M. musculus | 0.178 | 1314 | SMARTer Oligo IIA | 1 | SMARTscribe | SMARTer dT30VN | 12 | 1 | yes | Advantage | 50 | |
| SMRT_9 | C2C12 | M. musculus | 0.036 | 1363 | SMARTer Oligo IIA | 1 | SMARTscribe | SMARTer dT30VN | 12 | 1 | yes | Advantage | 50 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| SMRT_10 | C2C12 | M. musculus | 0.129 | 1261 | SMARTer Oligo IIA | 1 | SMARTscribe | SMARTer dT30VN | 12 | 1 | yes | Advantage | 50 | |
| SMRT_11 | C2C12 | M. musculus | 0.080 | 1234 | SMARTer Oligo IIA | 1 | SMARTscribe | SMARTer dT30VN | 12 | 1 | yes | Advantage | 50 | |
| SMRT_12 | C2C12 | M. musculus | 0.111 | 1447 | SMARTer Oligo IIA | 1 | SMARTscribe | SMARTer dT30VN | 12 | 1 | yes | Advantage | 50 | |
| SMRT_14 | C2C12 | M. musculus | 0.081 | 1408 | SMARTer Oligo IIA | 1 | SMARTscribe | SMARTer dT30VN | 12 | 1 | yes | Advantage | 50 | |
| SMRT_16 | C2C12 | M. musculus | 0.074 | 1280 | SMARTer Oligo IIA | 1 | SMARTscribe | SMARTer dT30VN | 12 | 1 | yes | Advantage | 50 | |
| BC_1 | B-cells | H. sapiens | 0.826 | 1657 | rGrG + G | 1 | SSRTII | SMARTer dT30VN | 12 | 1 | — | KAPA HiFi HS | 50 | |
| BC_3 | B-cells | H. sapiens | 1.091 | 1659 | rGrG + G | 1 | SSRTII | SMARTer dT30VN | 12 | 1 | — | KAPA HiFi HS | 50 | |
| BC_4 | B-cells | H. sapiens | 0.401 | 1649 | rGrG + G | 1 | SSRTII | SMARTer dT30VN | 12 | 1 | — | KAPA HiFi HS | 50 | |
| BC_5 | B-cells | H. sapiens | 0.501 | 1547 | rGrG + G | 1 | SSRTII | SMARTer dT30VN | 12 | 1 | — | KAPA HiFi HS | 50 | |
| BC_6 | B-cells | H. sapiens | 0.573 | 1534 | rGrG + G | 1 | SSRTII | SMARTer dT30VN | 12 | 1 | — | KAPA HiFi HS | 50 | |
| BC_7 | B-cells | H. sapiens | 0.328 | 1343 | rGrG + G | 1 | SSRTII | SMARTer dT30VN | 12 | 1 | — | KAPA HiFi HS | 50 | |
| BC_8 | B-cells | H. sapiens | 0.661 | 1607 | rGrG + G | 1 | SSRTII | SMARTer dT30VN | 12 | 1 | — | KAPA HiFi HS | 50 | |
| BC_9 | B-cells | H. sapiens | 0.500 | 1605 | rGrG + G | 1 | SSRTII | SMARTer dT30VN | 12 | 1 | — | KAPA HiFi HS | 50 | |
| BC_10 | B-cells | H. sapiens | 0.840 | 1782 | rGrG + G | 1 | SSRTII | SMARTer dT30VN | 12 | 1 | — | KAPA HiFi HS | 50 | |
| BC_11 | B-cells | H. sapiens | 0.829 | 1813 | rGrG + G | 1 | SSRTII | SMARTer dT30VN | 12 | 1 | — | KAPA HiFi HS | 50 | |
| BC_12 | B-cells | H. sapiens | 0.648 | 1642 | rGrG + G | 1 | SSRTII | SMARTer dT30VN | 12 | 1 | — | KAPA HiFi HS | 50 | |
| BC_13 | B-cells | H. sapiens | 0.297 | 1815 | rGrG + G | 1 | SSRTII | SMARTer dT30VN | 12 | 1 | — | KAPA HiFi HS | 50 | |
| BC_15 | B-cells | H. sapiens | 0.982 | 1825 | rGrG + G | 1 | SSRTII | SMARTer dT30VN | 12 | 1 | — | KAPA HiFi HS | 50 | |
| HEK_159 | HEK293T | H. sapiens | 3.057 | 1464 | rGrG + G | 1 | SSRTII | SMARTer dT30VN | 15 | 1 | — | KAPA HiFi HS | 25 | Could be a cell aggregate |
| HEK_160 | HEK293T | H. sapiens | 3.506 | 1799 | rGrG + G | 1 | SSRTII | SMARTer dT30VN | 15 | 1 | — | KAPA HiFi HS | 25 | Could be a cell aggregate |
| HEK_161 | HEK293T | H. sapiens | 2.027 | 1611 | rGrG + G | 1 | SSRTII | SMARTer dT30VN | 15 | 1 | — | KAPA HiFi HS | 25 | |
| HEK_162 | HEK293T | H. sapiens | 2.513 | 1714 | rGrG + G | 1 | SSRTII | SMARTer dT30VN | 15 | 1 | — | KAPA HiFi HS | 25 | |
| HEK_163 | HEK293T | H. sapiens | 0.558 | 909 | rGrG + G | 1 | SSRTII | SMARTer dT30VN | 20 | 1 | — | KAPA HiFi HS | 25 | |
| HEK_164 | HEK293T | H. sapiens | 1.490 | 1397 | rGrG + G | 1 | SSRTII | SMARTer dT30VN | 20 | 1 | — | KAPA HiFi HS | 25 | |

-continued

| sample | cell type | species | conc (ng/ul) | avg size (bp) | TSO | amount TSO (ul of 10 uM solution in 10 ul RT rxn) | RT enzyme | oligo dT | MgCl2 (mM) | betaine (M) | purification after RT? | PCR enzyme | PCR rxn vol (ul) | notes |
|---|---|---|---|---|---|---|---|---|---|---|---|---|---|---|
| HEK_165 | HEK293T | H. sapiens | 0.606 | 1334 | rGrG + G | 1 | SSRTII | SMARTer dT30VN | 20 | 1 | — | KAPA HiFi HS | 25 | |
| HEK_166 | HEK293T | H. sapiens | 1.203 | 1515 | rGrG + G | 1 | SSRTII | SMARTer dT30VN | 20 | 1 | — | KAPA HiFi HS | 25 | |
| BC_17 | B-cells | H. sapiens | 0.393 | 1603 | rGrG + G | 1 | SSRTII | SMARTer dT30VN | 12 | — | — | KAPA HiFi HS | 50 | |
| BC_19 | B-cells | H. sapiens | 0.216 | 1730 | rGrG + G | 1 | SSRTII | SMARTer dT30VN | 12 | — | — | KAPA HiFi HS | 50 | |
| BC_20 | B-cells | H. sapiens | 0.074 | 1131 | rGrG + G | 1 | SSRTII | SMARTer dT30VN | 12 | — | — | KAPA HiFi HS | 50 | |
| BC_21 | B-cells | H. sapiens | 0.126 | 1445 | rGrG + G | 1 | SSRTII | SMARTer dT30VN | 12 | — | — | KAPA HiFi HS | 50 | |
| BC_22 | B-cells | H. sapiens | 0.325 | 1702 | rGrG + G | 1 | SSRTII | SMARTer dT30VN | 12 | — | — | KAPA HiFi HS | 50 | |
| BC_23 | B-cells | H. sapiens | 0.183 | 1756 | rGrG + G | 1 | SSRTII | SMARTer dT30VN | 12 | — | — | KAPA HiFi HS | 50 | |
| BC_24 | B-cells | H. sapiens | 0.097 | 1338 | rGrG + G | 1 | SSRTII | SMARTer dT30VN | 12 | — | — | KAPA HiFi HS | 50 | |
| BC_25 | B-cells | H. sapiens | 0.826 | 1657 | rGrG + G | 1 | SSRTII | SMARTer dT30VN | 12 | 1 | — | KAPA HiFi HS | 50 | |
| BC_26 | B-cells | H. sapiens | 1.091 | 1659 | rGrG + G | 1 | SSRTII | SMARTer dT30VN | 12 | 1 | — | KAPA HiFi HS | 50 | |
| BC_27 | B-cells | H. sapiens | 0.401 | 1649 | rGrG + G | 1 | SSRTII | SMARTer dT30VN | 12 | 1 | — | KAPA HiFi HS | 50 | |
| BC_28 | B-cells | H. sapiens | 0.501 | 1547 | rGrG + G | 1 | SSRTII | SMARTer dT30VN | 12 | 1 | — | KAPA HiFi HS | 50 | |
| BC_29 | B-cells | H. sapiens | 0.573 | 1534 | rGrG + G | 1 | SSRTII | SMARTer dT30VN | 12 | 1 | — | KAPA HiFi HS | 50 | |
| BC_30 | B-cells | H. sapiens | 0.328 | 1343 | rGrG + G | 1 | SSRTII | SMARTer dT30VN | 12 | 1 | — | KAPA HiFi HS | 50 | |
| BC_31 | B-cells | H. sapiens | 0.661 | 1607 | rGrG + G | 1 | SSRTII | SMARTer dT30VN | 12 | 1 | — | KAPA HiFi HS | 50 | |
| BC_32 | B-cells | H. sapiens | 0.500 | 1605 | rGrG + G | 1 | SSRTII | SMARTer dT30VN | 12 | 1 | — | KAPA HiFi HS | 50 | |
| BC_33 | B-cells | H. sapiens | 0.840 | 1782 | rGrG + G | 1 | SSRTII | SMARTer dT30VN | 12 | 1 | — | KAPA HiFi HS | 50 | |
| BC_34 | B-cells | H. sapiens | 0.829 | 1813 | rGrG + G | 1 | SSRTII | SMARTer dT30VN | 12 | 1 | — | KAPA HiFi HS | 50 | |
| BC_35 | B-cells | H. sapiens | 0.648 | 1642 | rGrG + G | 1 | SSRTII | SMARTer dT30VN | 12 | 1 | — | KAPA HiFi HS | 50 | |
| BC_36 | B-cells | H. sapiens | 0.297 | 1815 | rGrG + G | 1 | SSRTII | SMARTer dT30VN | 12 | 1 | — | KAPA HiFi HS | 50 | |
| BC_37 | B-cells | H. sapiens | 0.982 | 1825 | rGrG + G | 1 | SSRTII | SMARTer dT30VN | 12 | 1 | — | KAPA HiFi HS | 50 | |
| BC_38 | B-cells | H. sapiens | 0.853 | 1795 | rGrG + G | 1 | SSRTII | SMARTer dT30VN | 12 | 1 | — | KAPA HiFi HS | 50 | |

TABLE S4

Detailing variants of the Smart-seq2 protocol

| Protocol name | TSO | amount ISO (ul) | Bead purification before pre-amplification? | DNA Polymerase |
|---|---|---|---|---|
| Smart-seq2 | rGrG+G | 1 ul (10 uM) | no | KAPA HiFi HotStart ReadyMix |
| Variant 1 | rGrG+G | 2 ul (10 uM) | no | KAPA HiFi HotStart ReadyMix |
| Variant 2 | rGrG+N | 2 ul (10 uM) | no | KAPA HiFi HotStart ReadyMix |
| Variant 3 | rGrG+G | 1 ul (10 uM) | no | Advantage 2 |
| Variant 4 | rGrGrG | 1 ul (10 uM) | no | KAPA HiFi HotStart ReadyMix |
| SMARTer | SMARTer Oligo IIA | 1 ul (12 uM) | yes | Advantage 2 |

The invention claimed is:

1. A method for preparing DNA that is complementary to an RNA molecule, comprising the steps of:
   annealing a cDNA synthesis primer to said RNA molecule and synthesizing a first cDNA strand to form an RNA-cDNA intermediate; and
   conducting a reverse transcriptase reaction by contacting said RNA-cDNA intermediate with a template switching oligonucleotide (TSO), wherein the TSO comprises a locked nucleic acid (LNA) at its 3'-most end, under conditions suitable for extension of the first DNA strand that is complementary to the RNA molecule, rendering it additionally complementary to the TSO.

2. The method of claim 1, wherein said reverse transcription reaction is conducted in the presence of a methyl group donor and a metal salt.

3. The method of claim 2, wherein said methyl group is betaine.

4. The method of claim 2, wherein said metal salt is magnesium salt.

5. The method of claim 4, wherein said magnesium salt has a concentration of at least 7 mM.

6. The method of claim 1, wherein said template switching oligonucleotide comprises at least one or two ribonucleotide residues and said LNA residue.

7. The method of claim 6, wherein said at least one or two ribonucleotide residues are riboguanine.

8. The method of claim 6, wherein said locked nucleic acid residue is selected from the group consisting of locked guanine, locked adenine, locked uracil, locked thymine, locked cytosine, and locked 5-methylcytosine.

9. The method of claim 8, wherein said locked nucleic acid residue is locked guanine.

10. The method of claim 1, wherein said template switching oligonucleotide comprises at a 3'-end three nucleotide residues characterized by formula rGrG+N, wherein +N represents a locked nucleotide residue.

11. The method of claim 10, wherein said template switching oligonucleotide comprises rGrG+G.

12. The method of claim 2, wherein said methyl group donor is betaine, and said metal salt is $MgCl_2$ at a concentration of at least 9 mM.

13. The method of claim 1, further comprising amplifying said DNA strand that is complementary to said RNA molecule and said template switching oligonucleotide using an oligonucleotide primer.

14. The method of claim 1, wherein said template switching oligonucleotide is selected from the group consisting of:

i. rGrG+G (AAGCAGTGGTATCAACGCAGAGTACrGrG+G), ii. rGrG+N (AAGCAGTGGTATCAACGCAGAGTACrGrG+N),

```
     -continued
iii. +G+G+G (AAGCAGTGGTATCAACGCAGAGTAC+G+G+G),
     and iv.  rG+G+G (AAGCAGTGGTATCAACGCAGAGTACrG+G+G).
```

15. The method of claim 1, wherein the cDNA is synthesized on beads comprising an anchored oligo-dT primer.

16. The method of claim 15, wherein said oligo-dT primer comprises a sequence of 5'-AAGCAGTGGTATCAACGCAGAGTACT$_{30}$VN-3', wherein "N" is any nucleoside base, and "V" is selected from the group consisting of "A", "C" and "G".

17. The method of claim 13, further comprising PCR preamplification, tagmentation, and final PCR amplification.

18. A method for analyzing gene expression in a plurality of single cells, the method comprising the steps of: preparing a cDNA library according to the method of claim 1; and sequencing the cDNA library.

19. A template switching oligonucleotide (TSO) comprising a locked nucleotide residue at its 3'-most end.

20. The TSO of claim 19, comprising three nucleotide residues at a 3'-end selected from the group consisting of +N+N+N, N+N+N, NN+N, rN+N+N, and rNrN+N, wherein N at each occurrence is independently a deoxyribonucleotide residue, rN at each occurrence is independently a ribonucleotide residue, and +N at each occurrence is independently a locked nucleotide residue.

21. The TSO of claim 19, wherein said locked nucleotide residue is selected from the group consisting of locked guanine, locked adenine, locked uracil, locked thymine, locked cytosine, and locked 5-methylcytosine.

22. The TSO of claim 20, wherein said three nucleotide residues are selected from the group consisting of NN+G, rNrN+G, GG+N, rGrG+G, and GG+G.

23. The method of claim 1, wherein said RNA is total RNA in a cell.

24. The method of claim 13, wherein optionally the PCR preamplification is conducted without purifying the cDNA obtained from reverse transcription reaction.

* * * * *